United States Patent
Oiry et al.

(10) Patent No.: US 6,979,747 B2
(45) Date of Patent: Dec. 27, 2005

(54) ANTIOXIDANTS, PREPARATION PROCESSES AND THEIR USES

(75) Inventors: Joel Oiry, Montpellier (FR); Jean-Yves Puy, Montpellier (FR); Jean-Louis Imbach, Montpellier (FR); Pascal Clayette, Versailles (FR); Philippe Fretier, Nogent sur Marne (FR)

(73) Assignees: Centre National de la Recherche Scientifique (CNRS), Paris (FR); Commissariat A L'Energie Atomique, Paris (FR)

( * ) Notice: Subject to any disclaimer, the term of this patent is extended or adjusted under 35 U.S.C. 154(b) by 124 days.

(21) Appl. No.: 10/738,267

(22) Filed: Dec. 16, 2003

(65) Prior Publication Data

US 2004/0158092 A1 Aug. 12, 2004

Related U.S. Application Data

(62) Division of application No. 09/980,291, filed as application No. PCT/FR00/01447 on May 26, 2000.

(30) Foreign Application Priority Data

May 27, 1999 (FR) .............................................. 99 06708

(51) Int. Cl.$^7$ .............................................. C07C 327/30
(52) U.S. Cl. ........................ 560/147; 530/330; 530/331
(58) Field of Search .......................... 560/147; 530/330, 530/331

(56) References Cited

U.S. PATENT DOCUMENTS

| | | | |
|---|---|---|---|
| 4,927,808 A | * | 5/1990 | Kitahara et al. .............. 514/19 |
| 5,624,955 A | * | 4/1997 | Nagasawa et al. .......... 514/513 |

* cited by examiner

*Primary Examiner*—Kamal A. Saeed
(74) *Attorney, Agent, or Firm*—Blakely Sokoloff Taylor & Zafman

(57) ABSTRACT

The invention concerns a process for preparing compounds of general formula (I)

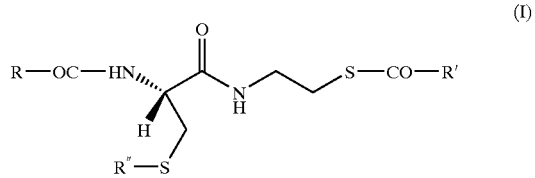

Figure 1:
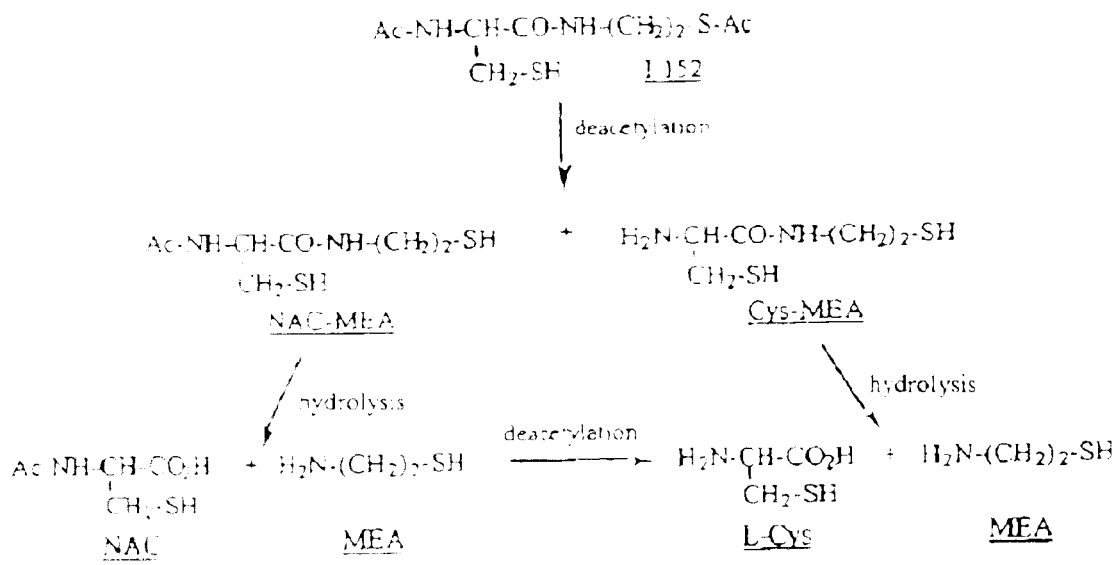

wherein R and R' represent an alkyl radical or an aryl group; and R" is hydrogen or a CO—R$^1$ group wherein R$^1$ is an alkyl radical or an aryl group; and wherein these compounds are or not in the thiazolidine form; by protecting the N-acyl-L-cysteine to form an intermediate compound; and then by coupling said intermediate compound with S-acylcysteamine hydrochloride or with thiazolidine.

18 Claims, 17 Drawing Sheets

ANTIOXIDANTS, PREPARATION PROCESSES AND THEIR USES

The present patent application is a Divisional of Application No. 09/980,291, filed Nov. 27, 2001, which is a 371 PCT/FR00/01447, filed May 26, 2000.

The present invention relates to novel compounds possessing antioxidant activity, to their processes of preparation and to their uses, in particular in the preparation of medicaments intended to increase the intracellular and/or extracellular level of glutathione (GSH).

An increasing number of studies are showing that reactive oxygen species play an important role in many biological processes and in particular in the development of many human pathologies and more particularly in retroviral infections by the human immunodeficiency virus (HIV).

Reactive oxygen species (ROS, superoxide ion, hydrogen peroxide, hypochlorous ion, hydroxyl radicals, and the like) are natural products of variable origin; they originate from activated inflammatory cells, cells which metabolize xenobiotics or cells exposed to specific environmental milieus, such as cigarette smoke.

Various substances are known for being active in scavenging these reactive oxygen species at the intracellular or extracellular level.

Mention may be made, for example, of glutathione, which is a tripeptide (L-γ-glutamyl-L-cysteinylglycine, GSH) found in all eukaryote cells. It is synthesized and decomposed in the cell, mainly via its reduced form, GSH. This reduced tripeptide, which participates in many cell functions, such as, for example, protein and nucleic acid synthesis, and the transportation of amino acids, constitutes the main mechanism for intracellular defense against oxidative stress. The factors which promote the formation of reactive oxygen species lead to the consumption of the glutathione reserves.

N-Acetyl-L-cysteine (NAC) has been known for many years as a medicament for the cornea, as an antidote to poisoning by acetaminophen and as a mucolytic agent by cleaving the disulfide bonds in mucoproteins. Because NAC is used therapeutically in many pathologies in which oxidizing agents seem to play a role, it has been suggested that it operates as an antioxidant. The mechanism of action of NAC is based on its ability to reduce extracellular cystine to cysteine or to be a source of SH (thiol functional group) metabolites. As a source of SH groups, NAC stimulates the synthesis of GSH, enhances the glutathione S-transferase activity, promotes detoxification and acts directly on reactive oxidizing species. NAC and, by extension, the acylated variants of the amino acid L-cysteine are an excellent source of SH groups and are converted in the body into metabolites capable of stimulating the synthesis of glutathione, thus promoting detoxification and acting directly as scavengers of reactive oxygen species.

In view of the central role of GSH in cell detoxification mechanisms, numerous alternatives targeted at raising its intracellular level have been envisaged as adjuvant therapeutic strategy in numerous human pathologies and more particularly in infection by the human immunodeficiency virus (HIV) in recent years (WO 92/21368; WO 95/10268; U.S. Pat. Nos. 4,927,808; 5,580,577). The problem was first of all approached by seeking to supplement the deficient molecule. Subsequent approaches were targeted at feeding the γ-glutamyl cycle. Thus, L-cysteine, GSH itself, NAC, 2-oxothiazolidine-4(R)-carboxylic acid (OTC) and cysteamine (MEA), the formulae of which are reproduced below, were tested as potential adjuvants for antiretrovirals in the treatment of infections by the HIV.

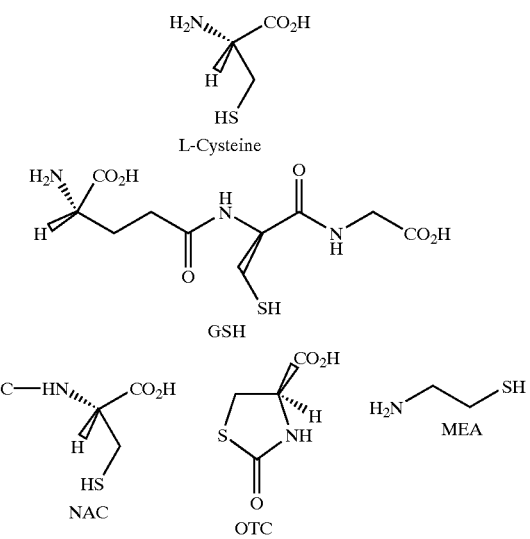

The beneficial effects of these molecules have been limited in vivo by low bioavailability, excessively rapid metabolization and insufficient concentrations which can be administered. NAC, for example, is a relatively labile molecule which, during its rapid decomposition, releases compounds comprising malodorous sulfides, such as $H_2S$. This problem of instability has limited the use of NAC or other compounds providing a source of —SH, such as L-cysteine or its acylated variants, in the preparation of formulations which can be used in pharmacology, dermatology or cosmetics.

The inventors have now developed novel compounds, capable of acting on the intracellular or extracellular level of glutathione, which do not exhibit the instability which was found for the known products. This is why a subject matter of the present invention is the compounds of following general formula (I):

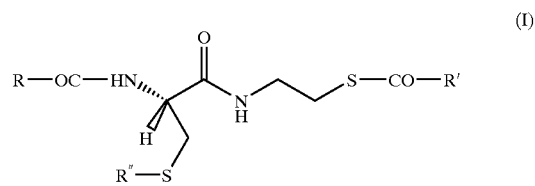

and in which:
R and R' independently represent a linear or branched $C_1$–$C_7$ alkyl radical or an aryl group which is unsubstituted or substituted by one or more radicals chosen from halogens, linear or branched $C_1$–$C_3$ alkyl radicals and —OH (hydroxyl) radicals;
R" is hydrogen or a CO—$R^1$ group in which $R^1$ is a linear or branched $C_1$–$C_7$ alkyl radical or an aryl group which is unsubstituted or substituted by one or more radicals chosen from halogens, linear or branched $C_1$–$C_3$ alkyl radicals and —OH radicals;
and the dimers formed by a disulfide bridge from one and/or other of the two sulfur atoms of the molecule of general formula I composed of the R" radicals or of the R'CO— radicals of the two molecules, and the corresponding thiazolidine forms.

The R, R' and R" alkyl radicals are preferably $C_1$–$C_3$ radicals. The halogens are preferably chlorine and fluorine.

In these compounds, NAC and MEA are combined and are or are not protected by biolabile groups.

According to a preferred embodiment, the present invention relates to a compound of general formula I such that R is a methyl group (—CH$_3$). In a more preferred embodiment, the present invention relates to a compound of general formula I such that R and R' are methyl groups (—CH$_3$). In the preferred embodiment, the invention relates to the compound known as N-(N-acetyl-L-cysteinyl)-S-acetylcysteamine, known below as I-152, such that, in the general formula I, R and R' are methyl groups (—CH$_3$) and R" is hydrogen.

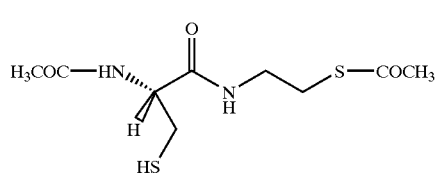

I-152

This compound is particularly advantageous for its properties, which render it active in the treatment and/or prevention of pathologies or disorders related to an intra- and/or extracellular depletion in glutathione, in particular the treatment of viral infections and more particularly infections by the human immunodeficiency virus (HIV).

According to another preferred embodiment, the invention relates to the compound known as N-(N,S-bisacetyl-L-cysteinyl)-S-acetylcysteamine, known below as I-176, such that, in the general formula I, R and R' are methyl groups (—CH$_3$) and R" is an acetyl group (—COCH$_3$).

According to another preferred embodiment, the invention relates to the compound known as N-(N-acetyl-S-isobutyryl-L-cysteinyl)-S-acetylcysteamine, known below as I-177, such that, in the general formula I, R and R' are methyl groups (—CH$_3$) and R" is an isobutyryl group (—COCH(CH$_3$)$_2$).

According to another preferred embodiment, the invention relates to the compound known as N-(N-acetyl-S-pivaloyl-L-cysteinyl)-S-acetylcysteamine, known below as I-178, such that, in the general formula I, R and R' are methyl groups (—CH$_3$) and R" is a pivaloyl group (—COC(CH$_3$)$_3$).

It is also one of the objects of the present invention to provide a compound of general formula I in which R is a methyl group (—CH$_3$) and R' is selected from the isopropyl group (—CH(CH$_3$)$_2$), the tert-butyl group (—C(CH$_3$)$_3$) and the phenyl group (—C$_6$H$_5$); such a compound preferably exhibits an R" group selected from hydrogen (—H), the acetyl group (—COCH$_3$), the isobutyryl group (—COCH(CH$_3$)$_2$), the pivaloyl group (—COC(CH$_3$)$_3$) or the benzoyl group (—CO—C$_6$H$_5$). More particularly, the invention is targeted at providing the compound below known as:

I-188, such that, in the general formula I, R is a methyl group (—CH$_3$), R' is an isopropyl group (—CH(CH$_3$)$_2$) and R" is hydrogen (—H).

I-189, such that, in the general formula I, R is a methyl group (—CH$_3$), R' is an isopropyl group (—CH(CH$_3$)$_2$) and R" is the acetyl group (—COCH$_3$).

I-190, such that, in the general formula I, R is a methyl group (—CH$_3$), R' is an isopropyl group (—CH(CH$_3$)$_2$) and R" is the isobutyryl group (—COCH(CH$_3$)$_2$).

I-191, such that, in the general formula I, R is a methyl group (—CH$_3$), R' is an isopropyl group (—CH(CH$_3$)$_2$) and R" is the pivaloyl group (—COC(CH$_3$)$_3$).

I-192, such that, in the general formula I, R is a methyl group (—CH$_3$), R' is an isopropyl group (—CH(CH$_3$)$_2$) and R" is the benzoyl group (—CO—C$_6$H$_5$).

I-193, such that, in the general formula I, R is a methyl group (—CH$_3$), R' is a tert-butyl group (—C(CH$_3$)$_3$) and R" is hydrogen (—H).

I-194, such that, in the general formula I, R is a methyl group (—CH$_3$), R' is a tert-butyl group (—C(CH$_3$)$_3$) and R" is the acetyl group (—COCH$_3$).

I-195, such that, in the general formula I, R is a methyl group (—CH$_3$), R' is a tert-butyl group (—C(CH$_3$)$_3$) and R" is the isobutyryl group (—COCH(CH$_3$)$_2$).

I-196, such that, in the general formula I, R is a methyl group (—CH$_3$), R' is a tert-butyl group (—C(CH$_3$)$_3$) and R" is the pivaloyl group (—COC(CH$_3$)$_3$).

I-197, such that, in the general formula I, R is a methyl group (—CH$_3$), R' is a tert-butyl group (—C(CH$_3$)$_3$) and R" is the benzoyl group (—CO—C$_6$H$_5$).

I-198, such that, in the general formula I, R is a methyl group (—CH$_3$), R' is phenyl group (—C$_6$H$_5$) and R" is hydrogen (—H).

I-199, such that, in the general formula I, R is a methyl group (—CH$_3$), R' is a phenyl group (—C$_6$H$_5$) and R" is the acetyl group (—COCH$_3$).

I-200, such that, in the general formula I, R is a methyl group (—CH$_3$), R' is a phenyl group (—C$_6$H$_5$) and R" is the isobutyryl group (—COCH(CH$_3$)$_2$).

I-201, such that, in the general formula I, R is a methyl group (—CH$_3$), R' is a phenyl group (—C$_6$H$_5$) and R" is the pivaloyl group (—COC(CH$_3$)$_3$).

I-202, such that, in the general formula I, R is a methyl group (—CH$_3$), R' is a phenyl group (—C$_6$H$_5$) and R" is the benzoyl group. (—CO—C$_6$H$_5$).

It is also one of the objects of the present invention to provide a compound of general formula I which constitutes an intermediate in the synthesis of the compound I-152, of its acylated derivatives or of its analogues. Thus, the invention also relates to the compound of general formula I known as 10 in which R is a methyl group (—CH$_3$), R' is the isopropyl group (—CH(CH$_3$)$_2$) and R" is a trityl group. The invention also relates to the compound of general formula I known as 11 in which R is a methyl group (—CH$_3$), R' is the tert-butyl group (—C(CH$_3$)$_3$) and R" is a trityl group. The invention also relates to the compound of general formula I known as 12 in which R is a methyl group (—CH$_3$), R' is the phenyl group (—C$_6$H$_5$) and R" is a trityl group.

It is also one of the objects of the present invention to provide a compound of general formula I in which R is an isopropyl group (—CH(CH$_3$)$_2$); such a compound of the invention is preferably characterized in that R' is selected from the methyl group (—CH$_3$), the isopropyl group (—CH(CH$_3$)$_2$), the tert-butyl group (—C(CH$_3$)$_3$) and the phenyl group (—C$_6$H$_5$); such a compound preferably exhibits an R" group selected from hydrogen (—H), the acetyl group (—COCH$_3$), the isobutyryl group (—COCH(CH$_3$)$_2$), the pivaloyl group (—COC(CH$_3$)$_3$) or the benzoyl group (—CO—C$_6$H$_5$). The invention is more particularly targeted at providing the compound below known as:

I-203, such that, in the general formula I, R is an isopropyl group (—CH(CH$_3$)$_2$), R' is a methyl group (—CH$_3$) and R" is hydrogen (—H).

I-204, such that, in the general formula I, R is an isopropyl group (—CH(CH$_3$)$_2$), R' is a methyl group (—CH$_3$) and R" is the acetyl group (—COCH$_3$).

I-205, such that, in the general formula I, R is an isopropyl group (—CH(CH$_3$)$_2$), R' is a methyl group (—CH$_3$) and R" is the isobutyryl group (—COCH(CH$_3$)$_2$).

I-206, such that, in the general formula I, R is an isopropyl group (—CH(CH$_3$)$_2$), R' is a methyl group (—CH$_3$) and R" is the pivaloyl group (—COC(CH$_3$)$_3$).

I-207, such that, in the general formula I, R is an isopropyl group (—CH(CH$_3$)$_2$), R' is a methyl group (—CH$_3$) and R" is the benzoyl group (—CO—C$_6$H$_5$).

I-208, such that, in the general formula I, R is an isopropyl group (—CH(CH$_3$)$_2$), R' is an isopropyl group (—CH(CH$_3$)$_2$) and R" is hydrogen (—H).

I-209, such that, in the general formula I, R is an isopropyl group (—CH(CH$_3$)$_2$), R' is an isopropyl group (—CH(CH$_3$)$_2$) and R" is the acetyl group (—COCH$_3$).

I-210, such that, in the general formula I, R is an isopropyl group (—CH(CH$_3$)$_2$), R' is an isopropyl group (—CH(CH$_3$)$_2$) and R" is the isobutyryl group (—COCH(CH$_3$)$_2$).

I-211, such that, in the general formula I, R is an isopropyl group (—CH(CH$_3$)$_2$), R' is an isopropyl group (—CH(CH$_3$)$_2$) and R" is the benzoyl group (—CO—C$_6$H$_5$).

I-214, such that, in the general formula I, R is an isopropyl group (—CH(CH$_3$)$_2$), R' is a tert-butyl group (—C(CH$_3$)$_3$) and R" is hydrogen (—H).

I-215, such that, in the general formula I, R is an isopropyl group (—CH(CH$_3$)$_2$), R' is a tert-butyl group (—C(CH$_3$)$_3$) and R" is the acetyl group (—COCH$_3$).

I-216, such that, in the general formula I, R is an isopropyl group (—CH(CH$_3$)$_2$), R' is a tert-butyl group (—C(CH$_3$)$_3$) and R" is the isobutyryl group (—COCH(CH$_3$)$_2$).

I-217, such that, in the general formula I, R is an isopropyl group (—CH(CH$_3$)$_2$), R is a tert-butyl group (—C(CH$_3$)$_3$) and R" is the pivaloyl group (—COC(CH$_3$)$_3$).

I-218, such that, in the general formula I, R is an isopropyl group (—CH(CH$_3$)$_2$), R' is a tert-butyl group (—C(CH$_3$)$_3$) and R" is the benzoyl group (—CO—C$_6$H$_5$).

I-219, such that, in the general formula I, R is an isopropyl group (—CH(CH$_3$)$_2$), R' is a phenyl group (—C$_6$H$_5$) and R" is hydrogen (—H).

I-220, such that, in the general formula I, R is an isopropyl group (—CH(CH$_3$)$_2$), R' is a phenyl group (—C$_6$H$_5$) and R" is the acetyl group (—COCH$_3$).

I-221, such that, in the general formula I, R is an isopropyl group (—CH(CH$_3$)$_2$), R' is a phenyl group (—C$_6$H$_5$) and R" is the isobutyryl group (—COCH(CH$_3$)$_2$).

I-222, such that, in the general formula I, R is an isopropyl group (—CH(CH$_3$)$_2$), R' is a phenyl group (—C$_6$H$_5$) and R" is the pivaloyl group (—COC(CH$_3$)$_3$).

I-223, such that, in the general formula I, R is an isopropyl group (—CH(CH$_3$)$_2$), R' is a phenyl group (—C$_6$H$_5$) and R" is the benzoyl group (—CO—C$_6$H$_5$).

It is also one of the objects of the present invention to provide a compound of general formula I which constitutes an intermediate in the synthesis of the compound I-152, of its acylated derivatives or of its analogues. Thus, the invention also relates to the compound of general formula I known as 14 in which R is an isopropyl group (—CH(CH$_3$)$_2$), R' is a methyl group (—CH$_3$) and R" is a trityl group. The invention also relates to the compound of general formula I known as 15 in which R is an isopropyl group (—CH(CH$_3$)$_2$), R' is the isopropyl group (—CH(CH$_3$)$_2$) and R" is a trityl group. The invention also relates to the compound of general formula I known as 16 in which R is an isopropyl group (—CH(CH$_3$)$_2$), R' is the tert-butyl group (—C(CH$_3$)$_3$) and R" is a trityl group. The invention also relates to the compound of general formula I known as 17 in which R is an isopropyl group (—CH(CH$_3$)$_2$), R' is the phenyl group (—C$_6$H$_5$) and R" is a trityl group.

The invention relates to the various compounds of the invention mentioned above in the thiazolidine form. The invention relates more particularly to the compounds I-212 and I-213, the chemical formula of which is given in scheme 5 below.

The invention relates to the compounds of formula I in the free form.

Another subject matter of the present invention is a process for the preparation of the compounds of general formula (I) according to processes analogous to those used in peptide synthesis.

According to a first way of preparing the compounds of the invention, the process according to the invention comprises the following stages:
a) protection of the N-acyl-L-cysteine to provide the N-acyl-S-trityl-L-cysteine compound;
b) coupling of the N-acyl-S-trityl-L-cysteine with the S-acylcysteamine hydrochloride to provide the N-(N-acyl-S-trityl-L-cysteinyl)-S-acylcysteamine compound.

Still according to a first way of preparing, the compounds of the invention in thiazolidine form can be prepared according to the process which comprises the following stages:
a) protection of the N-acyl-L-cysteine to provide the N-acyl-S-trityl-L-cysteine compound; then
b) coupling of the protected N-acyl-S-trityl-L-cysteine with thiazolidine;

The compounds thus obtained can be subjected to the following stages of:
c) deprotection of said compound obtained in the preceding stage b), then
d) releasing the free thiol of formula (I).

Thus, according to a preferred embodiment, the process for the preparation of compounds of the invention comprises the stages of:
a) protection of the N-acyl-L-cysteine to provide the N-acyl-S-trityl-L-cysteine compound;
b) coupling of the N-acyl-S-trityl-L-cysteine with the S-acylcysteamine hydrochloride to provide the N-(N-acyl-S-trityl-L-cysteinyl)-S-acylcysteamine compound;
c) S-detritylation reaction of the N-(N-acyl-S-trityl-L-cysteinyl)-S-acylcysteamine compound, in solution of methanol and chloroform, with a mixture of silver nitrate, pyridine and methanol to provide the corresponding silver sulfide;
d) suspending said corresponding silver sulfide in chloroform and then releasing of the free thiol in the presence of HCl or H$_2$S.

More particularly, the preparation of the compound I-152 of the invention can be carried out by the preceding process; to do this, said N-acyl-S-trityl-L-cysteine compound of stage a) is N-acetyl-S-trityl-L-cysteine and said S-acylcysteamine hydrochloride of stage b) is S-acetylcysteamine hydrochloride.

An additional S-acylation stage can be attached to the preceding process for the preparation of compounds according to the invention.

According to a second embodiment, the process according to the invention, suitable for the preparation of the compound of general formula I in which R═R' and R" is a hydrogen, comprises the following stages:

a) esterification of the carboxyl functional group of N-Boc-L-serine (1) with N-hydroxysuccinimide in N,N-dimethylformamide (DMF) in the presence of 1,3-dicyclohexylcarbodiimide (DCC) to form the active ester (1'); then,
b) in situ condensation of the active ester formed (1') with ethanolamine (2) to provide the compound N—(N-Boc-L-seryl)-2-aminoethanol (3); then,
c) Mitsunobu reaction on the compound (3) with triphenylphosphine and diisopropyl azodicar-boxylate in the presence of thiocarboxylic acid in tetrahydrofuran to provide the compound N—(N-Boc-S-acyl-L-cysteinyl)-S-acylcysteamine (4); in the context of the preparation of the compound I-512, the thiocarboxylic acid is thioacetic acid; then,
d) deprotection of the compound (4) with trifluoroacetic acid.

In a specific embodiment, the invention relates to two processes for the preparation of the compound I-152.

The first process for the preparation of the compound I-152 (scheme 1) corresponds to the process for the preparation of the compound of general formula (I) described above and involves correctly protected L-cysteine. This preparation process is characterized in that it comprises the following stages (i) of coupling of N-acetyl-S-trityl-L-cysteine (7) with S-acetylcysteamine hydrochloride to provide the compound N-(N-acetyl-S-trityl-L-cysteinyl)-S-acetylcysteamine (8); then (ii) of S-detritylation reaction of the compound N-(N-acetyl-S-trityl-L-cysteinyl)-S-acetylcysteamine, in solution in methanol and chloroform, with a mixture of silver nitrate, pyridine and methanol to provide the corresponding silver sulfide (9); then (iii) of suspending said corresponding silver sulfide in chloroform; then (iv) of release of the free thiol in the presence of HCl or H₂S.

Scheme 1: Route 1.

Method A: Coupling, via a mixed anhydride formed in situ, of N-acetyl-S-trityl-L-cysteine (7) with S-acetylcysteamine hydrochloride; Method B.: same coupling reaction, via an activated ester formed in situ, of 7. (b) S-detritylation with formation of the corresponding silver sulfide. (c) Release of the free thiol.

Method A is based on the formation, in situ, of a mixed anhydride by reaction of 7 with isobutyl chloroformate in AcOEt in the presence of N-methylmorpholine (NMM). The anhydride is subsequently condensed with S-acetylcysteamine, released from its hydrochloride by NMM, to provide a8 with a yield, after treatments;, of 55%.

Method B uses, in situ, the N-succinimidyl active ester of 7 which, after condensation with S-acetylcysteamine, released from its hydrochloride by NMM, makes it possible to obtain 8 with a yield, after treatments, of 70%. The active ester was formed by reaction of the preceding mixed anhydride (method A) with N-hydroxysuccinimide in AcOEt.

The compound 8, in solution in methanol and chloroform, is subsequently S-detritylated by treatment with a mixture composed of silver nitrate, pyridine and methanol to provide the corresponding silver sulfide 9. This sulfide, which can be isolated, is then suspended in CHCl₃ and then HCl (the use of H₂S leads to the same result) is added to release the free thiol I-152.

The second process for the preparation of the compound I-152 (scheme 2) uses L-serine, N-protected by a t-butoxycarbonyl (Boc) (1), as starting material.

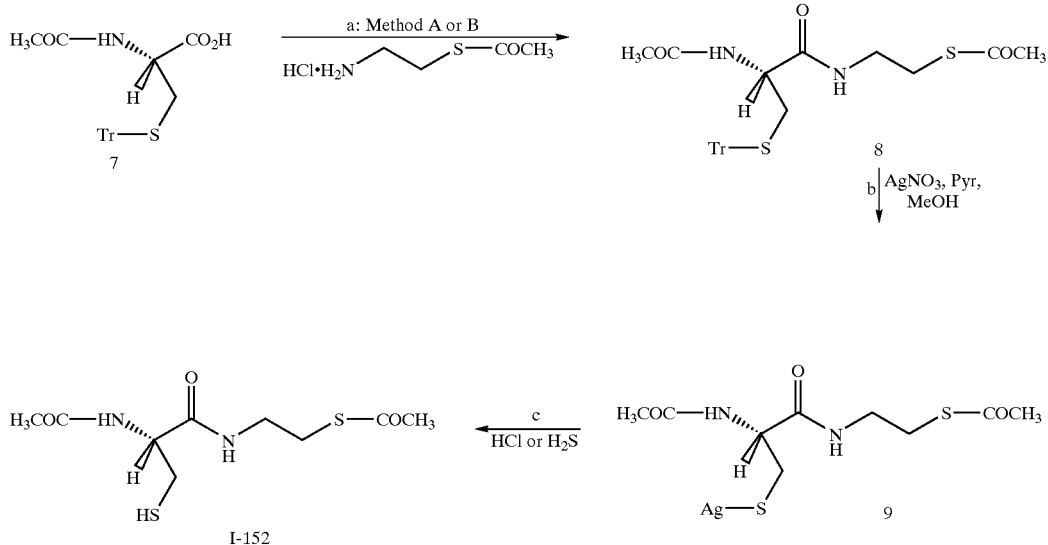

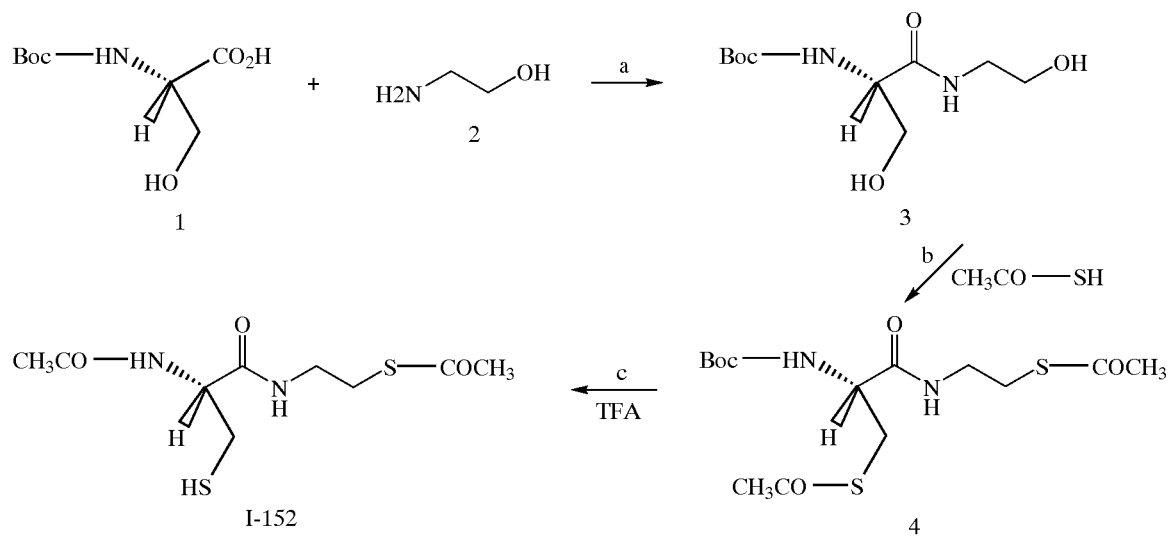

Scheme 2: Route 2. (a) Coupling of N-Boc-L-serine, via an activated ester formed in situ, with ethanolamine. (b) Mitsunobu reaction, with a thioacid, on the primary alcohols with conversion to the L-cysteine series. (c) Deprotection of the amine and S→N transfer of the acyl group.

This process is characterized in that it comprises the following stages (i) of activation of the carboxyl functional group of N-Boc-L-serine (1) by N-hydroxysuccinimide in DMF in the presence of DCC; then (ii) of in situ condensation of the active ester formed (1') with ethanolamine (2) to provide the compound N-(N-Boc-L-seryl)-2-aminoethanol (3); then (iii) of treatment according to a Mitsunobu reaction, modified by R. P. Volante (*Tetrahedron Lett.*, 1981, 22, 3119–3122), of N-(N-Boc-L-seryl)-2-aminoethanol with triphenylphosphine and diisopropyl azodicarboxylate in the presence of thioacetic acid in tetrahydrofuran (THF) to provide the compound N-(N-Boc-S-acetyl-L-cysteinyl)-S-acetylcysteamine (4). Thus, the fact of converting the alcohol of the L-serine into thioester, while retaining the configuration of the asymmetric carbon, made possible conversion to the L-cysteine series; then (iv) of deprotection of N-(N-Boc-S-acetyl-L-cysteinyl)-S-acetylcysteamine with TFA; conventional deprotection of the N-Boc of 4 with TFA does not make it possible to isolate the corresponding amine formed 5, which is unstable under our operating conditions, but it makes it possible to synthesize the compound I-152 by an intramolecular S→N transfer reaction of the acetyl group of 5 via the corresponding thiazoline 6 (scheme 3). Such transfers, in particular on S-acetylcysteamine, have already been observed and studied (R. E. Barnett et al., and the references cited, *J. Amer. Chem. Soc.*, 1969, 91, 2358–2369). These authors show that the mechanism of transfer involves, under some pH conditions, the formation of an intermediate thiazoline which is subsequently hydrolyzed to generate the N-acetylcysteamine. We find that the formation of I-152 involves the same mechanism since we have isolated and identified the cyclic intermediate 6 which results from the N-deprotection of 4 via 5 (scheme 3).

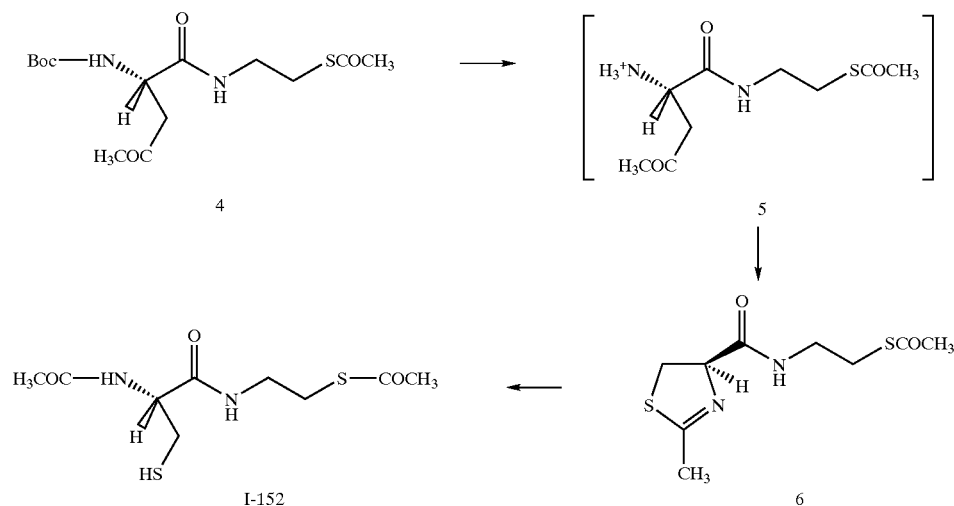

Scheme 3: Formation of I-152 by an intramolecular S→N transfer reaction of the acetyl group of 5 via the corresponding thiazoline 6.

The S→N transfer reaction of the S-acyl on the cysteine residue makes it possible to obtain the compound I-152 under the reaction conditions indicated.

The present invention also relates to a process for the preparation of the compound of general formula I in which R and R' are methyl groups (—CH₃) and R" acyl groups; the preparation is carried out by S-acylation of the compound I-152 in solution in pyridine in the presence of an anhydride $R_2O$ or of an acid chloride R—Cl, characterized in that R is chosen from the CO—$R^1$ group in which $R^1$ is a linear or branched $C_1$–$C_7$ alkyl radical or an aryl group which is unsubstituted or substituted by one or more halogen atoms. Thus, the preparation of the compound I-176 is carried out by S-acylation of the compound I-152, in solution in pyridine, with acetic anhydride. The preparation of the compound I-177 is carried out by S-acylation of the compound I-152, in solution in pyridine, with isobutyryl chloride. The preparation of the compound I-178 is carried out by S-acylation of the compound I-152, in solution in pyridine, with pivaloyl chloride.

More generally, it is an object of the present invention to provide a process for the preparation of acylated analogues of the compound I-152 or of its derivatives (scheme 4) by using method B of the first way of preparing the compound according to the invention described in scheme 1, route 1. This process comprises the stages of:
a) protection of N-acetyl-L-cysteine or N-isobutyryl-L-cysteine to provide N-acetyl-S-trityl-L-cysteine (7) and N-isobutyryl-S-trityl-L-cysteine (13) respectively;
b) various couplings of (7) or (13) with S-acylcysteamine hydrochlorides to provide various corresponding pseudopeptides. Mention should be made, among these, of the compounds 10, 11 and 12, obtained from 7, and the compounds 14, 15, 16 and 17, obtained from 13.

Alternatively, this process for the preparation of analogues of the compound I-152 can be continued by a stage:
c) of S-detritylation reaction, as described above during the preparation of I-152.

Thus, the S-detritylation reactions of the compounds 10, 11 and 12 are carried out to give the corresponding thiol compounds I-188, I-193 and I-198. These compounds can be subjected to a stage:
d) of S-acylation to provide the compounds described above I-189, I-190, I-191, I-192, I-194, I-195, I-196, I-197, I-199, I-200, I-201, I-202.

Thus, the S-acylation reaction of I-188 makes it possible to obtain the compounds I-189, I-190, I-191 and I-192. More particularly, the S-acetylation reaction of I-188 provides I-189, the S-isobutyrylation reaction of I-188 provides I-190, the S-pivaloylation reaction of I-188 provides I-191 and the S-benzoylation reaction of I-188 provides I-192.

Thus, the S-acylation reaction of I-193 makes it possible to obtain the compounds I-194, I-195, I-196 and I-197. More particularly, the S-acetylation reaction of I-193 provides I-194, the S-isobutyrylation reaction of I-193 provides I-195, the S-pivaloylation reaction of I-193 provides I-196 and the S-benzoylation reaction of I-193 provides I-197.

Thus, the S-acylation reaction of I-198 makes it possible to obtain the compounds I-199, I-200, I-201 and I-202. More particularly, the S-acetylation reaction of I-198 provides I-199, the S-isobutyrylation reaction of I-198 provides I-200, the S-pialoyation reaction of I-198 provides I-201 and the S-benzoylation reaction of I-198 provides I-202.

Thus, the S-detritylation reactions of the compounds 14, 15, 16 and 17 are carried out to give the corresponding thiol compounds I-203, I-208, I-214 and I-219. These compounds can be subjected to a stage:
d) of S-acylation to provide the compounds described above I-204, I-205, I-206, I-207, I-209, I-210, I-211, I-215, I-216, I-217 and I-218.

Thus, the S-acylation reaction of I-203 makes it possible to obtain the compounds I-204, I-205, I-206 and I-207. More particularly, the S-acetylation reaction of I-203 provides I-204, the S-isobutyrylation reaction of I-203 provides I-205, the S-pivaloylation reaction of I-203 provides I-206 and the S-benzoylation reaction of I-203 provides I-207.

Thus, the S-acylation reaction of I-208 makes it possible to obtain the compounds I-209, I-210 and I-211. More particularly, the S-acetylation reaction of I-208 provides I-209, the S-isobutyrylation reaction of I-208 provides I-210 and the S-benzoylation reaction of I-208 provides I-211.

Thus, the S-acylation reaction of I-214 makes it possible to obtain the compounds I-215, I-216, I-217 and I-218. More particularly, the S-acetylation reaction of I-214 provides I-215, the S-isobutyrylation reaction of I-214 provides I-216, the S-pivaloylation reaction of I-214 provides I-217 and the S-benzoylation reaction of I-214 provides I-218.

Thus, the S-acylation reaction of I-219 makes it possible to obtain the compounds I-220, I-221, I-222 and I-223. More particularly, the S-acetylation reaction of I-219 provides I-220, the S-isobutyrylation reaction of I-219 provides I-221, the S-pivaloylation reaction of I-219 provides I-222 and the S-benzoylation reaction of I-219 provides I-223.

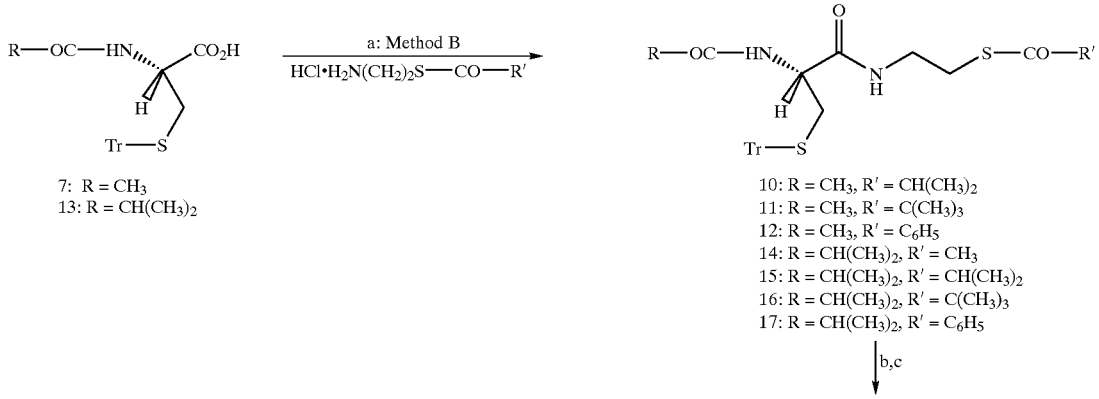

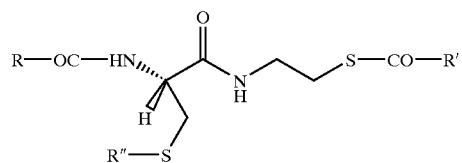
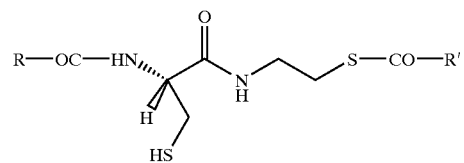

1-189: R = CH₃, R' = CH(CH₃)₂, R" = COCH₃
1-190: R = CH₃, R' = CH(CH₃)₂, R" = COCH(CH₃)₂
1-191: R = CH₃, R' = CH(CH₃)₂, R" = COC(CH₃)₃
1-192: R = CH₃, R' = CH(CH₃)₂, R" = COC₆H₅
1-194: R = CH₃, R' = C(CH₃)₃, R" = COCH₃
1-195: R = CH₃, R' = C(CH₃)₃, R" = COCH(CH₃)₂
1-196: R = CH₃, R' = C(CH₃)₃, R" = COC(CH₃)₃
1-197: R = CH₃, R' = C(CH₃)₃, R" = COC₆H₅
1-199: R = CH₃, R' = C₆H₅, R" = COCH₃
1-200: R = CH₃, R' = C₆H₅, R" = COCH(CH₃)₂
1-201: R = CH₃, R' = C₆H₅, R" = COC(CH₃)₃
1-202: R = CH₃, R' = C₆H₅, R" =COC₆H₅
1-204: R = CH(CH₃)₂, R' = CH₃, R" = COCH₃
1-205: R = CH(CH₃)₂, R' = CH₃, R" = COCH(CH₃)₂
1-206: R = CH(CH₃)₂, R' = CH₃, R" = COC(CH₃)₂
1-207: R = CH(CH₃)₂, R' = CH₃, R" =COC₆H₅
1-209: R = CH(CH₃)₂, R' = CH(CH₃)₂, R" = COCH₃
1-210: R = CH(CH₃)₂, R' = CH(CH₃)₂, R" = COCH(CH₃)₂
1-211: R = CH(CH₃)₂, R' = CH(CH₃)₂, R" = COC₆H₅
1-215: R = CH(CH₃)₂, R' = C(CH₃)₃, R" = COCH₃
1-216: R = CH(CH₃)₂, R' = C(CH₃)₃, R" = COCH(CH₃)₂
1-217: R = CH(CH₃)₂, R' = C(CH₃)₃, R" = COC(CH₃)₃
1-218: R = CH(CH₃)₂, R' = C(CH₃)₃, R" = COC₆H₅
1-220: R = CH(CH₃)₂, R' = C₆H₅, R" = COCH₃
1-221: R = CH (CH₃)₂, R' = C₆H₅, R" = COCH(CH₃)₂
1-222: R = CH(CH₃)₂, R' = C₆H₅, R" = COC(CH₃)₃
1-223: R = CH(CH₃)₂, R' = C₆H₅, R" =COC₆H₅

1-188: R = CH₃, R' = CH(CH₃)₂
1-193: R = CH₃, R' = C(CH₃)₃
1-198: R = CH₃, R' = C₆H₅
1-203: R = CH(CH₃)₂, R' = CH₃
1-208: R = CH(CH₃)₂, R' = CH(CH₃)₂
1-214: R = CH(CH₃)₂, R' = C(CH₃)₃
1-219: R = CH(CH₃)₂, R' = C₆H₅

Scheme 4: Preparation of acylated analogues of I-152 or of its derivatives by using method B described in scheme 1, route 1.

As regards the compounds of the invention in the thiazolidine form, the latter are preferably obtained by coupling N-acyl-S-trityl-L-cysteine with thiazolidine according to method A described in scheme 1, route 1. The invention relates more particularly to the compounds I-212 and I-213 which can be obtained by the process described in scheme the preparation of I-152, makes it possible to generate a free thiol known as I-212. The preparation of the compound I-213 is carried out by S-acetylation of I-212. The three coupling products (18, I-212 and I-213) were respectively isolated in the form of a mixture of two conformational isomers. These isomers are due to the presence of the carbonyl of the pseudopeptide bond alpha to the nitrogen atom of the thiazolidine.

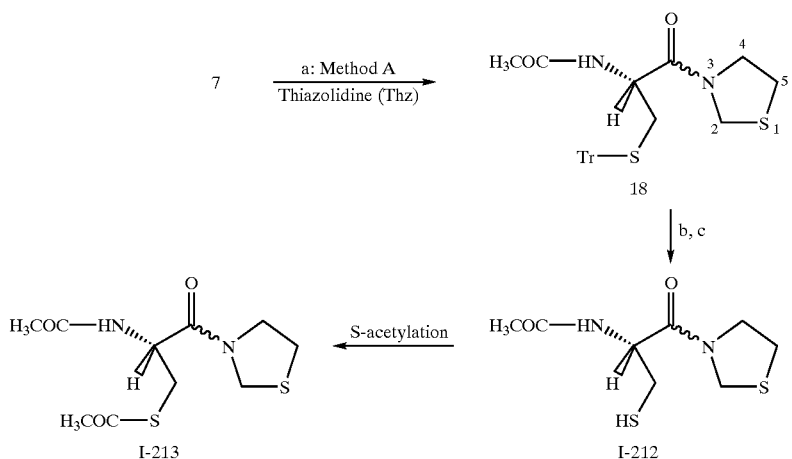

5. In this case, N-acetyl-S-trityl-L-cysteine (7) was coupled according to method A, scheme 1: route 1) with thiazolidine to form the compound 18. The S-detritylation of the latter according to the protocol described above, in particular for Scheme 5: Preparation of N-(N-NAC)-thiazolidine and of its acetylated derivative via method A described in scheme 1, route 1.

All the compounds of the invention exhibit a common characteristic; they are precursors of compounds which are involved in the route for the biosynthesis of glutathione. In other words, these compounds can be used as intermediates which are involved in the route for the biosynthesis of glutathione. It can relate, for example, to a product chosen from the group formed by NAC, MEA and L-cysteine.

The compounds of the invention exhibit an antioxidant activity. Another subject matter of the invention is therefore the use of the compounds as described above as antioxidant agents; such compounds have a wide range of uses, such as use in the preventive and curative treatment of pathological syndromes for which an oxidative stress and a GSH deficit are observed, uses in cosmetology or uses in the farm-produce industry.

The invention is targeted at providing antioxidant agents for combating oxidative stress and for increasing the intracellular level of glutathione. The compounds of the present invention can be used as medicament, in particular for increasing the intracellular and/or extracellular level of glutathione. The invention also covers the use of a compound according to the invention in the preparation of a medicament intended to increase the intracellular and/or extracellular level of glutathione. The present invention also relates to a pharmaceutical composition, characterized in that it comprises an effective amount of a compound according to the invention and a pharmaceutically acceptable vehicle. The invention also relates to the use of a compound according to the invention in the preparation of a medicament or of a pharmaceutical composition for the treatment and/or prevention of pathologies or disorders related to an intra- and/or extracellular depletion of glutathione.

The pathologies which can form the subject of a prophylaxis or of a treatment by the compounds of the invention are in particular viral infections, bacterial infections, parasitic infections, diseases of the respiratory tract, neurodegenerative diseases, autoimmune diseases, cardiovascular diseases, cancers, diseases of the immune system, diabetes and preferably type I diabetes, ophthalmic pathologies or dermatological diseases.

The invention relates more particularly to the use of a compound as described above in the preparation of a medicament or of a pharmaceutical composition for the treatment and/or prevention of viral infections; they are in particular viral infections caused by DNA viruses and RNA viruses and more particularly by retroid viruses, more particularly the human immunodeficiency virus (HIV) and preferably the type-1 human immunodeficiency virus (HIV-1). Infection by the HIV is responsible for acquired immunodeficiency syndrome (AIDS), which constitutes a human pathology in which oxidizing agents play an important role. AIDS has constituted a public health problem in many countries in the world since 1981, the date at which the disease was identified for the first time. When AIDS is declared, death generally follows two to three years after diagnosis as a result of the collapse of the immune defenses of the patient and of multiple opportunistic infections. During infection by the HIV, a decrease in the cell and plasma levels of antioxidant molecules is observed. This immune disruption, christened "oxidative stress", is critical for the patient. It seems to play a major role in the physiopathology of infections by the HIV by enhancing viral replication, the inflammatory syndrome, apoptosis, loss in weight of the patients (cachexia) and poisoning by medicaments. While the mechanisms contributing to this oxidative stress are poorly understood, it seems probable that the chronic inflammatory syndrome associated with HIV infections accentuates it. Likewise, the HIV, via the Tat protein, seems itself to play a major role. This is because this protein blocks the production and secretion of manganese superoxide dismutase (MnSOD), an enzyme which can prevent oxidative stress, and greatly decreases the activity of glucose-6-phosphate dehydrogenase (G6PD), an enzyme necessary for the maintenance of glutathione in its reduced form.

In individuals infected by the HIV, thiols and very particularly GSH are decreased in the plasma and the peripheral blood mononuclear cells (PBMCs). Attacks occur both in the blood and in the tissues, since the GSH deficit is found in the bronchoalveolar lavages and in the central nervous system (CNS). These twofold localizations first confirm that the two major targets of HIV, the lymphocytes and the macrophages, are affected and, secondly, illustrate the scale of the deficit. This can probably explain, at the very least in part, the results published by L. A. Herzenberg et al. (*Proc. Natl. Acad. Sci.*, 1997, 94, 1967–1972). These authors show the existence of a direct connection between patient survival and the GSH level.

Current antiretroviral therapy is based on two families of molecules, reverse transcriptase (RT) inhibitors, (AZT, ddI, nevirapine, and the like) and viral protease inhibitors (indinavir, saquinavir, and the like). They have a degree of in vivo activity when they are combined with one another. However, these molecules are incapable of fully reorganizing affected tissues, such as, for example, those affected by inflammatory and oxidative syndromes in the CNS, and have a reduced or zero effectiveness with respect to pathologies associated with infection by the HIV. In view of the major role of GSH in the control of these two syndromes and of its plurality of effects in the physiopathology of HIV infections, numerous alternatives targeted at raising its intracellular level have been envisaged without success as adjuvant therapeutic strategy in recent years.

The unremitting spread of infections by the HIV virus and of the associated opportunistic infections makes it necessary to have available an effective treatment against AIDS and of the associated affected tissues. One of the aims of the present invention is thus to use the compounds corresponding to the general formula (I), preferably the compounds I-152 and/or I-176 and/or I-177 and/or I-178, in the preparation of a medicament or of a pharmaceutical composition for the treatment and/or prevention of viral infections brought about by the human immunodeficiency virus (HIV) and more particularly the type-1 human immunodeficiency virus. (HIV-1). The present invention also provides a pharmaceutical composition for the preventive and curative treatment of AIDS and the associated affected tissues, characterized in that it comprises a therapeutically effective amount of a compound according to the invention and a pharmaceutically acceptable vehicle. The present invention also relates to a product comprising at least one compound according to the invention and at least one reverse transcriptase inhibitor and/or as combination product for a use in antiviral therapy which is simultaneous, separate or spaced out over time. The reverse transcriptase inhibitor is chosen, for example, from 3'-azido-3'-deoxythymidine (AZT), 2',3'-dideoxyinosine (ddI), 2',3'-dideoxycytidine (ddC), (–)-2',3'-dideoxy-3'-thiacytidine (3TC), 2',3'-didehydro-2',3'-dideoxythymidine (d4T) and (–)-2'-deoxy-5-fluoro-3'-thiacytidine (FTC), TIBO, HEPT, TSAO, α-APA, nevirapine, BAHP or phosphonoformic acid (PFA). The viral protease inhibitor is chosen more particularly from indinavir and saquinavir.

It is also within the scope of the invention to use the compounds corresponding to the general formula (I), preferably the compounds I-152 and/or I-176 and/or I-177 and/or I-178, in the preparation of a medicament or of a pharmaceutical composition for the treatment and/or prevention of cardiovascular diseases preferably chosen from the group consisting of arterial hypertension, arteriosclerosis, cerebral ischemia, cardiac ischemia, ventricular arrhythmias, ventricular fibrillation and myocardial infarction. This is because patients affected by arterial hypertension treated with organic nitrates frequently develop resistance to the effects of these drugs. It has been suggested that this tolerance is associated, among factors, with the depletion of thiol groups in the vascular smooth muscles. It has been demonstrated that metabolic precursors of glutathione, such as NAC, prevent the development of tolerance or at least restore the effects of the organic nitrates (Abrams 1991, Horowitz 1991, Bosegaard et al. 1993). The present invention thus proposes to provide novel compounds for preventing the development of tolerance or at least restoring the effects of the organic nitrates used in the treatment of arterial hypertension. Heller et al. (1997) have experimentally demonstrated the action of various reactive oxygen species in the inflammation of the islets of Langerhans and in the destruction of the β cells. It is thus an object of the present invention to provide novel compounds for the treatment and prevention of type-I diabetes (IDDM) (Rabinovitch et al., 1992).

Oxidative stress and GSH deficit are also involved in other pathologies. Thus, in the field of ophthalmology, they can be related to the appearance of cataracts. It is thus within the scope of the invention to use the compounds corresponding to the general formula (I), preferably the compounds I-152 and/or I-176 and/or I-177 and/or I-178, in the preparation of a medicament or of a pharmaceutical composition for the treatment and/or prevention of ophthalmic pathologies, such as the ocular effects of Sjogren's syndrome and cataracts.

It is also within the scope of the invention to use the compounds corresponding to the general formula (I), preferably the compounds I-152 and/or I-176 and/or I-177 and/or I-178, in the preparation of a medicament or of a pharmaceutical composition for the treatment and/or prevention of diseases of the respiratory tract, in particular pulmonary emphysema, idiopathic pulmonary fibrosis, cystic fibrosis, chronic bronchitis, acute bronchitis or adult respiratory distress syndrome.

The invention also relates to the use of a compound as described above in the preparation of medicaments intended for the preventive and/or curative treatment of noise-related hearing loss.

The invention also relates to the use of a compound as described above in the preparation of medicaments intended for the treatment of poisoning related to the oral or parenteral administration, as or not as an overdose, of substances preferably chosen from the group consisting of acetaminophen, nitrites, ethanol, acrylonitrile and heavy metals, more particularly gold, silver and mercury.

The antioxidant properties of the compound of the invention recommend it for use in the field of cosmetics. This is because antioxidants are already used in cosmetology to slow down aging. The compounds of the present invention are capable of promoting the rebuilding of the cell content of GSH and of providing effective protection against cell damage caused by extrinsic and intrinsic toxic factors; the skin is the site of attack by these factors. The extrinsic factors include, for example, ultraviolet radiation, wind, low humidity, abrasives and strong surface-active agents. The intrinsic factors include chronological aging and biochemical modifications of the skin. Whether extrinsic or intrinsic, these factors lead to the appearance of wrinkles and other histological changes associated with aging of the skin. The antiwrinkle agents currently known include compounds such as N-acetyl-L-cysteine, retinoids, such as retinoic acid, and alpha-hydroxy acids, such as glycolic acid and lactic acid. It is thus one of the objects of the invention to use the antioxidant properties of the compounds according to the invention to (i) prevent, erase and treat wrinkles or fine lines of the skin; and/or (ii) combat cutaneous and/or subcutaneous slackening; and/or (iii) improve the texture of the skin and rekindle the radiance of the skin; and/or (iv) remove undesired hairs from the skin; and/or (v) decrease the sizes of the pores of the skin; and/or (vi) permanently deform the hair. As regards the final point, it should be pointed out that organic molecules carrying thiol functional groups, such as the compounds according to the invention, are products having multiple applications. One of these applications is the permanent deformation (curling and straightening) of the hair, which consists, in a first step, in opening the disulfide bonds (S—S) of the cystine units of the keratin using a composition comprising at least one organic compound carrying a thiol functional group which acts as reducing agent (reduction stage), which makes it possible to confer the desired shape on the hair; then, after having rinsed the hair, in reconstituting, in a second step, said disulfide bonds by applying, to the hair, an oxidizing composition (oxidation or fixation stage), so as to fix the hair in the shape which has been given to it. The invention thus relates to a cosmetic composition for the treatment of the skin and/or hair and/or body hairs, characterized in that it comprises a compound according to the invention and a cosmetically acceptable excipient. The invention also relates to a process for the cosmetic treatment of the skin for preventing, erasing and treating wrinkles or fine lines of the skin and/or combating cutaneous and/or subcutaneous slackening and/or improving the texture of the skin and rekindling the radiance of the skin and/or removing undesired hairs from the skin and/or decreasing the sizes of the pores of the skin which comprises the application, to the skin, of a cosmetic composition as described above.

The antioxidant properties of the compound of the invention recommend it for use in the farm-produce field. It is thus within the scope of this invention to use the compounds of the invention as antioxidant agents for the preservation of the organoleptic and nutritional properties of drinks, in particular fruit juices, and food.

Other characteristics and advantages of the present invention will be more clearly demonstrated on reading the following examples: in these examples, reference will be made to the following figures:

FIG. 1: Probable decomposition of I-152.

Figure 2:
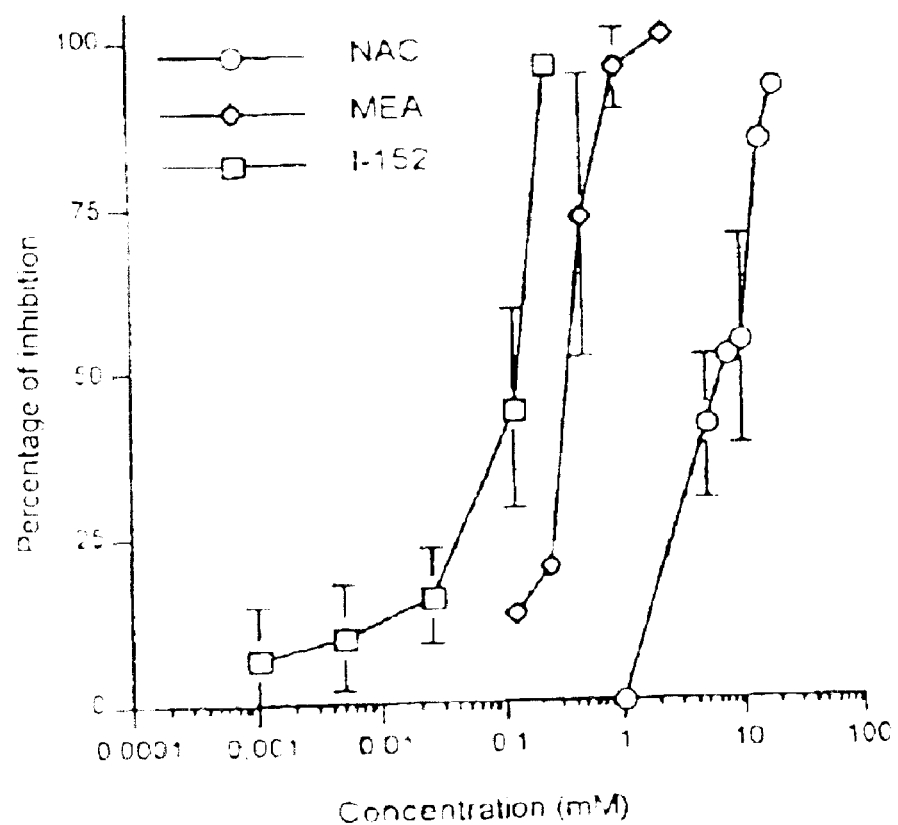

FIG. 2: Comparison of the antiviral activities of NAC, of MEA and of I-152 in MDM cultures infected with 10 000 TCID50s of the HIV-1/Ba-L isolate: effect-doses. The results are expressed according to the mean±standard deviation of the percentages of inhibition. Viral replication was measured by assaying the reverse transcriptase activity in the culture supernatants.

Figure 3:
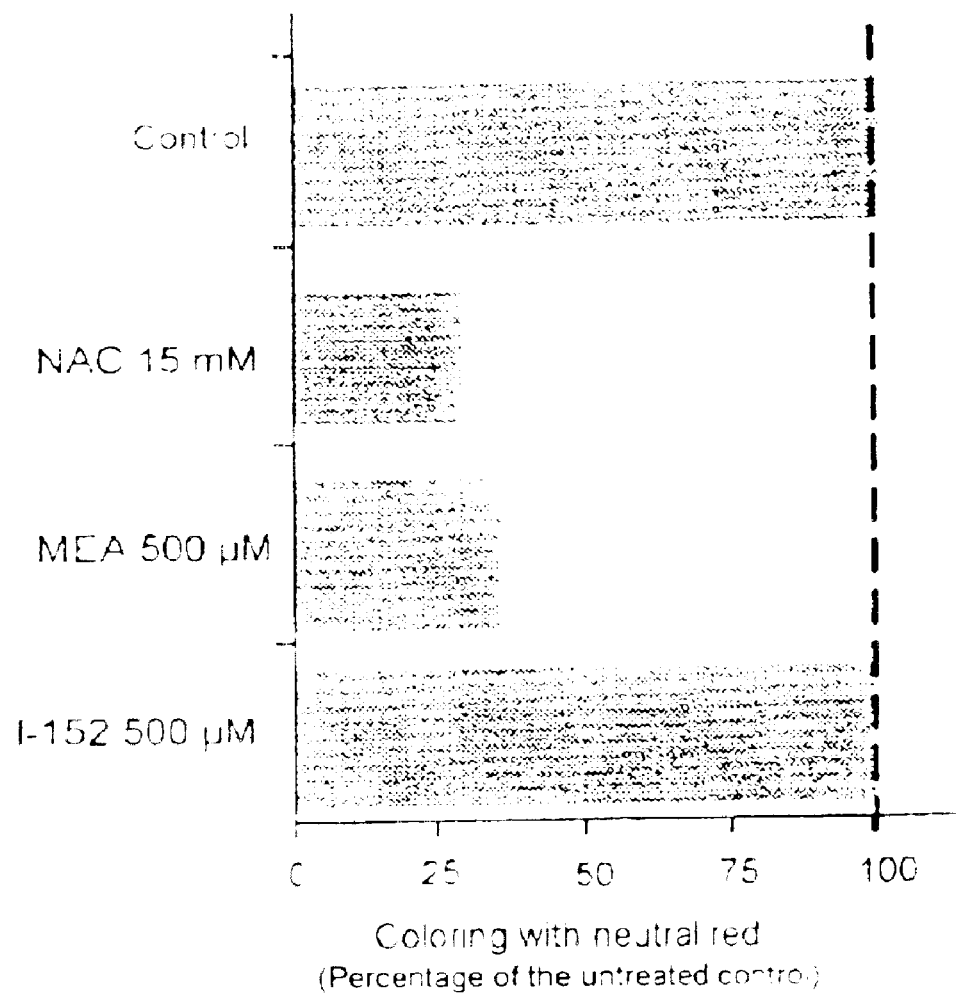

FIG. 3: Cytotoxicity of NAC, MEA and I-152 with respect to MDMs.

Figure 4:
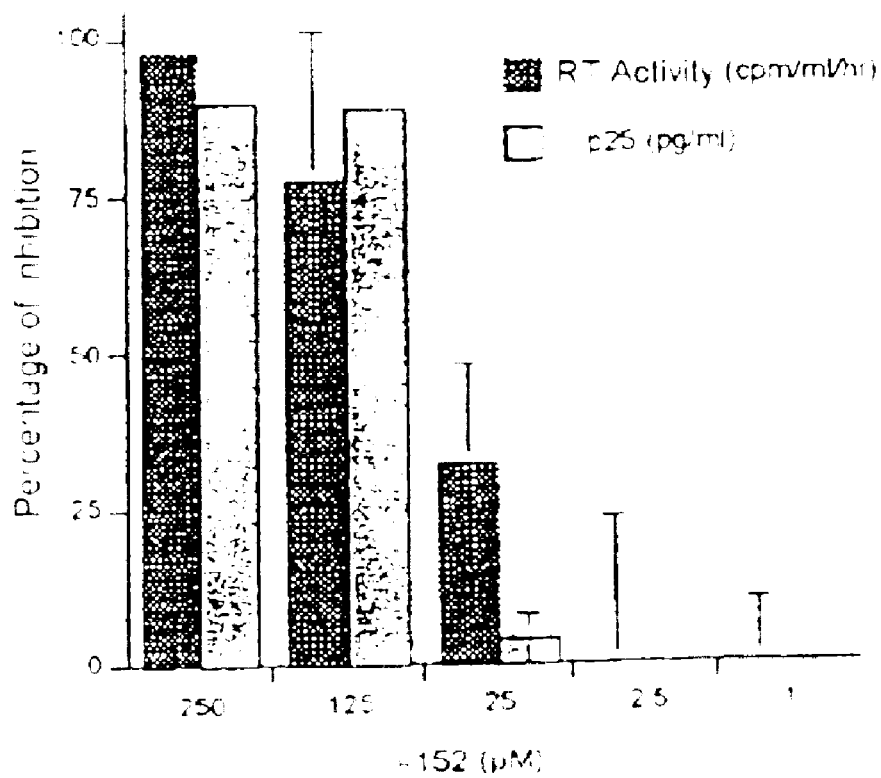

FIG. 4: Measurement of the RT activity and of the production of protein p25 in the MDM culture supernatants infected with the HIV-1/Ba-L strain and treated with I-152.

Figure 5:
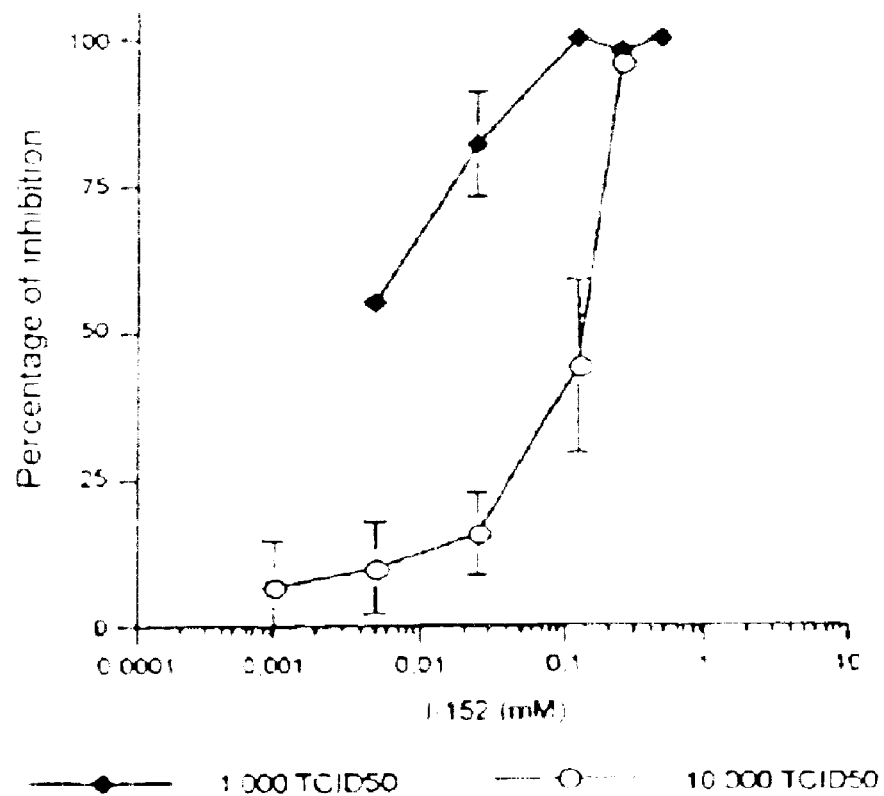

FIG. 5: Effect of the m.o.i. on the antiviral activity of I-152. The MDMs were infected with 1 000 or 10 000 TCID50s of the HIV-1/Ba-L isolate.

Figure 6:
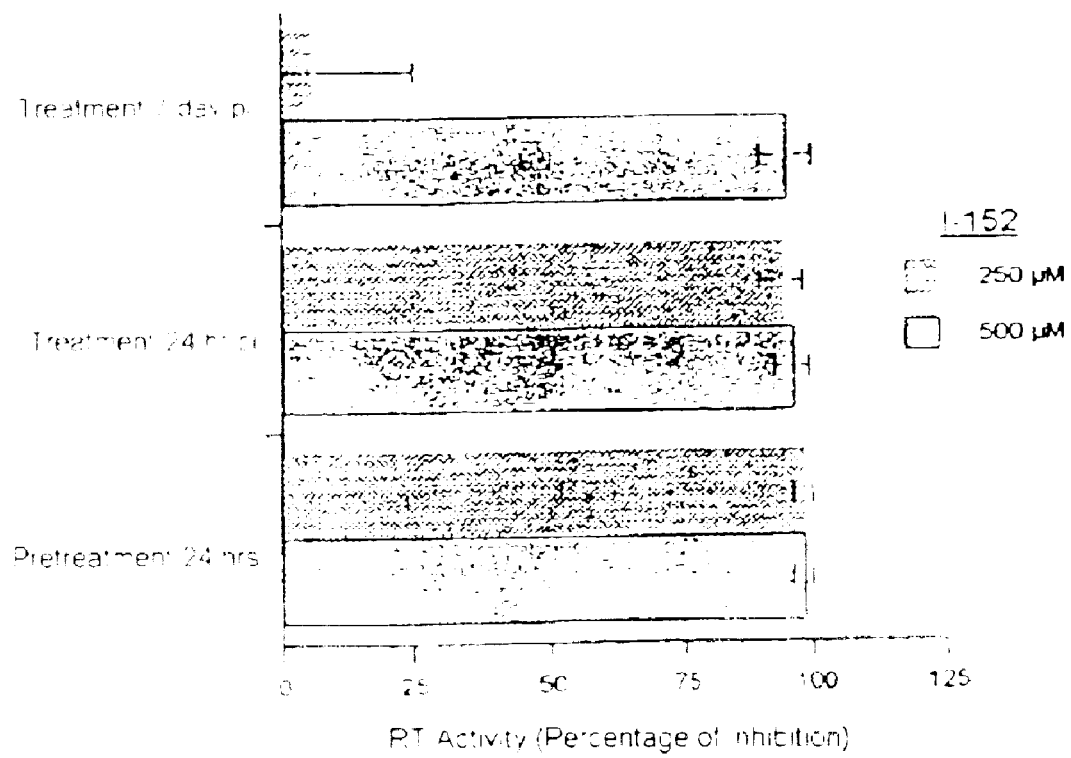

FIG. 6: Effects of I-152 on viral replication according to the treatment method: pretreatment 24 hours, treatment 24 hours after infection, treatment 7 days after infection.

Figure 7:
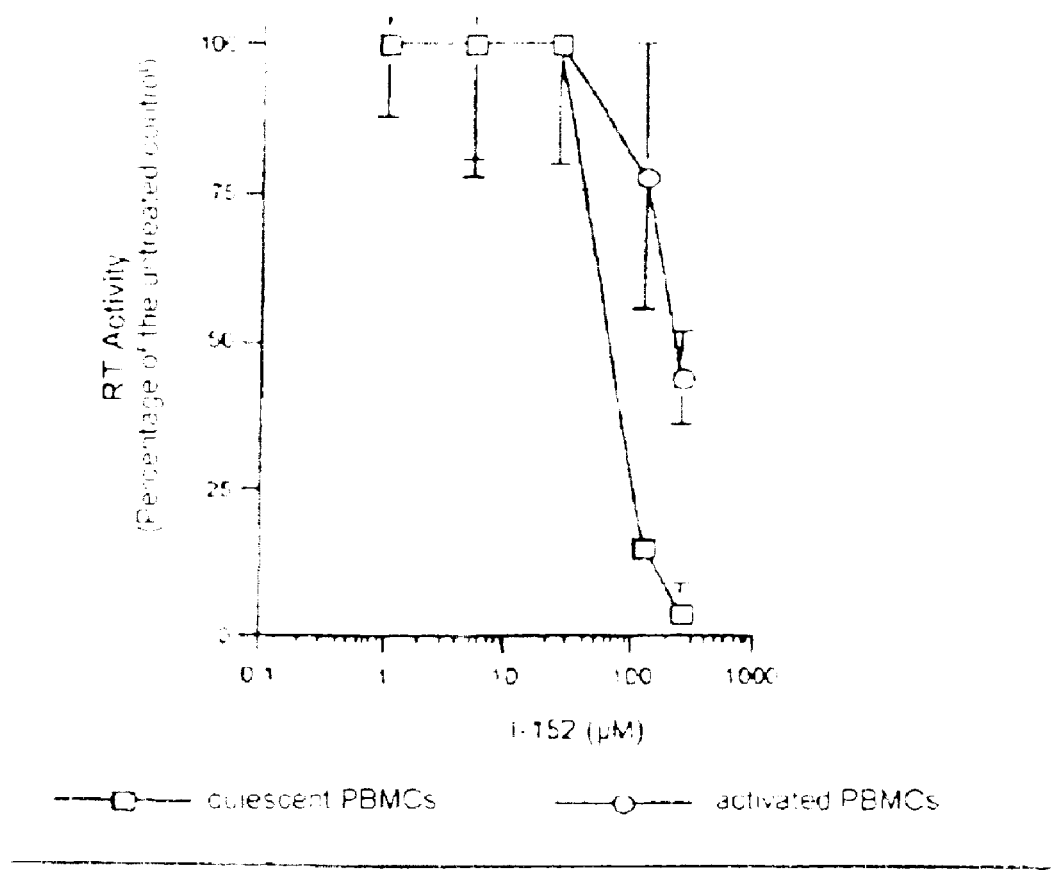

FIG. 7: Antiviral activity of I-152 in quiescent PBMCs or PBMCs activated with PHA-P, and infected with the HIV-1 LAI strain.

Figure 8:
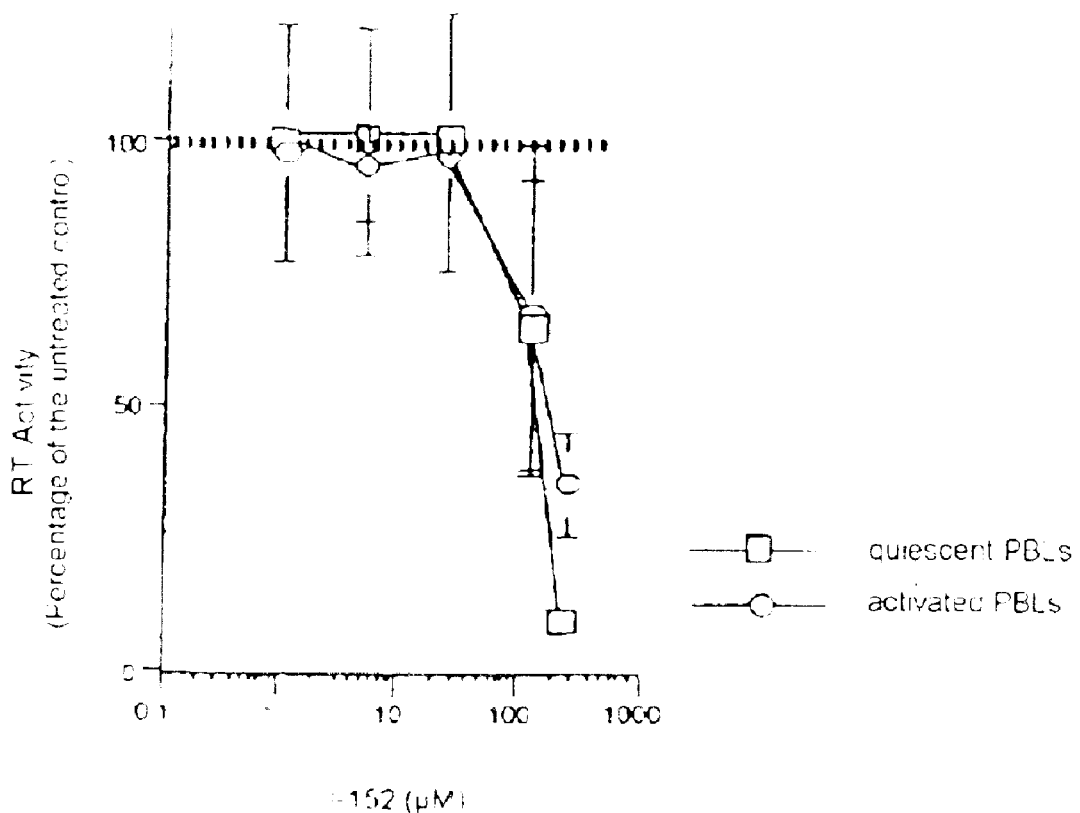

FIG. 8: Antiviral activity of I-152 in quiescent PBLs or PBLs activated with PHA-P, then infected with the HIV-1 LAI strain.

Figure 9:
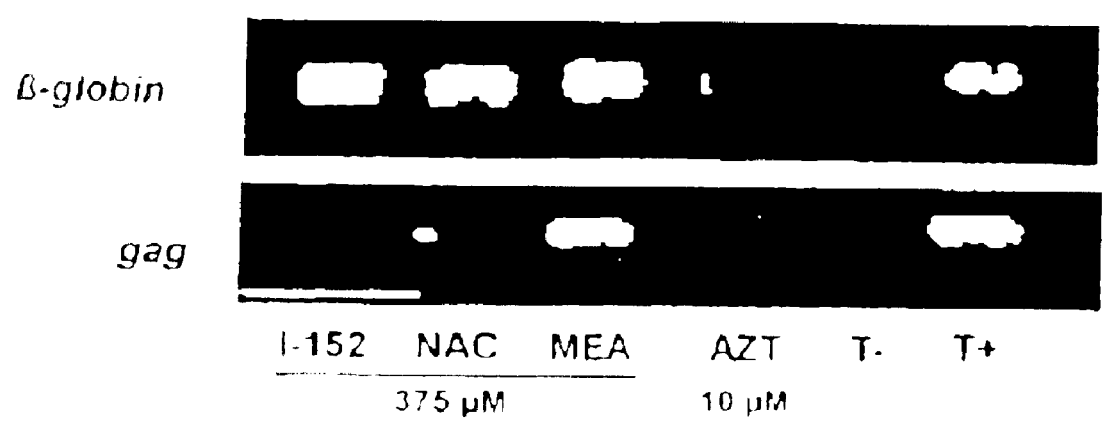

FIG. 9: Effects of I-152 on the integration of the provirus within the cell genome.

Figure 10:
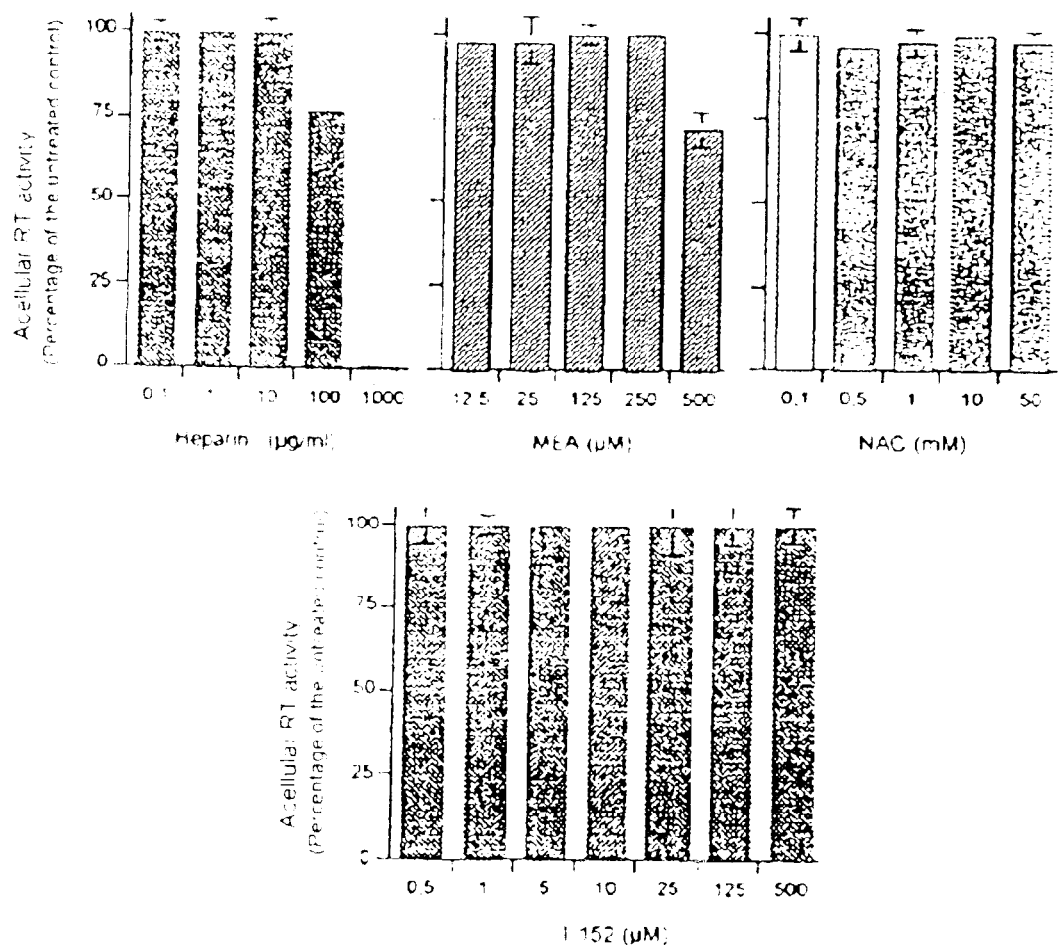

FIG. 10: Effects of I-152 on the enzymatic activity of the RT of the HIV-1. The experiments were carried out in triplicate.

Figure 11:
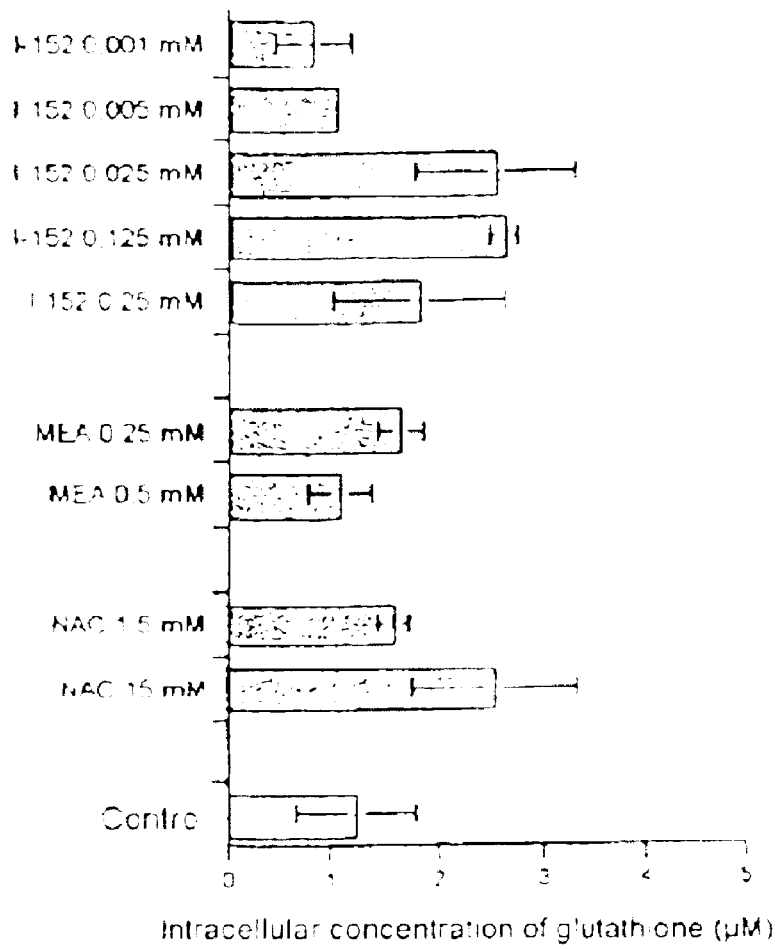

FIG. 11: Assaying of the total intracellular glutathione in quiescent PBMCs, treated 24 hours before with NAC, MEA or I-152.

Figure 12:
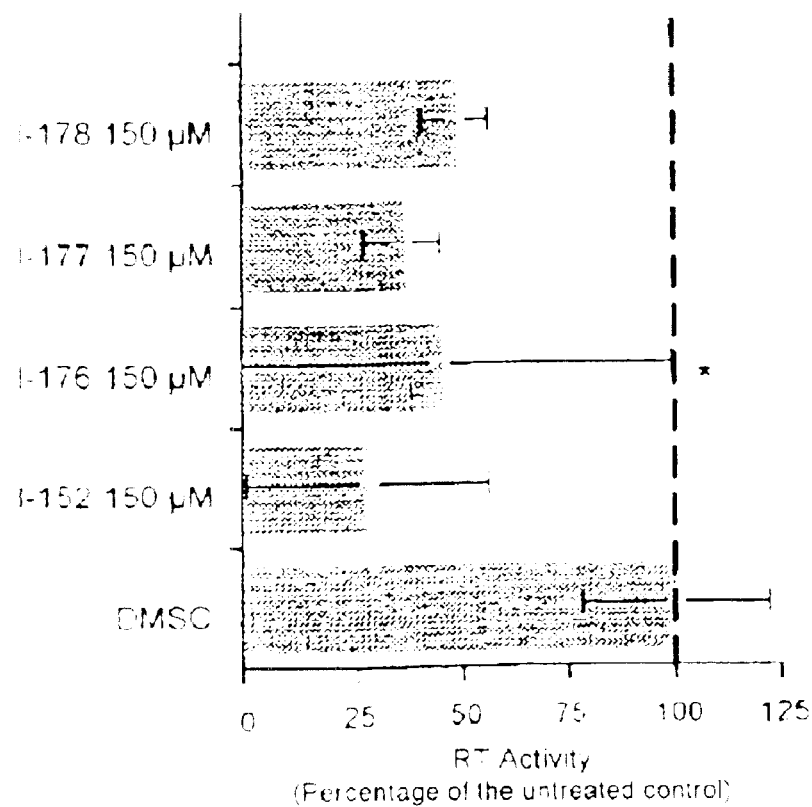

FIG. 12: Antiviral activity-of the I-152 derivatives (I-176 is cytotoxic at the dose tested).

Figure 13:
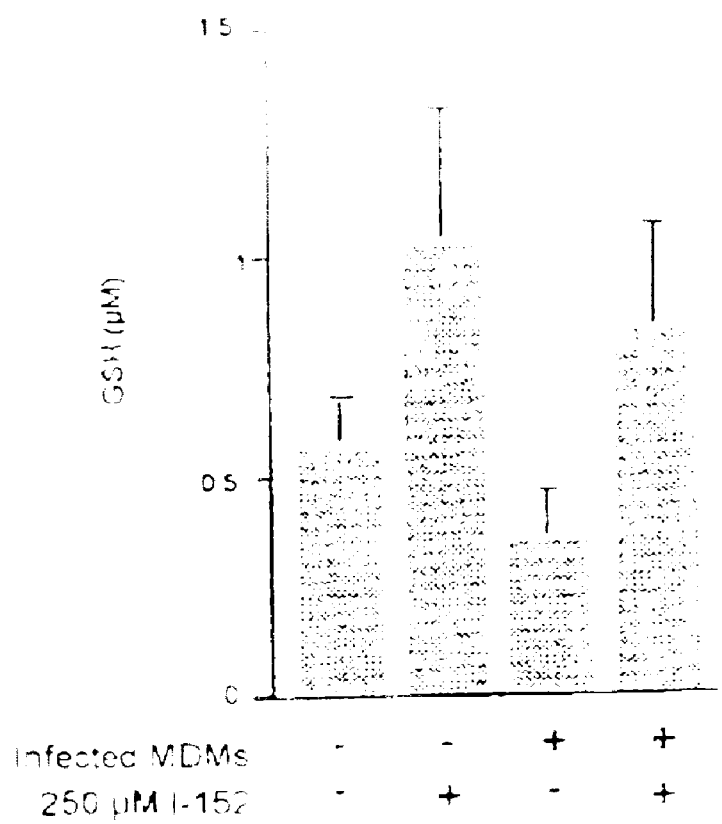

FIG. 13: Intracellular concentration of GSH in MDMs infected or not infected in vitro with the reference strain with macrophage tropism HIV-1/Ba-L, and treated or not treated with the compound I-152.

Figure 14:
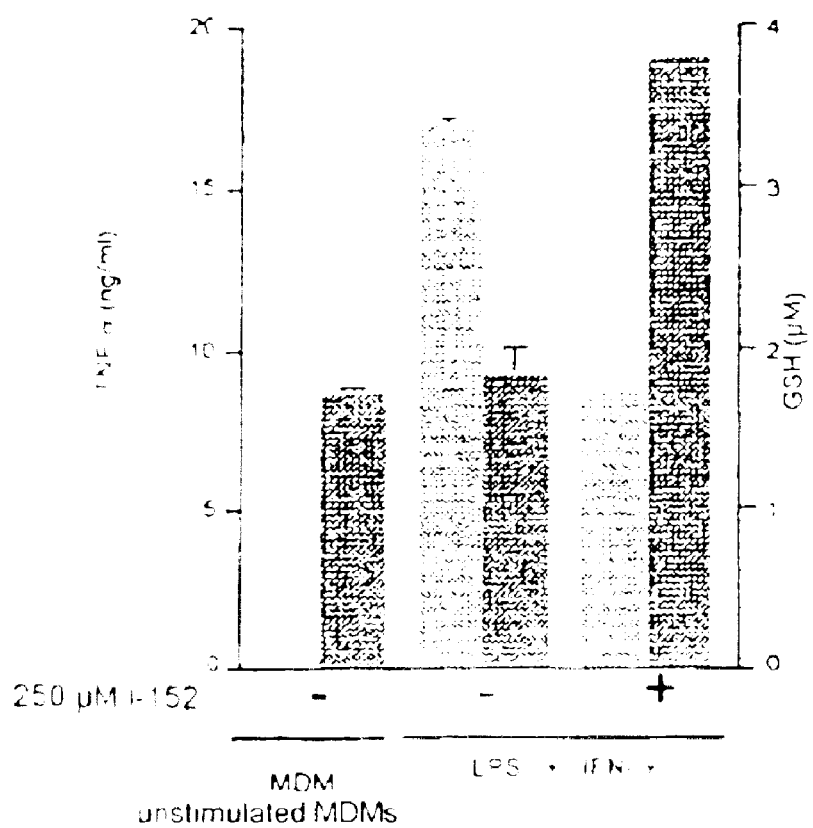

FIG. 14: Effects of the compound I-152 on the intracellular concentration of GSH and the synthesis of TNF-α in MDMs stimulated in vitro with a bacterial lipopolysaccharide (LPS; 1 µg/ml) and IFN-γ (100 IU/ml).

Figure 15:
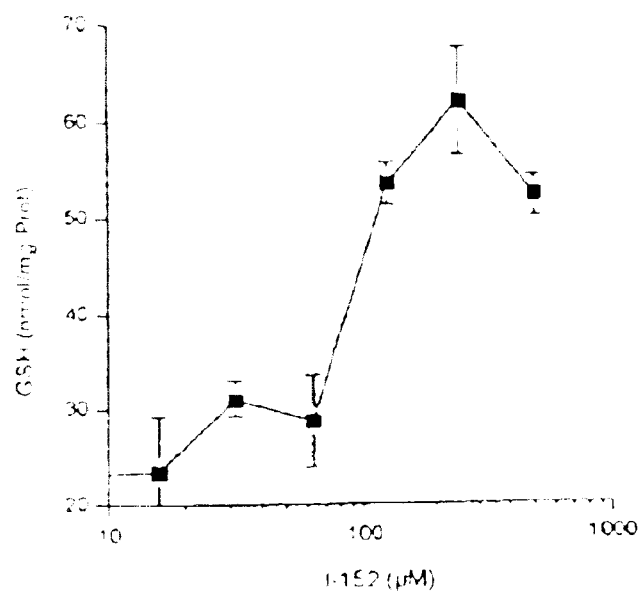

FIG. 15: Intracellular concentration of GSH in spleen macrophages after or not after treatment with I-152. The intracellular concentration of GSH in untreated human spleen macrophages is 22±2 µM.

Figure 16:
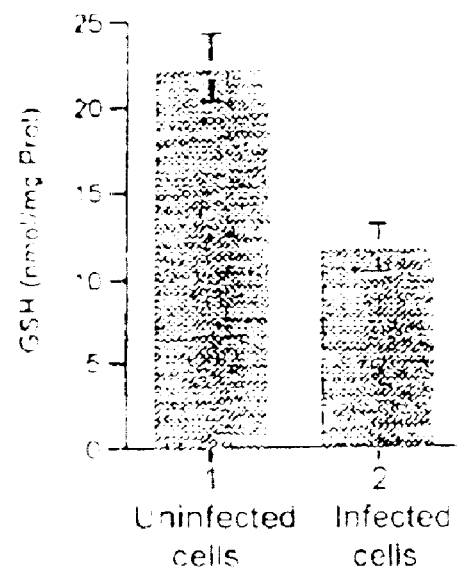

FIG. 16: Intracellular concentration of GSH in spleen macrophages infected or not infected in vitro with the reference strain with macrophage tropism HIV-1/Ba-L.

Figure 17:
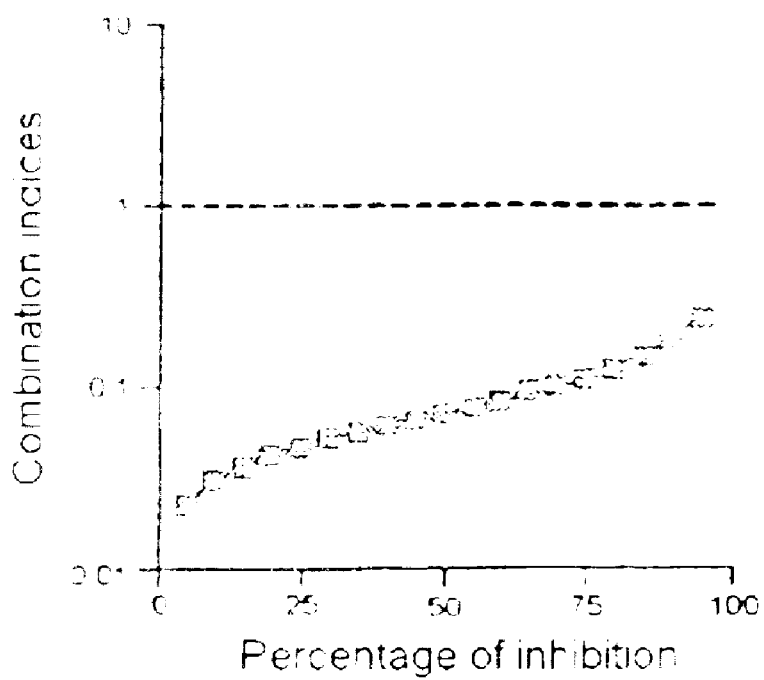

FIG. 17: Effects of I-152 on the anti-HIV activity of AZT in MDMs infected with the HIV-1/Ba-L strain.

Table I: Comparison of the antiviral activities of NAC, MEA and I-152 in MDM cultures infected with 10 000 TCID50s of the HIV-1/Ba-L isolate: 50, 70 and 90% effective doses.

Table II: Effects of the m.o.i. on the antiviral activity of I-152: 50% effective doses.

Table III: Antiviral activity of I-152 in spleen MDMs infected with 10 000 TCID50s of the HIV-1/Ba-L isolate: 50, 70 and 90% effective doses.

Table IV: Comparison of the antiviral activities of I-152 and its S-acylated analogues in MDM cultures infected with 10 000 TCID50s of the HIV-1/Ba-L isolate: 50, 70 and 90% effective doses.

Table V: Comparison of the antiviral activities of I-152 and its variously S-acylated (N-isobutyryl) derivatives in MDM cultures infected with 10 000 TCID50s of the HIV-1/Ba-L isolate: 50, 70 and 90% effective doses.

EXAMPLE 1

Synthesis of N-(N-acetyl-L-cysteinyl)-S-acetylcysteamine (I-152)

1.1 First Route for the Synthesis of I-152 Using S,N-protected L-cysteine:

1.1.1. N-(N-acetyl-S-trityl-L-cysteinyl)-S-acetylcysteamine (8)

a)—Coupling Method Involving in Situ a Mixed Anhydride

A solution comprising 290 mg (0.71 mmol) of N-acetyl-S-trityl-L-cysteine (7, Bachem) and 80 µl (0.72 mmol) of of N-methylmorpholine (NMM) in 5 ml of AcOEt is stirred at −15° C. and then 93 µl (0.71 mmol) of isobutyl chloroformate are added. After stirring for 15 min and while maintaining the starting temperature, 111.4 mg (0.71 mmol) of S-acetylcysteamine hydrochloride (prepared according to T. Wieland and E. Bokelman, *Ann. Chem.*, 1952, 576, 20–34) and then 80 µl (0.72 mmol) of NMM are added. The reaction mixture is maintained at −15° C. for 15 min and then, after returning to room temperature, stirring is continued for 3 h. The NMM hydrochloride formed is filtered off and washed with 2×2.5 ml of AcOEt and the combined organic phases are evaporated to dryness under vacuum. The coupling product is subsequently isolated from the gum obtained by flash chromatography on a silica gel column (eluent: AcOEt/petroleum ether 30%). 198 mg (Yd=55%) of the expected compound are collected. $R_f$ (AcOEt/petroleum ether, 9:1): 0.41. Cystallizes from an AcOEt/petroleum ether mixture in the form of a colorless powder: M.p.=111–113° C. $[\alpha]_D^{20}$=+10.5° (c 0.8, CHCl$_3$).

$^1$H NMR (CDCl$_3$) δ ppm: 1.90 (s, 3H, NCOCH$_3$), 2.29 (s, 3H, SCOCH$_3$), 2.48 (dd, J=5.7, 12.9 Hz, 1H, β Ha cys), 2.82 (dd, J=6.4, 12.9 Hz, 1H, β Hb cys), 2.92–3.01 (m, 2H, NCH$_2$CH$_2$S), 3.32–3.42 (m, 2H, NCH$_2$CH$_2$S), 4.07–4.20 (m, 1H, α H cys), 5.70 (d, J=7.6 Hz, 1H, NH cys), 6.34 (t, J=5.5 Hz, 1H, NHCH$_2$), 7.19–7.35 and 7.40–7.47 (2m, 15H, aromatic H).

MS: (FAB$^+$/NBA+K$^+$) m/z 545 (M+K)$^+$, 507 (M+H)$^+$; (FAB$^-$/NBA) m/z 505 (M−H)$^-$.

| Analysis: $C_{28}H_{30}N_2O_3S_2$ (506) | | | |
|---|---|---|---|
| Calc. %: | C 66.40 | H 5.93 | N 5.53 |
| Found %: | 66.17 | 6.00 | 5.81 | b)—Coupling Method Involving in Situ an Activated Ester

A solution comprising 1.5 g (3.70 mmol) of 7 and 410 µl (3.73 mmol) of NMM in 30 ml of AcOEt is stirred at −15° C. and then 480 µl (3.70 mmol) of isobutyl chloroformate are added. After stirring for 15 min and while maintaining the starting temperature, 426 mg (3.70 mmol) of N-hydroxysuccinimide are added. The reaction mixture is maintained at −15° C. for 15 min and then, after returning to ambient temperature, stirring is continued for 2 h. The NMM hydrochloride formed is filtered off and washed with 2×5 ml of AcOEt. The organic phases comprising the O-N-succinimide active ester of 7 are combined and stirred at −15° C. 575 mg (3.70 mmol) of S-acetylcysteamine hydrochloride and 410 µl (3.73 mmol) of NMM are then successively added to the solution. The reaction mixture is maintained at −15° C. for 15 min and then, after returning to ambient temperature, stirring is continued for 12 h. The solution is subsequently diluted with 300 ml of AcOEt, washed (water, 30 ml; ice-cold saturated sodium bicarbonate, 30 ml; water, 30 ml; ice-cold 0.1N citric acid, 30 ml; water, 3×30 ml), dried over sodium sulfate, filtered and evaporated to dryness under vacuum. The residue obtained is subsequently purified as above to give, with a yield of 70% (1.31 g) and with entirely the same physicochemical criteria, the coupling product 8 described above.

1.1.2. N-(N-acetyl-L-cysteinyl)-S-acetylcysteamine (I-152)

A saturated solution, with the exclusion of light, of 1.26 g (2.49 mmol) of 8 in 20 ml of MeOH and 1.5 ml of CHCl$_3$ is stirred at ambient temperature and a mixture, also with the exclusion of light, comprising 449 mg (2.64 mmol) of silver nitrate and 213 µl (2.64 mmol) of pyridine in 13 ml of MeOH, is added. There is instantaneously formation of a precipitate of the corresponding silver sulfide 9. At the end of the addition, stirring is halted and the reaction mixture is left overnight at ambient temperature. The precipitate is subsequently filtered off and washed with MeOH (2×10 ml) and then with CHCl$_3$ (2×10 ml).

An analytical sample of 9 is withdrawn and is then dried under vacuum with the exclusion of light.

| Analysis: $C_9H_{15}N_2O_3S_2Ag$ (371) | | |
|---|---|---|
| Calc. %: | Ag | 29.11 |
| Found %: | | 29.16 |

The preceding sulfide 9 is suspended in 15 ml of $CHCl_3$ and stirred at ambient temperature with the exclusion of light and then 400 μl of concentrated hydrochloric acid are added. Stirring is continued for 2 h at ambient temperature and then for 2 min at 30–35° C. The mixture is then diluted with 70 ml of $CHCl_3$ and the silver chloride formed is filtered off and then washed with 3×10 ml of the same solvent. The organic phases are combined, rapidly washed with ice-cold water (3×10 ml), dried over sodium sulfate, filtered and evaporated to dryness under vacuum. A semi-crystalline paste is collected, which paste crystallizes from an AcOEt/petroleum ether mixture in the form of colorless microcrystals (368 mg, Yd=56%). M.p.=121–122° C. $[\alpha]_D^{20}$=39.1° (c 0.9, $CHCl_3$). The other data (microanalyses and spectra) are in all respects identical to those described in the second synthetic route. $H_2S$ was also used and leads to the same result.

1.2. Second Route for the Synthesis of I-152 Using N-protected L-serine:

1.2.1. N-(N-Boc-L-seryl)-2-aminoethanol (3)

A solution comprising 6.15 g (30 mmol) of N-Boc-L-serine (1, Fluka) and 3.45 g of N-hydroxysuccinimide (30 mmol) in 80 ml of DMF is stirred at 0° C. and 6.2 g (30 mmol) of DCC are added. The reaction mixture is maintained at 0° C. for 15 min, then it is allowed to return to ambient temperature and stirring is continued for 1 h 30. 2.75 ml (60 mmol) of ethanolamine are subsequently added. After stirring for 12 h, the DCU formed is filtered off and washed with 2×15 ml of DMF. The combined organic phases are evaporated to dryness under vacuum. The product is isolated from the residual paste by flash chromatography on a silica gel column (Kieselgel Merck 60, 230–400 mesh; eluent: $CH_2Cl_2$/MeOH 6%). The expected compound is collected in the form of a gum which crystallizes from an AcOEt/hexane mixture to provide 5.21 g (Yd=70%) of colorless needles. $R_f$ ($CH_2Cl_2$/MeOH, 9.3/0.7): 0.23; ($CH_2Cl_2$/MeOH/AcOH, 9/0.9/0.1): 0.47. M.p.=74–76° C. $[\alpha]_D^{20}$=−2.2° (c 0.9, $CHCl_3$).

$^1$H NMR ($d_6$-DMSO) δ ppm: 1.50 (s, 9H, H t-butyl), 3.18–3.29 (m, 2H, $NCH_2CH_2O$), 3.45–3.55 (m, 2H, $NCH_2CH_2O$), 3.57–3.70 (m, 2H, β $CH_2$ ser), 4.01–4.10 (m, 1H, α H ser), 4.77 (t, J=5.4 Hz, 1H, OH ser), 4.91 (t, J=5.7 Hz, 1H, $NCH_2CH_2OH$), 6.71 (d, J=8.2 Hz, 1H, NH ser); 7.86 (t, J=5.5 Hz, 1H, $NHCH_2$).

MS: ($FAB^+$/G−T) m/z 745 $(3M+H)^+$, 497 $(2M+H)^+$, 249 $(M+H)^+$.

| Analysis: $C_{10}H_{20}N_2O_5$ (248) | | | |
|---|---|---|---|
| Calc. %: | C 48.39 | H 8.06 | N 11.29 |
| Found %: | | 8.57 | 8.08 | 11.08 |

1.2.2. N-(N-Boc-S-acetyl-L-cysteinyl)-2-acetylcysteamine (4)

A solution comprising 2.597 g (9.9 mmol) of triphenylphosphine and 1.95 ml (9.91 mmol) of diisopropyl azodicarboxylate in 15 ml of THF is stirred for 30 min at 0° C. (after stirring for 30 s, the formation of an intense precipitate is observed). While retaining this temperature, 1.116 g (4.50 mmol) of 3, in solution in 6 ml of THF, and then 707 μl (9.91 mmol) of thioacetic acid are successively added. The solution obtained is subsequently allowed to return to ambient temperature and stirring is continued for 12 h. The reaction mixture is then evaporated to dryness under vacuum. The product is isolated from the residual paste by flash chromatography on a silica gel column (eluent: hexane and then AcOEt/petroleum ether 75%). The expected compound is collected in the form of a gum which crystallizes from an AcOEt/petroleum ether mixture in the form of colorless needles (1.21 g, Yd=74%). $R_f$ (AcOEt/petroleum ether, 4/6): 0.35. M.p.=111–113° C. $[\alpha]_D^{20}$=−13.9° (c 0.86, $CHCl_3$).

$^1$H NMR ($CDCl_3$) δ ppm: 1.45 (s, 9H, H t-butyl), 2.36, 2.38 (2s, 2×3H, 2×$SCOCH_3$), 2.99–3.07 (m, 2H, $NCH_2CH_2S$), 3.19 (dd, J=7.8, 14.3 Hz, 1H, β Ha cys), 3.34 (dd, J=4.5, 14.3 Hz, 1H, β Hb cys), 3.40–3.50 (m, 2H, $NCH_2CH_2S$), 4.19–4.34 (m, 1H, α H cys), 5.25 (d, J=7.1 Hz, 1H, NH cys), 6.69 (t, J=5.2 Hz, 1H, $NHCH_2$).

MS: ($FAB^+$/NBA) m/z 729 $(2M+H)^+$, 365 $(M+H)^+$.

| Analysis: $C_{14}H_{24}N_2O_5S_2$ (364) | | | |
|---|---|---|---|
| Calc. %: | C 46.15 | H 6.59 | N 7.69 |
| Found %: | 46.45 | 6.51 | 7.47 |

1.2.3. N-(N-acetyl-L-cysteinyl)-S-acetylcysteamine (I-152)

A solution comprising 500 mg (1.37 mmol) of 4 in 5 ml of $CH_2Cl_2$ is stirred under argon at 0° C. and then 1 ml (13.07 mmol) of TFA is added. The solution is subsequently allowed to return to ambient temperature and stirring is continued for 7 h. At this stage, the reaction, monitored by TLC ($CH_2Cl_2$/MeOH, 9.4/0.6), shows the disappearance of the starting compound ($R_f$: 0.75) and the appearance of two, more polar, spots ($R_f$: 0.5 and 0.16). The reaction mixture is evaporated to dryness under vacuum (temperature of the water bath: <40° C.).

Further monitoring by TLC of the gum obtained indicates that the preceding major spot at $R_f$: 0.16 has become a minor spot to the advantage of that at $R_f$: 0.5. The appearance of a third spot, of less importance, at $R_f$: 0.4 is also recorded. At this stage, we carried out flash chromatography on an aliquot of the gum (20 mg) in order to identify the compounds present in order to elucidate this phenomenon:

The product of $R_f$: 0.5 is isolated with a mixture of eluents consisting of $CH_2Cl_2$/$Et_2O$ (5/5). The study of its spectra ($^1$H NMR and MS) unambiguously shows that it is N-(2-methyl-$\Delta^2$-thiazolinyl-4(R)-carbonyl)-S-acetyl-cysteamine 6:

$^1$H NMR ($CDCl_3$) δ ppm: 2.32 (s, 3H, $SCOCH_3$), 2.39 (d, J=1.3 HZ, 3H, 2-$CH_3$ thiazoline), 3.05 (app. t, J=6.4 Hz, 2H, $NCH_2CH_2S$), 3.36–3.60 (m, 2H, $NCH_2CH_2S$), 3.69 (dd, J=10.2 and 11.4 Hz, 1H, 5-H thiazoline), 3.85 (dd, J=7.2 and 11.4 Hz, 1H, 5'-H thiazoline), 5.08 (ddd, J=1.3, 7.2 and 10.2 Hz, 1H, 4-H thiazoline), 7.45–7.58 (m, 1H, $NHCH_2$).

MS: ($FAB^+$/G−T) m/z 493 $(2M+H)^+$, 247 $(M+H)^+$.

The intermediate compound ($R_f$: 0.4) is isolated by increasing the polarity of the elution solvent ($CH_2Cl_2$/MeOH, 9.5/0.5). The study of its spectra ($^1$H NMR and MS) shows that it is I-152. Its physicochemical data are reported at the end of this description.

Continuing the chromatographic separation with more polar eluents ($CH_2Cl_2$/MeOH 5–20%) did not make it possible to obtain the product of $R_f$: 0.16. This compound, which is the first formed in the reaction for the deprotection of the terminal amine functional group of the starting N-Boc, can only be N-(S-acetyl-L-cysteinyl)-S-acetylcysteamine trifluoroacetate 5.

All the tests carried out and monitored by TLC showed us, under our operating conditions (time necessary for the complete consumption of the starting material, temperature and pH of the reaction medium), that 5, which is the first formed during deprotection of the N-Boc by TFA, generates the cyclic intermediate 6, which is subsequently slowly hydrolyzed to give I-152.

Thus, after these various observations, the remaining gum obtained after evaporation of the crude reaction mixture was dissolved in 150 ml of $CH_2Cl_2$, and then 5 ml of water were added at ambient temperature and with vigorous stirring. After stirring for 6 h, monitoring by TLC shows only a single spot corresponding to the desired product. The organic phase is separated by settling and the residual water is extracted with $CH_2Cl_2$ (3×10 ml). The organic phases are subsequently combined, dried over sodium sulfate, filtered and evaporated to dryness under vacuum. The expected compound is collected in the form of a semi-crystalline paste. $R_f$ ($CH_2Cl_2$/MeOH, 9.5/0.5): 0.4. Crystallizes from an AcOEt/petroleum ether mixture in the form of colorless microcrystals (245 mg, Yd=≧67%). M.p.=122–124° C. $[\alpha]_D^{20}$ =–40° (c 0.87, $CHCl_3$).

$^1$H NMR ($CDCl_3$) δ ppm: 1.60 (dd, J=7.6 and 10.3 Hz, 1H, SH), 2.07 (s, 3H, $NCOCH_3$), 2.36 (s, 3H, $SCOCH_3$), 2.70 (ddd, J=6.5, 10.3 and 13.9 Hz, 1H, β Ha cys), 3.03 (t, J=6.3 Hz, 2H, $NCH_2CH_2S$), 3.06 (ddd, J=4.3, 7.6 and 13.9 Hz, 1H, β Hb cys), 3.46 (td, J=6.0 and 6.3 Hz, 2H, $NCH_2CH_2S$), 4.59 (ddd, J=4.3, 6.5 and 7.9 Hz, 1H, α H cys), 6.52 (d, J=7.9 Hz, 1H, NH cys), 6.75–6.90 (m, 1H, $NHCH_2$).

MS: ($FAB^+$/G–T) m/z 529 $(2M+H)^+$, 265 $(M+H)^+$.

| Analysis: $C_9H_{16}N_2O_3S_2$ (264) | | | | |
|---|---|---|---|---|
| Calc. %: | C 40.91 | H 6.06 | N 10.61 | S 24.24 |
| Found %: | 41.21 | 6.00 | 10.91 | 23.99 |

EXAMPLE 2

Synthesis of acylated derivatives of N-(N-acetyl-L-cysteinyl)-S-acetylcysteamine (I-152) or of its derivatives 2.1. N-(N,S-bisacetyl-L-cysteinyl)-S-acetylcysteamine (I-176)
(General Method for S-acylation)

A solution comprising 83 mg (0.31 mmol) of I-152 in 1 ml of pyridine is stirred at 0° C. and 90 µl (0.95 mmol) of acetic anhydride are added. The reaction mixture is maintained at 0° C. for 15 min, then it is allowed to return to ambient temperature and stirring is continued for 12 h. The solution is subsequently evaporated to dryness under vacuum and the residue formed is taken up in 30 ml of $CH_2Cl_2$. The organic phase is washed with water (3×20 ml), dried over sodium sulfate, filtered and evaporated to dryness under vacuum. The residual gum, is crystallized from AcOEt and provides 73 mg (Yd=75%) of the expected compound in the form of colorless platelets. $R_f$ ($CH_2Cl_2$/MeOH, 9.5/0.5): 0.46. M.p.=153–154° C. $[\alpha]_D^{20}$=–33.7° (c 0.8, $CHCl_3$).

$^1$H NMR ($CDCl_3$) δ ppm: 2.02 (s, 3H, $NCOCH_3$), 2.37, 2.39 (2s, 2×3H, 2×$SCOCH_3$), 2.93, 3.12 (m, 2H, $NCH_2CH_2S$), 3.24 (dd, J=7.2 and 14.5 Hz, 1H, β Ha cys), 3.31 (dd, J=5.2 and 14.5 Hz, 1H) β Hb cys), 3.39–3.49 (m, 2H, $NCH_2CH_2S$), 4.54 (ddd, J=5.3, 7.2 and 7.3 Hz, 1H, α H cys), 6.44 (d, J=7.3 Hz, 1H, NH cys), 6.83 (t, J=5.1 Hz, 1H, $NHCH_2$).

MS: ($FAB^+$/G–T) m/z 613 $(2M+H)^+$, 307 $(M+H)^+$.

| Analysis: $C_{11}H_{18}N_2O_4S_2$ (306) | | | | |
|---|---|---|---|---|
| Calc. %: | C 43.14 | H 5.88 | N 9.15 | S 20.92 |
| Found %: | 42.95 | 5.96 | 8.93 | 20.64 |

2.2. N-(N-acetyl-S-isobutyryl-L-cysteinyl)-S-acetylcysteamine (I-177)

The acylation reaction of 85 mg (0.32 mmol) of I-152 is carried out, according to the general method described above, using 137 µl (1.30 mmol) of isobutyryl chloride instead of acetic anhydride. The viscous mixture obtained, after evaporation to dryness under vacuum, is subsequently diluted with 30 ml of $CH_2Cl_2$. The solution is subsequently washed (water, 10 ml; ice-cold saturated sodium bicarbonate, 10 ml; water, 10 ml; ice-cold 0.1N citric acid, 10 ml; water, 3×10 ml), dried over sodium sulfate, filtered and evaporated to dryness under vacuum. The acylation product is isolated from the gum obtained by flash chromatography on a silica gel column (eluent: $CH_2Cl_2$/ether 50%). 60 mg (Yd=56%) of the expected compound are collected. $R_f$ ($CH_2Cl_2$/MeOH, 9.4/0.6): 0.6. Crystallizes from an AcOEt/petroleum ether mixture in the form of colorless platelets. M.p.=116–118° C. $[\alpha]_D^{20}$=–18.4° (c 0.87, $CHCl_3$).

$^1$H NMR ($CDCl_3$) δ ppm: 1.20 (d, J=6.9 Hz, 6H, $C(CH_3)_2$, 2.00 (s, 3H, $NCOCH_3$), 2.37 (s, 3H, $SCOCH_3$), 2.80 (hept, J=6.9 Hz, 1H, $CH(CH_3)_2$, 2.93, 3.12 (m, 2H, $NCH_2CH_2S$), 3.23–3.30 (m, 2H, β $CH_2$ cys), 3.38–3.49 (m, 2H, $NCH_2CH_2S$), 4.46–4.57 (m, 1H, α H cys), 6.42 (d, J=7.3 Hz, 1H, NH cys), 6.80 (t, J=5.2 Hz, 1H, $NHCH_2$).

MS: ($FAB^+$/G–T) m/z 669 $(2M+H)^+$, 335 $(M+H)^+$.

| Analysis: $C_{13}H_{22}N_2O_4S_2$ (334) | | | | |
|---|---|---|---|---|
| Calc. %: | C 46.71 | H 6.59 | N 8.38 | S 19.16 |
| Found %: | 46.76 | 6.89 | 8.24 | 19.32 |

2.3. N-(N-acetyl-S-pivaloyl-L-cysteinyl)-S-acetylcysteamine (I-178)

The acylation reaction of 95 mg (0.36 mmol) of I-152 is carried out, according to the general method described above, using 176 µl (1.44 mmol) of pivaloyl chloride instead of acetic anhydride. The viscous mixture obtained, after evaporation to dryness under vacuum, is subsequently diluted with 30 ml of $CH_2Cl_2$. The solution is subsequently washed (water, 10 ml; ice-cold saturated sodium bicarbonate, 10 ml; water, 10 ml; ice-cold 0.1N citric acid, 10 ml; water, 3×10 ml), dried over sodium sulfate, filtered and evaporated to dryness under vacuum. The acylation product is isolated from the gum obtained by flash chromatography on a silica gel column (eluent: $CH_2Cl_2$/ether 50%). 70 mg (Yd=56%) of the expected compound are collected. $R_f$ ($CH_2Cl_2$/ether, 4/6): 0.23. Crystallizes from an AcOEt/petroleum ether mixture in the form of colorless platelets. M.p.=92–94° C. $[\alpha]_D^{20}$=–11.1° (c 1.08, $CHCl_3$).

$^1$H NMR ($CDCl_3$) δ ppm: 1.25 (s, 9H, $C(CH_3)_3$), 2.00 (s, 3H, $NCOCH_3$), 2.37 (s, 3H, $SCOCH_3$), 2.94, 3.12 (m, 2H, $NCH_2CH_2S$), 3.25 (d, J=6.5 Hz, 2H, β $CH_2$ cys), 3.38–3.49 (m, 2H, $NCH_2CH_2S$); 4.51 (td, J=6.5 and 7.3 Hz, 1H, α H cys), 6.42 (d, J=7.3 Hz, 1H, NH cys), 6.80 (t, J=5.2 Hz, 1H, $NHCH_2$).

MS: ($FAB^+$/G–T) m/z 697 $(2M+H)^+$, 349 $(M+H)^+$.

| Analysis: $C_{14}H_{24}N_2O_4S_2$ (348) | | | | |
|---|---|---|---|---|
| Calc. %: | C 48.28 | H 6.90 | N 8.05 | S 18.39 |
| Found %: | 48.32 | 6.95 | 7.94 | 18.43 |

2.4. N-(N-acetyl-S-trityl-L-cysteinyl)-S-isobutrylcysteamine (10)

The coupling reaction of 7 (4.5 mmol) with S-isobutyrylcysteamine hydrochloride [(compound obtained according to the same methods as those described by T. Wieland and E. Bokelman, *Ann. Chem.*, 1952, 576, 20–34; during the syntheses of S-acetylcysteamine hydrochloride and S-benzoylcysteamine hydrochloride) M.p.=147–148° C.] is carried out according to method B described in the first synthetic route (example 1). After the various treatments, the expected compound is isolated by flash chromatography on a silica gel column (eluent: $CH_2Cl_2$/ether 30%). 10 is collected in the form of a colorless foam with a yield of 80%. $R_f$ (AcOEt/petroleum ether, 8/2): 0.37. $[\alpha]_D^{20}$=+10° (c 1.1, $CHCl_3$).

$^1$H NMR ($CDCl_3$) δ ppm: 1.16 (d, J=6.9 Hz, 6H, $C(CH_3)_2$), 1.90 (s, 3H, $NCOCH_3$), 2.49 (dd, J=5.7 and 12.9 Hz, 1H, β Ha cys), 2.70 (hept, J=6.9 Hz, 1H, $CH(CH_3)_2$), 2.79 (dd, J=6.4 and 12.9 Hz, 1H, β Hb cys), 2.88–3.01 (m, 2H, $NCH_2CH_2S$), 3.29–3.41 (m, 2H, $NCH_2CH_2S$), 4.08–4.19 (m, 1H, α H cys), 5.76 (d, J=7.7 Hz, 1H, NH cys), 6.36 (t, J=5.5 Hz, 1H, $NHCH_2$), 7.15–7.35, 7.38–7.52 (2m, 15H, aromatic H).

MS: ($FAB^+$/G–T) m/z 535 $(M+H)^+$.

| Analysis: $C_{30}H_{34}N_2O_3S_2$ (534) | | | |
|---|---|---|---|
| Calc. %: | C 67.42 | H 6.37 | N 5.24 |
| Found %: | 67.25 | 6.58 | 5.30 |

2.5. N-(N-acetyl-L-cysteinyl)-S-isobutyrylcysteamine (I-188)

This compound is obtained by the S-detritylation of 10 (2.38 mmol). The protocol used is the same as that described in example 1 for the synthesis of I-152. After the various treatments, a gum is collected, which gum is purified by flash chromatography on a silica gel column (eluent: $CH_2Cl_2$/MeOH 1.5%). I-188 is isolated in the form of a colorless semicrystalline gum with a yield of 57%.

$R_f$($CH_2Cl_2$/MeOH, 9.5/0.5): 0.45. $[\alpha]_D^{20}$=−26.6° (c 1.09, $CHCl_3$).

$^1$H NMR ($CDCl_3$) δ ppm: 1.21 (d, J=6.9 Hz, 6H, $C(CH_3)_2$), 1.61 (dd, J=7.6 and 10.3 Hz, 1H, SH), 2.09 (s, 3H, $NCOCH_3$), 2.70 (ddd, J=6.4, 10.3 and 13.8 Hz, 1H, β Ha cys), 2.77 (hept, J=6.9 Hz, 1H, $CH(CH_3)_2$), 2.99–3.08 (m, 2H, $NCH_2CH_2S$), 3.09 (ddd, J=4.1, 7.6 and 13.8 Hz, 1H, β Hb cys), 3.41–3.53 (m, 2H, $NCH_2CH_2S$), 4.60 (ddd, J=4.1, 6.4 and 7.5 Hz, 1H, α H cys), 6.48 (d, J=7.5 Hz, 1H, NH cys), 6.68–6.88 (m, 1H, $NHCH_2$).

MS: ($FAB^+$/G–T) m/z 585 $(2M+H)^+$, 293 $(M+H)^+$.

| Analysis: $C_{11}H_{20}N_2O_3S_2$ (292) | | | |
|---|---|---|---|
| Calc. %: | C 45.20 | H 6.85 | N 9.59 |
| Found %: | 45.31 | 7.09 | 9.41 |

2.6. N-(N,S-bisacetyl-L-cysteinyl)-S-isobutyrylcysteamine (I-189)

The S-acylation of I-188 (0.32 mmol) with acetic anhydride is carried out according to the general method described in example 2. The reaction mixture is subsequently treated to the protocol described for the synthesis of I-177. After the various treatments, a gum is collected, which gum is purified by flash chromatography on a silica gel column (eluent: $CH_2Cl_2$/ether 55%). I-189 is isolated in the form of a gum (Yd=64%) which, after trituration in hexane, provides a colorless powder. $R_f$ ($CH_2Cl_2$/MeOH, 9.5/0.5): 0.58. M.p.=115–117° C. $[\alpha]_D^{20}$=−20.2° (c 1.04, $CHCl_3$).

$^1$H NMR ($CDCl_3$) δ ppm: 1.20 (d, J=6.9 Hz, 6H, $C(CH_3)_2$), 2.02 (s, 3H, $NCOCH_3$), 2.38 (s, 3H, $SCOCH_3$), 2.78 (hept, J=6.9 Hz, 1H, $CH(CH_3)_2$), 2.96–3.06 (m, 2H, $NCH_2CH_2S$), 3.19–3.36 (m, 2H, $CH_2$ cys), 3.38–3.48 (m, 2H, $NCH_2CH_2S$), 4.47–4.60 (m, 1H, α H cys), 6.37 (d, J=7.1 Hz, 1H, NH cys); 6.70–6.83 (m, 1H, $NHCH_2$).

MS: ($FAB^+$/G–T) m/z 669 $(2M+H)^+$, 335 $(M+H)^+$.

| Analysis: $C_{13}H_{22}N_2O_4S_2$ (334) | | | |
|---|---|---|---|
| Calc. %: | C 46.71 | H 6.59 | N 8.38 |
| Found %: | 46.81 | 6.62 | 8.36 |

2.7. N-(N-acetyl-S-isobutyryl-L-cysteinyl)-S-isobutyrylcysteamine (I-190)

The S-acylation of I-188 (0.32 mmol) with isobutyryl chloride is carried out according to the general method described in example 2. The reaction mixture is subsequently treated according to the protocol described for the synthesis of I-177. After the various treatments, a gum is collected, which gum is purified by flash chromatography on a silica gel column (eluent: $CH_2Cl_2$/ether 50%). I-190 is isolated in the form of a gum (Yd=63%) which, after trituration in hexane, provides a colorless powder. $R_f$ ($CH_2Cl_2$/ether, 3.5/6.5): 0.34. M.p.=99–100° C. $[\alpha]_D^{20}$=−9.10 (c 0.88, $CHCl_3$).

$^1$H NMR ($CDCl_3$) δ ppm: 1.20 (d, J=6.9 Hz, 12H, $C(CH_3)_2$), 2.01 (s, 3H, $NCOCH_3$), 2.78 (hept, J=6.9 Hz, 2H, $CH(CH_3)_2$), 2.92–3.10 (m, 2H, $NCH_2CH_2S$), 3.26 (d, J=6.4 Hz, 2H, $CH_2$ cys), 3.37–3.48 (m, 2H, $NCH_2CH_2S$), 4.46–4.58 (m, 1H, α H cys), 6.38 (d, J=7.3 Hz, 1H, NH cys), 6.73–6.83 (m, 1H, $NHCH_2$).

MS: ($FAB^+$/G–T) m/z 725 $(2M+H)^+$, 363 $(M+H)^+$.

| Analysis: $C_{15}H_{26}N_2O_4S_2$ (362) | | | |
|---|---|---|---|
| Calc. %: | C 49.72 | H 7.18 | N 7.73 |
| Found %: | 49.57 | 7.19 | 7.68 |

2.8. N-(N-acetyl-S-pivaloyl-L-cysteinyl)-S-isobutyrylcysteamine (I-191)

The S-acylation of I-188 (0.32 mmol) with isobutyryl chloride is carried out according to the general method described in example 2. The reaction mixture is subsequently treated according to the protocol described for the synthesis of I-177. After the various treatments, a gum is collected, which gum crystallizes from an AcOEt/petroleum ether mixture in colorless needles (Yd=68%). $R_f$ ($CH_2Cl_2$/ether, 5/5): 0.27. M.p.=103–104° C. $[\alpha]_D^{20}$=−8.3° (c 0.97, $CHCl_3$).

$^1$H NMR ($CDCl_3$) δ ppm: 1.20 (d, J=6.9 Hz, 6H, $C(CH_3)_2$, 1.25 (s, 9H, $C(CH_3)_3$), 2.01 (s, 3H, $NCOCH_3$), 2.77 (hept, J=6.9 Hz, 1H, CH(CH$_3$)$_2$), 2.94–3.08 (m, 2H, NCH$_2$CH$_2$S), 3.25 (d, J=6.4 Hz, 2H, CH$_2$ cys), 3.37–3.49 (m, 2H, NCH$_2$CH$_2$S), 4.44–4.57 (m, 1H, α H cys), 6.35 (d, J=7.3 Hz, 1H, NH cys), 6.69–6.80 (m, 1H, NHCH$_2$).

MS: (FAB$^+$/G–T) m/z 753 (2M+H)$^+$, 377 (M+H)$^+$.

| Analysis: C$_{16}$H$_{28}$N$_2$O$_4$S$_2$ (376) | | | | | | |
|---|---|---|---|---|---|---|
| Calc. %: | C | 51.06 | H | 7.45 | N | 7.45 |
| Found %: | | 51.16 | | 7.53 | | 7.44 |

2.9. N-(N-acetyl-S-benzoyl-L-cysteinyl)-S-isobutyrylcysteamine (I-192)

The S-acylation of I-188 (0.32 mmol) with benzoyl chloride is carried out according to the general method described in example 2. The reaction mixture is subsequently treated according to the protocol described for the synthesis I-177. After the various treatments, a gum is collected, which gum is purified by flash chromatography on a silica gel column (eluent: CH$_2$Cl$_2$/ether 35%). I-192 is isolated in the form of a gum (Yd=63%) which, after trituration in hexane, provides a colorless powder. R$_f$ (CH$_2$Cl$_2$/ether, 5/5): 0.27. M.p.= 137–138° C. [α]$_D^{20}$=+2.8° (c 1.08, CHCl$_3$).

$^1$H NMR (CDCl$_3$) δ ppm: 1.18 (d, J=6.9 Hz, 6H, C(CH$_3$)$_2$), 2.02 (s, 3H, NCOCH$_3$), 2.73 (hept, J=6.9 Hz, 1H, CH(CH$_3$)$_2$), 2.96–3.06 (m, 2H, NCH$_2$CH$_2$S), 3.39–3.49 (m, 2H, NCH$_2$CH$_2$S), 3.50 (d, J=6.2 Hz, 2H, CH$_2$ cys), 4.60–4.72 (m, 1H, α H cys), 6.59 (d, J=7.3 Hz, 1H, NH cys), 6.85–6.97 (m, 1H, NHCH$_2$), 7.41–7.52, 7.57–7.65 and 7.93–8.01 (3m, 5H, aromatic H).

MS: (FAB$^+$/G–T) m/z 793 (2M+H)$^+$, 397 (M+H)$^+$.

| Analysis: C$_{18}$H$_{24}$N$_2$O$_4$S$_2$ (396) | | | | | | |
|---|---|---|---|---|---|---|
| Calc. %: | C | 54.55 | H | 6.06 | N | 7.07 |
| Found %: | | 54.89 | | 6.11 | | 7.06 |

2.10. N-(N-acetyl-S-trityl-L-cysteinyl)-S-pivaloylcysteamine (11)

The coupling reaction of 7 (7.4 mmol) with S-pivaloylcysteamine hydrochloride [(compound obtained according to the same methods as those described by T. Wieland and E. Bokelman, *Ann. Chem.*, 1952, 576, 20–34, during the syntheses of S-acetylcysteamine hydrochloride and S-benzoylcysteamine hydrochloride) M.p.=212–213° C.] is carried out according to method B described in the first synthetic route (example 1). After the various treatments, the expected compound is isolated by flash chromatography on a silica gel column (eluent: CH$_2$Cl$_2$/ether 30%). 11 is collected in the form of a colorless foam with a yield of 86%. R$_f$ (AcOEt/petroleum ether, 7/3): 0.5. [α]$_D^{20}$=+8.5° (c 1.29, CHCl$_3$).

$^1$H NMR (CDCl$_3$) δ ppm: 1.21 (s, 9H, C(CH$_3$)$_3$), 1.90 (s, 3H, NCOCH$_3$), 2.49 (dd, J=5.9 and 12.9 Hz, 1H, □ Ha cys), 2.78 (dd, J=6.5 and 12.9 Hz, 1H, β Hb cys), 2.88–2.98 (m, 2H, NCH$_2$CH$_2$S), 3.28–3.40 (m, 2H, NCH$_2$CH$_2$S), 4.06–4.19 (m, 1H, α H cys), 5.77 (d, J=7.6 Hz, 1H, NH cys), 6.27–6.41 (m, 1H, NHCH$_2$), 7.16–7.35 and 7.40–7.48 (2 m, 15H, aromatic H).

MS: (FAB$^+$/G–T) m/z 549 (M+H)$^+$.

| Analysis: C$_{31}$H$_{36}$N$_2$O$_3$S$_2$ (548) | | | | | | |
|---|---|---|---|---|---|---|
| Calc. %: | C | 67.88 | H | 6.57 | N | 5.11 |
| Found %: | | 66.73 | | 6.70 | | 5.17 |

2.11. N-(N-acetyl-L-cysteinyl)-S-pivaloylcysteamine (I-193)

This compound is obtained by S-detritylation of 11 (4.57 mmol). The protocol used is the same as that described in example 1 for the synthesis of I-152. After the various treatments, a gum is collected, which gum is purified by flash chromatography on a silica gel column (eluent: CH$_2$Cl$_2$/MeOH 1.5%). I-193 is isolated in the form of a colorless semicrystalline gum with a yield of 60%.

R$_f$ (CH$_2$Cl$_2$/MeOH, 9.5/0.5): 0.49. [α]$_D^{20}$=–20.2° (c 0.94, CHCl$_3$).

$^1$H NMR (CDCl$_3$) δ ppm: 1.24 (s, 9H, C(CH$_3$)$_3$), 1.61 (dd, J=7.6 and 10.3 Hz, 1H, SH), 2.08 (s, 3H, NCOCH$_3$), 2.70 (ddd, J=6.4, 10.3 and 13.9 Hz, 1H, β Ha cys), 2.97–3.09 (m, 2H, NCH$_2$CH$_2$S), 3.08 (ddd, J=4.1, 7.6 and 13.9 Hz, 1H, β Hb cys), 3.40–3.52 (m, 2H, NCH$_2$CH$_2$S), 4.60 (ddd, J=4.1, 6.4 and 7.8 Hz, 1H, α H cys), 6.49 (d, J=7.8 Hz, 1H, NH cys), 6.69–6.82 (m, 1H, NHCH$_2$).

MS: (FAB$^+$/G–T) m/z 613 (2M+H)$^+$, 307 (M+H)$^+$.

| Analysis: C$_{12}$H$_{22}$N$_2$O$_3$S$_2$ (306) | | | | | | |
|---|---|---|---|---|---|---|
| Calc. %: | C | 47.06 | H | 7.19 | N | 9.15 |
| Found %: | | 47.37 | | 7.23 | | 9.22 |

2.12. N-(N,S-bisacetyl-L-cysteinyl)-S-pivaloylcysteamine (I-194)

The S-acylation of I-193 (0.33 mmol) with acetic anhydride is carried out according to the general method described in example 2. The reaction mixture is subsequently treated according to the protocol described for the synthesis of I-177. After the various treatments, a gum is collected, which gum is purified by flash chromatography on a silica gel column (eluent: CH$_2$Cl$_2$/ether 55%). I-194 is isolated in the form of a gum (Yd=71%) which crystallizes from an AcOEt/petroleum ether mixture in colorless platelets. R$_f$ (CH$_2$Cl$_2$/MeOH, 9.5/0.5): 0.58. M.p.=112–114° C. [α]$_D^{20}$=–13.8° (c 0.94, CHCl$_3$).

$^1$H NMR (CDCl$_3$) δ ppm: 1.24 (s, 9H, C(CH$_3$)$_3$), 2.03 (s, 3H, NCOCH$_3$), 2.38 (s, 3H, SCOCH$_3$), 2.94–3.04 (m, 2H, NCH$_2$CH$_2$S), 3.18–3.36 (m, 2H, CH$_2$ cys), 3.36–3.48 (m, 2H, NCH$_2$CH$_2$S), 4.48–4.60 (m, 1H, α H cys), 6.40 (d, J=7.5 Hz, 1H, NH cys), 6.71–6.83 (m, 1H, NHCH$_2$).

MS: (FAB$^+$/G–T) m/z 697 (2M+H)$^+$, 349 (M+H)$^+$.

| Analysis: C$_{14}$H$_{24}$N$_2$O$_4$S$_2$ (348) | | | | | | |
|---|---|---|---|---|---|---|
| Calc. %: | C | 48.28 | H | 6.90 | N | 8.05 |
| Found %: | | 48.34 | | 7.00 | | 7.97 |

2.13. N-(N-acetyl-S-isobutyryl-L-cysteinyl)-S-pivaloylcysteamine (I-195)

The S-acylation of I-193 (0.32 mmol) with isobutyryl chloride is carried out according to the general method described in example 2. The reaction mixture is subsequently treated according to the protocol described for the synthesis of I-177. After the various treatments, a gum is collected, which gum, after triturations from hexane, provides a colorless powder which is homogeneous by TLC (Yd=56%). $R_f$ ($CH_2Cl_2$/ether, 3.5/6.5): 0.46. M.p.= 101–102° C. $[\alpha]_D^{20}$=−5.7° (c 1.05, $CHCl_3$).

$^1$H NMR ($CDCl_3$) δ ppm: 1.20 (d, J=6.9 Hz, 6H, $C(CH_3)_2$), 1.25 (s, 9H, $C(CH_3)_3$), 2.01 (s, 3H, $NCOCH_3$), 2.79 (hept, J=6.9 Hz, 1H, $CH(CH_3)_2$), 2.90–3.08 (m, 2H, $NCH_2CH_2S$), 3.25 (d, J=6.3 Hz, $CH_2$ cys), 3.35–3.47 (m, 2H, $NCH_2CH_2S$), 4.46–4.58 (m, 1H, α H cys), 6.38 (d, J=7.1 Hz, 1H, NH cys), 6.71–6.81 (m, 1H, $NHCH_2$).

MS: ($FAB^+$/G–T) m/z 753 $(2M+H)^+$, 377 $(M+H)^+$.

| Analysis: $C_{16}H_{28}N_2O_4S_2$ (376) | | | | | | |
|---|---|---|---|---|---|---|
| Calc. %: | C | 51.06 | H | 7.45 | N | 7.45 |
| Found %: | | 51.20 | | 7.49 | | 7.46 |

2.14. N-(N-acetyl-S-pivaloyl-L-cysteinyl)-S-pivaloylcysteamine (I-196)

The S-acylation of I-193 (0.34 mmol) with pivaloyl chloride is carried out according to the general method described in example 2. The reaction mixture is subsequently treated according to the protocol described for the synthesis of I-177. After the various treatments, a gum is collected, which gum, after triturations in hexane, provides a colorless powder (Yd=66%). $R_f$ ($CH_2Cl_2$/ether, 5/5): 0.36. Crystallizes from an AcOEt/petroleum ether mixture in the form of colorless microcrystals. M.p.=109–111° C. $[\alpha]_D^{20}$=−4.4° (c 0.91, $CHCl_3$).

$^1$H NMR ($CDCl_3$) δ ppm: 1.24 (s, 18H, $C(CH_3)_3$), 2.00 (s, 3H, $NCOCH_3$), 2.90–3.08 (m, 2H, $NCH_2CH_2S$), 3.24 (d, J=6.4 Hz, 2H, $CH_2$ cys), 3.36–3.47 (m, 2H, $NCH_2CH_2S$), 4.44–4.57 (m, 1H, α H cys), 6.38 (d, J=7.4 Hz, 1H, NH cys), 6.68–6.88 (m, 1H, $NHCH_2$).

MS: ($FAB^+$/G–T) m/z 781 $(2M+H)^+$, 391 $(M+H)^+$.

| Analysis: $C_{17}H_{30}N_2O_4S_2$ (390) | | | | | | |
|---|---|---|---|---|---|---|
| Calc. %: | C | 52.31 | H | 7.69 | N | 7.18 |
| Found %: | | 52.47 | | 7.70 | | 7.14 |

2.15. N-(N-acetyl-S-benzoyl-L-cysteinyl)-S-pivaloylcysteamine (I-197)

The S-acylation of I-193 (0.34 mmol) with benzoyl chloride is carried out according to the general method described in example 2. The reaction mixture is subsequently treated according to the protocol described for the synthesis of I-177. After the various treatments, a gum is collected, which gum is purified by flash chromatography on a silica gel column (eluent: $CH_2Cl_2$/ether 35%). I-197 is isolated in the form of a gum which, after trituration in hexane, provides a colorless powder (Yd=66%). $R_f$ ($CH_2Cl_2$/ether, 5/5): 0.33. M.p.=133–134° C. $[\alpha]_D^{20}$=+5.10° (c 0.98, $CHCl_3$).

$^1$H NMR (CDCl3) δ ppm: 1.21 (s, 9H, $C(CH_3)_3$); 2.01 (s, 3H, $NCOCH_3$), 2.90–3.08 (m, 2H, $NCH_2CH_2S$), 3.33–3.52 (m, 4H, $NCH_2CH_2S$, $CH_2$ cys), 4.64–4.77 (m, 1H, α H cys), 6.76 (d, J=7.4 Hz, 1H, NH cys), 7.06–7.22 (m, 1H, $NHCH_2$), 7.40–7.50, 7.55–7.63, 7.91–8.0 (3m, 5H, aromatic H).

MS: ($FAB^+$/G–T) m/z 821 $(2M+H)^+$, 411 $(M+H)^+$.

| Analysis: $C_{19}H_{26}N_2O_4S_2$ (410) | | | | | | |
|---|---|---|---|---|---|---|
| Calc. %: | C | 55.61 | H | 6.34 | N | 6.83 |
| Found %: | | 55.29 | | 6.35 | | 6.75 |

2.16. N-(N-acetyl-S-trityl-L-cysteinyl)-S-benzoylcysteamine (12)

The coupling reaction of 7 (7.41 mmol) is carried out according to Method B described in the first synthetic route (example 1): S-acetylcysteamine hydrochloride was replaced by S-benzoylcysteamine hydrochloride (T. Wieland and E. Bokelman, Ann. Chem., 1952, 576, 20–34. After the various treatments, the expected compound is isolated by flash chromatography on a silica gel column (eluent: $CH_2Cl_2$/ether 15%). 12 is collected in the form of a colorless foam with a yield of 62%. $R_f$ (AcOEt/petroleum ether, 7/3): 0.42. $[\alpha]_D^{20}$=+10.8° (c 1.11, $CHCl_3$).

$^1$H NMR ($CDCl_3$) δ ppm: 1.86 (s, 3H, $NCOCH_3$), 2.47 (dd, J=5.7 and 13.0 Hz, 1H, β Ha cys), 2.82 (dd, J=6.4 and 13.0 Hz, 1H, β Hb cys), 3.08–3.27 (m, 2H, $NCH_2CH_2S$), 3.41–3.53 (m, 2H, $NCH_2CH_2S$), 4.08–4.21 (m, 1H, α H cys), 5.67 (d, J=7.7 Hz, 1H, NH cys), 6.34–6.46 (m, 1H, $NHCH_2$), 7.17–7.32, 7.37–7.45, 7.54–7.61, 7.89–7.96 (4m, 20H, aromatic H).

MS: ($FAB^+$/G–T) m/z 569 $(M+H)^+$.

| Analysis: $C_{33}H_{32}N_2O_3S_2$ (568) | | | | | | |
|---|---|---|---|---|---|---|
| Calc. %: | C | 69.72 | H | 5.63 | N | 4.93 |
| Found %: | | 68.96 | | 5.62 | | 4.89 |

2.17. N-(N-acetyl-L-cysteinyl)-S-benzoylcysteamine (I-198)

This compound is obtained by the S-detritylation of 12 (4.44 mmol). The protocol used is the same as that described in example 1 for the synthesis of I-152. After the various treatments, a gum is collected, which gum is purified by flash chromatography on a silica gel column (eluent: AcOEt/petroleum ether 50%). I-198 is isolated in the form of a white solid with a yield of 63%. $R_f$ $CH_2Cl_2$/MeOH, 9.5/0.5): 0.38. M.p.=128–130° C. $[\alpha]_D^{20}$=−24.7° (c 1.01, $CHCl_3$).

$^1$H NMR ($CDCl_3$) δ ppm: 1.59 (dd, J=7.6 and 10.2 Hz, 1H, SH), 2.04 (s, 3H, $NCOCH_3$), 2.71 (ddd, J=6.5, 10.2 and 13.8 Hz, 1H, β Ha cys), 3.06 (ddd, J=4.3, 7.6 and 13.8 Hz, 1H, β Hb cys), 3.20–3.31 (m, 2H, $NCH_2CH_2S$), 3.52–3.64 (m, 2H, $NCH_2CH_2S$), 4.61 (ddd, J=4.3, 6.5 and 7.4 Hz, 1H, α H cys), 6.51 (d, J=7.4 Hz, 1H, NH cys), 6.83–7.00 (m, 1H, $NHCH_2$), 7.43–7.52, 7.56–7.65, 7.92–8.00 (3m, 5H, aromatic H).

MS: ($FAB^+$/G–T) m/z 653 $(2M+H)^+$, 327 $(M+H)^+$.

| Analysis: $C_{14}H_{18}N_2O_3S_2$ (326) | | | | | | |
|---|---|---|---|---|---|---|
| Calc. %: | C | 51.53 | H | 5.52 | N | 8.59 |
| Found %: | | 51.49 | | 5.55 | | 8.60 |

2.18. N-(N,S-bisacetyl-L-cysteinyl)-S-benzoylcysteamine (I-199)

The S-acylation of I-198 (0.34 mmol) with acetic anhydride is carried out according to the general method described in example 2. The reaction mixture is subsequently treated according to the protocol described for the synthesis of I-177. After the various treatments, a gum is collected, which gum is purified by flash chromatography on a silica gel column (eluent: $CH_2Cl_2$/MeOH 1.5%). I-199 is isolated in the form of a gum (Yd=75%) which crystallizes from AcOEt in colorless needles. $R_f$ ($CH_2Cl_2$/MeOH, 9.5/0.5): 0.44. M.p.=166–168° C. $[\alpha]_D^{20}$=–14.3° (c 0.98, $CHCl_3$).

$^1$H NMR ($CDCl_3$) δ ppm: 1.99 (s, 3H, $NCOCH_3$), 2.32 (s, 3H, $SCOCH_3$), 3.18–3.31 (m, 4H, $NCH_2CH_2S$, $CH_2$ cys), 3.48–3.61 (m, 2H, $NCH_2CH_2S$), 4.49–4.62 (m, 1H, α H cys), 6.38 (d, J=7.6 Hz, 1H, NH cys), 6.79–6.92 (m, 1H, $NHCH_2$), 7.42–7.51, 7.55–7.64, 7.93–8.01 (3m, 5H, aromatic H).

MS: ($FAB^+$/G–T) m/z 737 $(2M+H)^+$, 369 $(M+H)^+$.

| Analysis: $C_{16}H_{20}N_2O_4S_2$ (368) | | | | | | |
|---|---|---|---|---|---|---|
| Calc. %: | C | 52.17 | H | 5.43 | N | 7.61 |
| Found %: | | 52.33 | | 5.45 | | 7.68 |

2.19. N-(N-acetyl-S-isobutyryl-L-cysteinyl)-S-benzoylcysteamine (I-200)

The S-acylation of I-198 (0.30 mmol) with isobutyryl chloride is carried out according to the general method described in example 2. The reaction mixture is subsequently treated according to the protocol described for the synthesis of I-177. After the various treatments, a gum is collected, which gum is purified by flash chromatography on a silica gel column (eluent: $CH_2Cl_2$/ether 40%). I-200 is isolated in the form of a gum (Yd=79%) which crystallizes from an AcOEt/petroleum ether mixture in colorless platelets. $R_f$ ($CH_2Cl_2$/ether, 3/7): 0.2. M.p.=135–136° C. $[\alpha]_D^{20}$=–6.7° (c 1.2, $CHCl_3$).

$^1$H NMR ($CDCl_3$) δ ppm: 1.17 (d, J=6.9 Hz, 6H, $C(CH_3)_2$), 1.97 (s, 3H, $NCOCH_3$), 2.75 (hept, J=6.9 Hz, 1H, $CH(CH_3)_2$), 3.19–3.30 (m, 4H, $NCH_2CH_2S$, $CH_2$ cys), 3.46–3.62 (m, 2H, $NCH_2CH_2S$), 4.49–4.61 (m, 1H, α H cys), 6.41 (d, J=7.4 Hz, 1H, NH cys), 6.85–6.96 (m, 1H, $NHCH_2$), 7.41–7.52, 7.55–7.64, 7.90–8.02 (3m, 5H, aromatic H).

MS: ($FAB^+$/G–T) m/z 793 $(2M+H)^+$, 397 $(M+H)^+$.

| Analysis: $C_{18}H_{24}N_2O_4S_2$ (396) | | | | | | |
|---|---|---|---|---|---|---|
| Calc. %: | C | 54.54 | H | 6.06 | N | 7.07 |
| Found %: | | 54.77 | | 6.04 | | 7.07 |

2.20. N-(N-acetyl-S-pivaloyl-L-cysteinyl)-S-benzoylcysteamine (I-201)

The S-acylation of I-198 (0.30 mmol) with pivaloyl chloride is carried out according to the general method described in example 2. The reaction mixture is subsequently treated according to the protocol described for the synthesis of I-177. After the various treatments, a gum is collected, which gum is purified by flash chromatography on a silica gel column (eluent: $CH_2Cl_2$/ether 45%). I-201 is isolated in the form of a gum (Yd=83%) which crystallizes from an AcOEt/petroleum ether mixture in colorless platelets. $R_f$ ($CH_2Cl_2$/ether, 3/7): 0.3. M.p.=101–103° C. $[\alpha]_D^{20}$=–3.8° (c 1.05, $CHCl_3$).

$^1$H NMR ($CDCl_3$) δ ppm: 1.22 (s, 9H, $C(CH_3)_3$), 1.96 (s, 3H, $NCOCH_3$), 3.19–3.30 (m, 4H, $NCH_2CH_2S$, $CH_2$ cys), 3.46–3.62 (m, 2H, $NCH_2CH_2S$), 4.47–4.58 (m, 1H, α H cys), 6.38 (d, J=7.2 Hz, 1H, NH cys), 6.81–6.92 (m, 1H, $NHCH_2$), 7.42–7.52, 7.55–7.65, 7.90–8.02 (3m, 5H, aromatic H).

MS: ($FAB^+$/G–T) m/z 821 $(2M+H)^+$, 411 $(M+H)^+$.

| Analysis: $C_{19}H_{26}N_2O_4S_2$ (410) | | | | | | |
|---|---|---|---|---|---|---|
| Calc. %: | C | 55.61 | H | 6.34 | N | 6.83 |
| Found %: | | 55.73 | | 6.29 | | 6.85 |

2.21. N-(N-acetyl-S-benzoyl-L-cysteinyl)-S-benzoylcysteamine (I-202)

The S-acylation of I-198 (0.30 mmol) with benzoyl chloride is carried out according to the general method described in example 2. The reaction mixture is subsequently treated according to the protocol described for the synthesis of I-177. After the various treatments, a gum is collected, which gum is purified by flash chromatography on a silica gel column (eluent: $CH_2Cl_2$/MeOH 1%). I-202 is isolated in the form of a gum (Yd=72%) which crystallizes from an AcOEt in colorless platelets. $R_f$ ($CH_2Cl_2$/MeOH, 9.5/0.5): 0.66. M.p.=188–190° C. $[\alpha]_D^{20}$=+4.1° (c 0.98, $CHCl_3$).

$^1$H NMR ($CDCl_3$) δ ppm: 1.99 (s, 3H, $NCOCH_3$), 3.19–3.28 (m, 2H, $NCH_2CH_2S$), 3.49 (d, J=6.1 Hz, 2H, $CH_2$ cys), 3.52–3.61 (m, 2H, $NCH_2CH_2S$), 4.63–4.71 (m, 1H, α H cys), 6.56 (d, J=7.2 Hz, 1H, NH cys), 6.92–7.08 (m, 1H, $NHCH_2$), 7.38–7.48, 7.52–7.62, 7.88–7.97 (3m, 10H, aromatic H).

MS: ($FAB^+$/G–T) m/z 861 $(2M+H)^+$, 431 $(M+H)^+$.

| Analysis: $C_{21}H_{22}N_2O_4S_2$ (430) | | | | | | |
|---|---|---|---|---|---|---|
| Calc. %: | C | 58.60 | H | 5.12 | N | 6.51 |
| Found %: | | 58.37 | | 5.10 | | 6.51 |

2.22. N-isobutyryl-S-trityl-L-cysteine (13)

This compound was synthesized by adapting, to N-isobutyryl-L-cysteine, the tritylation method described by K.-Y. Zee-Cheng and C. C. Cheng, *J. Med. Chem.*, 1970, 13, 414–418. A suspension comprising 4.1 g (21.5 mmol) of N-isobutyryl-L-cysteine [(prepared according to H. Brückner et al., *J. Chromatogr.*, 1989, 476, 73–82), ($[\alpha]_D^{20}$=+84° (c 1, $CHCl_3$))], 5.6 g (21.5 mmol) of triphenylmethanol and 16 ml of glacial acetic acid is stirred at ambient temperature. 4.1 ml (32.2 mmol) of $BF_3$ etherate are added dropwise to the mixture while maintaining the temperature at 20–25° C. After stirring for 3 h, the brown solution obtained is subsequently cooled to 0° C. and then 70 ml of an aqueous sodium acetate solution and 140 ml of water are added. At the end of the additions, the reaction mixture sets solid in the form of a gel. This mixture is left overnight at 0° C. and then 150 ml of ice-cold water and 120 ml of ether are subsequently added with vigorous stirring. The ethereal phase is separated by settling and the aqueous waste liquors are washed with 4×80 ml of ether. The organic phases are combined, washed with 4×60 ml of ice-cold water, dried over sodium sulfate, filtered and evaporated to dryness under vacuum. The crude product obtained is purified by washing successively with hexane (5×50 ml) to provide 13 in the form of a gum which is homogeneous by TLC with a yield of 81%. $R_f$ ($CH_2Cl_2$/MeOH/AcOH, 9.4/0.6/0.07): 0.53. $[\alpha]_D^{20}$=+21.40 (c 1.12, $CHCl_3$).

$^1$H NMR ($CDCl_3$) δ ppm: 1.12, 1.14 (2d, J=2×6.9 Hz, 2×3H, $C(CH_3)_2$), 2.24–2.42 (m, 1H, $CH(CH_3)_2$, 2.64–2.28 (m, 2H, $CH_2$), 4.31–4.43 (m, 1H, α H), 5.67–6.15 (broad m, 1H, $CO_2H$), 5.90 (d, J=7.1 Hz, 1H, NH partially concealing the m at 5.67–6.15), 7.18–7.33, 7.37–7.46 (2m, 15H, aromatic H).

MS: ($FAB^+$/G–T) m/z 867 $(2M+H)^+$, 431 $(M+H)^+$; ($FAB^-$/G–T) m/z 865 $(2M-H)^-$, 432 $(M-H)^-$.

| Analysis: $C_{26}H_{27}NO_3S_2$ (433) | | | | | | | |
|---|---|---|---|---|---|---|---|
| Calc. %: | C | 72.06 | H | 6.24 | N | 3.23 |
| Found %: | | 72.24 | | 6.22 | | 3.28 |

2.23. N-(N-isobutyryl-S-trityl-L-cysteinyl)-S-acetylcysteamine (14)

The coupling reaction of 13 (3.93 mmol) with S-acetylcysteamine hydrochloride is carried out according to method B described in the first synthetic route (example 1). After the various treatments, the expected compound is isolated by flash chromatography on a silica gel column (eluent: AcOEt/petroleum ether 60%). 14 is collected in the form of a colorless foam with a yield of 67%. $R_f$ (AcOEt/petroleum ether, 6/4): 0.5. $[\alpha]_D^{20}=+9.3°$ (c 0.97, $CHCl_3$).

$^1$H NMR $CDCl_3$) δ ppm: 1.10 (d, J=6.9 Hz, 6H, $C(CH_3)_2$), 2.18–2.36 (m, 1H, $CH(CH_3)_2$), 2.29 (s, 3H, $SCOCH_3$ partially concealing the m at 2.18–2.36), 2.50 (dd, J=5.6 and 12.8 Hz, 1H, β Ha cys), 2.72 (dd, J=6.7 and 12.8 Hz, 1H, β Hb cys), 2.88–3.01 (m, 2H, $NCH_2CH_2S$), 3.29–3.41 (m, 2H, $NCH_2CH_2S$), 4.06–4.19 (m, 1H, α H cys), 5.82 (d, J=7.4 Hz, 1H, NH cys), 6.42 (t, J=5.5 Hz, 1H, $NHCH_2$), 7.17–7.35, 7.39–7.48 (2m, 15H, aromatic H).

MS: ($FAB^+$/G–T) m/z 535 $(M+H)^+$.

| Analysis: $C_{30}H_{34}N_2O_3S$ (534) | | | | | | | |
|---|---|---|---|---|---|---|---|
| Calc. %: | C | 67.42 | H | 6.37 | N | 5.24 |
| Found %: | | 67.05 | | 6.72 | | 5.30 |

2.24. N-(N-isobutyryl-L-cysteinyl)-S-acetylcysteamine (I-203)

This compound is obtained by the S-detritylation of 14 (2.56 mmol). The protocol used is the same as that described in example 1 for the synthesis of I-152. After the various treatments, a gum is collected, which gum is purified by flash chromatography on a silica gel column (eluent: $CH_2Cl_2$/ether 30%). I-203 is isolated in the form of white solid with a yield of 70%. $R_f$ $CH_2Cl_2$/ether, 5/5): 0.44. M.p.=117–120° C. $[\alpha]_D^{20}=-36.5°$ (c 1.04, $CHCl_3$).

$^1$H NMR $CDCl_3$) δ ppm: 1.19, 1.20 (2d, J=2×6.9 Hz, 2×3H, $C(CH_3)_2$), 1.62 (dd, J=7.5 and 10.3 Hz, 1H, SH), 2.37 (s, 3H, $SCOCH_3$), 2.47 (hept, J=6.9 Hz, 1H, $CH(CH_3)_2$), 2.72 (ddd, J=6.5, 10.3 and 13.9 Hz, 1H, β Ha cys), 3.00–3.08 (m, 2H, $NCH_2CH_2S$), 3.06 (ddd, J=4.2, 7.5 and 13.9 Hz, 1H, β Hb cys), 3.41–3.53 (m, 2H, $NCH_2CH_2S$), 4.61 (ddd, J=4.2, 6.5 and 7.4 Hz, 1H, α H cys), 6.46 (d, J=7.4 Hz, 1H, NH cys), 6.72–6.85 (m, 1H, $NHCH_2$).

MS: ($FAB^+$/G–T) m/z 293 $(M+H)^+$.

| Analysis: $C_{11}H_{20}N_2O_3S_2$ (292) | | | | | | | |
|---|---|---|---|---|---|---|---|
| Calc. %: | C | 45.20 | H | 6.84 | N | 9.59 |
| Found %: | | 45.22 | | 7.11 | | 9.69 |

2.25. N-(N-isobutyryl-S-acetyl-L-cysteinyl)-S-acetylcysteamine (I-204)

The S-acylation of I-203 (0.34 mmol) with acetic anhydride is carried out according to the general method described in example 2. The reaction mixture is subsequently treated according to the protocol described for the synthesis of I-177. After the various treatments, a gum is collected, which gum is purified by flash chromatography on a silica gel column (eluent: $CH_2Cl_2$/ether 50%). I-204 is isolated in the semicrystalline form (Yd=75%), which product, after trituration in hexane provides a colorless powder. $R_f$ ($CH_2Cl_2$/ether, 2/8): 0.43. M.p.=125–127° C. $[\alpha]_D^{20}=-22.9°$ (c 1.05, $CHCl_3$).

$^1$H NMR $CDCl_3$) δ ppm: 1.16 (d, J=6.9 Hz, 6H, $C(CH_3)_2$), 2.34–2.47 (m, 1H, $CH(CH_3)_2$), 2.36, 2.38 (2s, 2×3H, 2×$SCOCH_3$ partially concealing the m at 2.34–2.47), 2.97–3.06 (m, 2H, $NCH_2CH_2S$), 3.26–3.32 (m, 2H, $CH_2$ cys), 3.38–3.48 (m, 2H, $NCH_2CH_2S$), 4.47–4.58 (m, 1H, α H cys), 6.39 (d, J=7.3 Hz, 1H, NH cys), 6.80–6.91 (m, 1H, $NHCH_2$).

MS: ($FAB^+$/G–T) m/z 669 $(2M+H)^+$, 335 $(M+H)^+$.

| Analysis: $C_{13}H_{22}N_2O_4S_2$ (334) | | | | | | | |
|---|---|---|---|---|---|---|---|
| Calc. %: | C | 46.71 | H | 6.59 | N | 8.38 |
| Found %: | | 46.76 | | 6.90 | | 8.35 |

2.26. N-(N,S-bisisobutyryl-L-cysteinyl)-S-acetylcysteamine (I-205)

The S-acylation of I-203 (0.32 mmol) with isobutyryl chloride is carried out according to the general method described in example 2. The reaction mixture is subsequently treated according to the protocol described for the synthesis of I-177. After the various treatments, an oil is collected, which oil is purified by flash chromatography on a silica gel column (eluent: AcOEt/petroleum ether 70%). I-205 is isolated in the form of a colorless gum (Yd=56%). $R_f$(AcOEt/petroleum ether, 4/6): 0.20. $[\alpha]_D^{20}=-17.3°$ (c 1.1, $CHCl_3$).

$^1$H NMR ($CDCl_3$) δ ppm: 1.16 (d, J=6.9 Hz, 6H, $C(CH_3)_2$ of N-i-but.), 1.20, 1.21 (2d, J=2×6.9 Hz, 2×3H, $C(CH_3)_2$ of S-i-but), 2.33–2.46 (m, 1H, $CH(CH_3)_2$ of N-i-but), 2.36 (s, 3H, $SCOCH_3$ partially concealing the m at 2.33–2.46); 2.79 (app. hept, J=6.9 Hz, 1H, $CH(CH_3)_2$ of S-i-but), 2.97–3.07 (m, 2H, $NCH_2CH_2S$), 3.25 (dd, J=5.0 and 13.8 Hz, 1H, β Ha cys), 3.32 (dd, J=7.5 and 13.8 H, 1H, β Hb cys), 3.38–3.48 (m, 2H, $NCH_2CH_2S$), 4.45–4.57 (m, 1H, α H cys), 6.44 (d, J=7.1 Hz, 1H, NH cys), 6.86–6.97 (m, 1H, $NHCH_2$).

MS: ($FAB^+$/G–T) m/z 725 $(2M+H)^+$, 363 $(M+H)^+$.

| Analysis: $C_{15}H_{26}N_2O_4S_2$ (362) | | | | | | | |
|---|---|---|---|---|---|---|---|
| Calc. %: | C | 49.72 | H | 7.18 | N | 7.73 |
| Found %: | | 49.87 | | 7.36 | | 7.80 |

2.27. N-(N-isobutyryl-S-pivaloyl-L-cysteinyl)-S-acetylcysteamine (I-206)

The S-acylation of I-203 (0.31 mmol) with pivaloyl chloride is carried out according to the general method described in example 2. The reaction mixture is subsequently treated according to the protocol described for the synthesis of I-177. After the various treatments, a gum is collected, which gum is purified by flash chromatography on a silica gel column (eluent: $CH_2Cl_2$/ether 50%). I-206 is isolated in the semicrystalline form (Yd=60%), which form, after trituration in hexane, provides a colorless powder. $R_f$ (AcOEt/petroleum ether, 4/6): 0.3. M.p.=101–103° C. $[\alpha]_D^{20}=-19.3°$ (c 1.09, $CHCl_3$).

$^1$H NMR ($CDCl_3$) δ ppm: 1.15 (d, J=6.9 Hz, 6H, $C(CH_3)_2$), 1.24 (s, 9H, $C(CH_3)_3$), 2.30–2.45 (m, 1H, $CH(CH_3)_2$), 2.36 (s, 3H, $SCOCH_3$ partially concealing the m at 2.30–2.45), 2.96–3.07 (m, 2H, $NCH_2CH_2S$), 3.23 (dd, J=5.3 and 13.8 Hz, 1H, β Ha cys), 3.30 (dd, J=6.9 and 13.8 Hz, 1H, β Hb cys), 3.37–3.49 (m, 2H, NCH$_2$CH$_2$S), 4.44–4.57 (m, 1H, α H cys), 6.44 (d, J=7.1 Hz, 1H, NH cys), 6.85–6.98 (m, 1H, NHCH$_2$).

MS: (FAB$^+$/G–T) m/z 753 (2M+H)$^+$, 377 (M+H)$^+$.

| Analysis: C$_{16}$H$_{28}$N$_2$O$_4$S$_2$ (376) | | | | | | |
|---|---|---|---|---|---|---|
| Calc. %: | C | 51.06 | H | 7.45 | N | 7.45 |
| Found %: | | 50.98 | | 7.72 | | 7.54 |

2.28. N-(N-isobutyryl-S-benzoyl-L-cysteinyl)-S-acetylcysteamine (I-207)

The S-acylation of I-203 (0.31 mmol) with benzoyl chloride is carried out according to the general method described in example 2. The reaction mixture is subsequently treated according to the protocol described for the synthesis of I-177. After the various treatments, a gum is collected, which gum is purified by flash chromatography on a silica gel column (eluent: AcOEt/petroleum ether 75%). I-207 is isolated in the form of a colorless solid (Yd=55%) which crystallizes from ether in colorless microcrystals. R$_f$ (CH$_2$Cl$_2$/ether, 7.5/2.5): 0.45. M.p.=135–137° C. [α]$_D^{20}$=+3.5° (c 1.16, CHCl$_3$).

$^1$H NMR (CDCl$_3$) δ ppm: 1.12, 1.14 (2d, J=2×6.9 Hz, 2×3H, C(CH$_3$)$_2$), 2.30–2.47 (m, 1H, CH(CH$_3$)$_2$), 2.33 (s, 3H, SCOCH$_3$ partially concealing the m at 2.30–2.47), 2.98–3.07 (m, 2H, NCH$_2$CH$_2$S), 3.40–3.58 (m, 4H, CH$_2$ cys, NCH$_2$CH$_2$S), 4.59–4.70 (m, 1H, α H cys), 6.59 (d, J=7.1 Hz, 1H, NH cys), 6.93–7.04 (m, 1H, NHCH$_2$), 7.41–7.53, 7.57–7.61, 7.92–8.01 (3m, 5H, aromatic H).

MS: (FAB$^+$/G–T) m/z 793 (2M+H)$^+$, 397 (M+H)$^+$.

| Analysis: C$_{18}$H$_{24}$N$_2$O$_4$S$_2$ (396) | | | | | | |
|---|---|---|---|---|---|---|
| Calc. %: | C | 54.54 | H | 6.06 | N | 7.07 |
| Found %: | | 54.51 | | 6.20 | | 7.07 |

2.29. N-(N-isobutyryl-S-trityl-L-cysteinyl)-S-isobutyrylcysteamine (15)

The coupling reaction of 13 (3.93 mmol) with S-isobutyrylcysteamine hydrochloride is carried out according to method B described in the first synthetic route (example 1). After the various treatments, the expected compound is isolated by flash chromatography on a silica gel column (eluent: AcOEt/petroleum ether 65%). 15 is collected in the form of a colorless foam with a yield of 75%. R$_f$ (AcOEt/petroleum ether, 5/5): 0.6. [α]$_D^{20}$=+7.9° (c 1.27, CHCl$_3$).

$^1$H NMR (CDCl$_3$) δ ppm: 1.107, 1.110, 1.159, 1.162 (4d, J=4×6.9 Hz, 4×3H, 2×C (CH$_3$) 2, 2.17–2.32 (m, 1H, CH(CH$_3$)$_2$ of N-i-but), 2.51 (dd, J=5.7 and 12.8 Hz, 1H, β Ha cys), 2.63–2.79 (m, 1H, CH(CH$_3$)$_2$ of S-i-but), 2.72 (dd, J=6.8 and 12.8 Hz, 1H, β Hb cys partially concealing the m at 2.63–2.79), 2.88–2.98 (m, 2H, NCH$_2$CH$_2$S), 3.29–3.40 (m, 2H, NCH$_2$CH$_2$S), 4.07–4.19 (m, 1H, α H cys), 5.81 (d, J=7.3 Hz, 1H, NH cys), 6.32–6.43 (m, 1H, NHCH$_2$), 7.18–7.35, 7.39–7.47 (2m, 15H, aromatic H).

MS: (FAB$^+$/G–T) m/z 563 (M+H)$^+$.

| Analysis: C$_{32}$H$_{38}$N$_2$O$_3$S$_2$ (562) | | | | | | |
|---|---|---|---|---|---|---|
| Calc. %: | C | 68.33 | H | 6.76 | N | 4.98 |
| Found %: | | 68.27 | | 6.71 | | 4.88 |

2.30. N-(N-isobutyryl-L-cysteinyl)-S-isobutyrylcysteamine (I-208)

This compound is obtained by the S-detritylation of 15 (2.75 mmol). The protocol used is the same as that described in example 1 for the synthesis of I-152. After the various treatments, a gum is collected, which gum is purified by flash chromatography on a silica gel column (eluent: CH$_2$Cl$_2$/ether 25%). I-208 is isolated in the form of a gum which, after trituration in hexane, provides a colorless powder (Yd=69%). R$_f$ (CH$_2$Cl$_2$/ether, 5/5): 0.39. M.p.=125–127° C. [α]$_D^{20}$=−25.7° (c 1.05, CHCl$_3$).

$^1$H NMR (CDCl$_3$) δ ppm: 1.19, 1.20 (2d, J=2×6.9 Hz, 2×6H, 2×C(CH$_3$)$_2$), 1.62. (dd, J=7.5 and 10.3 Hz, 1H, SH), 2.41–2.54 (m, 1H, CH(CH$_3$)$_2$ of N-i-but), 2.70–2.84 (m, 1H, CH(CH$_3$)$_2$ of S-i-but), 2.72 (ddd, J=6.5, 10.3 and 13.7 Hz, 1H, β Ha cys partially concealing the m at 2.70–2.84), 2.98–3.14 (m, 3H, β Hb cys, NCH$_2$CH$_2$S), 3.42–3.53 (m, 2H, NCH$_2$CH$_2$S), 4.54–4.66 (m, 1H, α H cys), 5.81 (d, J=7.4 Hz, 1H, NH cys), 6.74–6.85 (m, 1H, NHCH$_2$).

MS: (FAB$^+$/G–T) m/z 641 (2M+H)$^+$, 321 (M+H)$^+$.

| Analysis: C$_{13}$H$_{24}$N$_2$O$_3$S$_2$ (320) | | | | | | |
|---|---|---|---|---|---|---|
| Calc. %: | C | 48.75 | H | 7.50 | N | 8.75 |
| Found %: | | 48.45 | | 7.82 | | 8.75 |

2.31. N-(N-isobutyryl-S-acetyl-L-cysteinyl)-S-isobutyrylcysteamine (I-209)

The S-acylation of I-208 (0.28 mmol) with acetic anhydride is carried out according to the general method described in example 2. The reaction mixture is subsequently treated according to the protocol described for the synthesis of I-177. After the various treatments, a gum is collected, which gum, after triturations in hexane, provides a colorless powder which is homogeneous by TLC with a yield of 80%. R$_f$ (CH$_2$Cl$_2$/ether, 5/5): 0.55. M.p.=100–102° C. [α]$_D^{20}$=−22.9° (c 0.92, CHCl$_3$).

$^1$H NMR (CDCl$_3$) δ ppm: 1.15, 1.20 (2d, J=2×6.9 Hz, 2×6H, 2×C(CH$_3$)$_2$), 2.34–2.47 (m, 1H, CH(CH$_3$)$_2$ of N-i-but), 2.37 (s, 3H, SCOCH$_3$ partially concealing the m at 2.34–2.47), 2.69–2.82 (m, 1H, CH(CH$_3$)$_2$ of S-i-but), 2.95–3.05 (m, 2H, NCH$_2$CH$_2$S), 3.26–3.32 (m, 2H, CH$_2$ cys), 3.37–3.47 (m, 2H, NCH$_2$CH$_2$S), 4.47–4.59 (m, 1H, α H cys), 6.39 (d, J=7.1 Hz, 1H, NH cys), 6.79–6.90 (m, 1H, NHCH$_2$).

MS: (FAB$^+$/G–T) m/z 725 (2M+H)$^+$, 363 (M+H)$^+$.

| Analysis: C$_{15}$H$_{26}$N$_2$O$_4$S$_2$ (362) | | | | | | |
|---|---|---|---|---|---|---|
| Calc. %: | C | 49.72 | H | 7.18 | N | 7.73 |
| Found %: | | 49.47 | | 7.41 | | 7.70 |

2.31. N-(N,S-bisisobutyryl-L-cysteinyl)-S-isobutyrylcysteamine (I-210)

The S-acylation of I-208 (0.28 mmol) with isobutyryl chloride is carried out according to the general method described in example 2. The reaction mixture is subsequently treated according to the protocol described for the synthesis of I-177. After the various treatments, a gum is collected, which gum is purified by flash chromatography on a silica gel column (eluent: $CH_2Cl_2$/ether 25%). I-210 is isolated in the form of a gum which, after trituration in hexane, provides a colorless powder (Yd=63%). $R_f$ ($CH_2Cl_2$/ether, 5/5): 0.68. M.p.=94–96° C. $[\alpha]_D^{20}$=−11° (c 0.91, $CHCl_3$).

$^1$H NMR ($CDCl_3$) δ ppm: 1.154, 1.158, 1.199, 1.202 (4d, J=4×6.9 Hz, 2×3H, 2×6H, 3×C($CH_3$)$_2$), 2.32–2.46 (m, 1H, CH($CH_3$)$_2$ of N-i-but), 2.69–2.86 (m, 2H, 2×CH($CH_3$)$_2$ of 2×S-i-but), 2.93–3.07 (m, 2H, NCH$_2$CH$_2$S), 3.25 (dd, J=5.0 and 14.5 Hz, 1H, β Ha cys), 3.32 (dd, J=7.7 and 14.5 Hz, 1H, β Hb cys), 3.38–3.47 (m, 2H, NCH$_2$CH$_2$S), 4.45–4.56 (m, 1H, α H cys), 6.42 (d, J=7.4 Hz, 1H, NH cys), 6.82–6.92 (m, 1H, NHCH$_2$).

MS: (FAB$^+$/G–T) m/z 781 (2M+H)$^+$, 391 (M+H)$^+$.

| Analysis: $C_{17}H_{30}N_2O_4S_2$ (390) | | | | | | |
|---|---|---|---|---|---|---|
| Calc. %: | C | 52.31 | H | 7.69 | N | 7.18 |
| Found %: |   | 52.02 |   | 8.02 |   | 7.21 |

2.32. N-(N-isobutyryl-S-benzoyl-L-cysteinyl)-S-isobutyrylcysteamine (I-211)

The S-acylation of I-208 (0.29 mmol) with benzoyl chloride is carried out according to the general method described in example 2. The reaction mixture is subsequently treated according to the protocol described for the synthesis of I-177. After the various treatments, a gum is collected, which gum is purified by flash chromatography on a silica gel column (eluent: $CH_2Cl_2$/ether 35%). I-210 is isolated in the form of a gum which, after trituration in petroleum ether, provides a colorless powder (Yd=86%). $R_f$ ($CH_2Cl_2$/ether, 6/4): 0.52. M.p.=155–157° C. $[\alpha]_D^{20}$=+7.0° (c 1, $CHCl_3$).

$^1$H NMR ($CDCl_3$) δ ppm: 1.12, 1.15, 1.18 (3d, J=3×6.9 Hz, 2×3H, 1×6H, 2×C($CH_3$)$_2$), 2.36–2.46 (m, 1H, CH($CH_3$)$_2$ of N-i-but), 2.68–2.80 (m, 1H, CH($CH_3$)$_2$ of S-i-but), 2.95–3.05 (m, 2H, NCH$_2$CH$_2$S), 3.40–3.62 (m, 4H, CH$_2$ cys, NCH$_2$CH$_2$S), 4.56–4.69 (m, 1H, α H cys), 6.54 (d, J=7.0 Hz, 1H, NH cys), 6.84–6.95 (m, 1H, NHCH$_2$), 7.42–7.51, 7.57–7.65, 7.94–8.01 (m, 5H, aromatic H).

MS: (FAB$^+$/G–T) m/z 894 (2M+H)$^+$, 425 (M+H)$^+$.

| Analysis: $C_{20}H_{28}N_2O_4S_2$ (424) | | | | | | |
|---|---|---|---|---|---|---|
| Calc. %: | C | 56.60 | H | 6.60 | N | 6.60 |
| Found %: |   | 56.42 |   | 6.79 |   | 6.63 |

2.33. N-(N-isobutyryl-S-trityl-L-cysteinyl)-S-pivaloylcysteamine (16)

The coupling reaction of 13 (3.93 mmol) of S-pivaloylcysteamine hydrochloride is carried out according to method B described in the first synthetic route (example 1). After the various treatments, the expected compound is isolated by flash chromatography on a silica gel column (eluent: AcOEt/petroleum ether 70%). 16 is collected in the form of a foam which, after trituration in hexane, provides a colorless powder (Yd=88%). $R_f$ ($CH_2Cl_2$/ether, 6/4): 0.82. M.p.=85–88° C. $[\alpha]_D^{20}$=+5.9° (c 1.02, $CHCl_3$).

$^1$H NMR ($CDCl_3$) δ ppm: 1.11 (d, J=6.9 Hz, 6H, C($CH_3$)$_2$), 1.21 (s, 9H, C($CH_3$)$_3$), 2.20–2.38 (m, 1H, CH($CH_3$)$_2$), 2.51 (dd, J=5.6 and 12.9 Hz, 1H, β Ha cys), 2.72 (dd, J=6.7 and 12.9 Hz, 1H, β Hb cys), 2.84–2.96 (m, 2H, NCH$_2$CH$_2$S), 3.27–3.39 (m, 2H, NCH$_2$CH$_2$S), 4.03–4.17 (m, 1H, α H cys), 5.78 (d, J=7.4 Hz, 1H, NH cys), 6.22–6.34 (m, 1H, NHCH$_2$), 7.18–7.35, 7.38–7.48 (2m, 15H, aromatic H).

MS: (FAB$^+$/G–T) m/z 577 (M+H)$^+$.

| Analysis: $C_{33}H_{40}N_2O_3S_2$ (576) | | | | | | |
|---|---|---|---|---|---|---|
| Calc. %: | C | 68.75 | H | 6.94 | N | 4.86 |
| Found %: |   | 68.49 |   | 6.98 |   | 4.93 |

2.34. N-(N-isobutyryl-L-cysteinyl)-S-pivaloylcysteamine (I-214)

This compound is obtained by the S-detritylation of 16 (2.78 mmol). The protocol used is the same as that described in example 1 for the synthesis of I-152. After the various treatments, a gum is collected, which gum is purified by flash chromatography on a silica gel column (eluent: $CH_2Cl_2$/ether 22%). I-214 is isolated in the form of a gum which, after trituration in hexane, provides a colorless powder (Yd=70%). $R_f$ ($CH_2Cl_2$/ether, 5/5): 0.46. M.p.=120–122° C. $[\alpha]_D^{20}$=−25° (c 1.04, $CHCl_3$).

$^1$H NMR ($CDCl_3$) δ ppm: 1.194, 1.198 (2d, J=2×6.9 Hz, 2×3H, C($CH_3$)$_2$), 1.23 (s, 9H, C($CH_3$)$_3$), 1.61 (dd, J=7.6 and 10.2 Hz, 1H, SH), 2.47 (app. hept, J=6.9 Hz, 1H, CH($CH_3$)$_2$), 2.72 (ddd, J=6.5, 10.2 and 13.8 Hz, 1H, β Ha cys), 2.95–3.13 (m, 3H, β Hb cys, NCH$_2$CH$_2$S), 3.40–3.52 (m, 2H, NCH$_2$CH$_2$S), 4.54–4.66 (m, 1H, α H cys), 6.49 (d, J=7.5 Hz, 1H, NH cys), 6.73–6.88 (m, 1H, NHCH$_2$).

MS: (FAB$^+$/G–T) m/z 669 (2M+H)$^+$, 335 (M+H)$^+$.

| Analysis: $C_{14}H_{26}N_2O_3S_2$ (334) | | | | | | |
|---|---|---|---|---|---|---|
| Calc. %: | C | 50.30 | H | 7.78 | N | 8.38 |
| Found %: |   | 50.19 |   | 7.92 |   | 8.35 |

2.35. N-(N-isobutyryl-S-acetyl-L-cysteinyl)-S-pivaloylcysteamine (I-215)

The S-acylation of I-214 (0.27 mmol) with acetic anhydride is carried out according to the general method described in example 2. The reaction mixture is subsequently treated according to the protocol described for the synthesis of I-177. After the various treatments, a gum is collected, which gum, after triturations in hexane, provides a colorless powder which is homogeneous by TLC with a yield of 80%. $R_f$ ($CH_2Cl_2$/ether, 6/4): 0.45. M.p.=112–114° C. $[\alpha]_D^{20}$=−18.8° (c 0.9, $CHCl_3$)

$^1$H NMR ($CDCl_3$) δ ppm: 1.16 (d, J=6.9 Hz, 6H, C($CH_3$)$_2$), 1.24 (s, 9H, C($CH_3$)$_3$), 2.31–2.49 (m, 1H, CH($CH_3$)$_2$), 2.37. (s, 3H, SCOCH$_3$ partially concealing the m at 2.31–2.49), 2.88–3.08 (m, 2H, NCH$_2$CH$_2$S), 3.25–3.34 (m, 2H, CH$_2$ cys), 3.35–3.47 (m, 2H, NCH$_2$CH$_2$S), 4.48–4.60 (m, 1H, α H cys), 6.38 (d, J=7.3 Hz, 1H, NH cys), 6.74–6.89 (m, 1H, NHCH$_2$).

MS: (FAB$^+$/G–T) m/z 377 (M+H)$^+$.

| Analysis: $C_{15}H_{28}N_2O_4S_2$ (376) | | | | | | |
|---|---|---|---|---|---|---|
| Calc. %: | C | 51.06 | H | 7.45 | N | 7.45 |
| Found %: |   | 50.97 |   | 7.81 |   | 7.47 |

2.36. N-(N,S-bisisobutyryl-L-cysteinyl)-S-pivaloylcysteamine (I-216)

The S-acylation of I-214 (0.26 mmol) with isobutyryl chloride is carried out according to the general method described in example 2. The reaction mixture is subsequently treated according to the protocol described for the synthesis of I-177. After the various treatments, a gum is collected, which gum is purified by flash chromatography on a silica gel column (eluent: $CH_2Cl_2$/ether 15%). I-216 is isolated in the form of a gum which, after trituration in hexane, provides a colorless powder (Yd=78%). $R_f$ ($CH_2Cl_2$/ether, 6/4): 0.61. M.p.=105–107° C. $[\alpha]_D^{20}$=−12.2° (c 1.07, $CHCl_3$).

$^1$H NMR ($CDCl_3$) δ ppm: 1.154, 1.157, 1.196, 1.201 (4d, J=4×6.9 Hz, 4×3H, 2×C($CH_3$)$_2$), 1.24 (s,. 9H, C($CH_3$)$_3$), 2.39 (app. hept, J=6.9 Hz, 1H, CH($CH_3$)$_2$ of N-i-but), 2.79 (app. hept, J=6.9 Hz, 1H, CH($CH_3$)$_2$ of S-i-but), 2.87–3.08 (m, 2H, N$CH_2$$CH_2$S), 3.25 (dd, J=5.2 and 14.5 Hz, 1H, β Ha cys), 3.32 (dd, J=7.5 and 14.5 Hz, 1H, β Hb cys), 3.37–3.47 (m, 2H, N$CH_2$$CH_2$S), 4.46–4.59 (m, 1H, α H cys), 6.43 (d, J=7.0 Hz, 1H, NH cys), 6.81–6.93 (m, 1H, N$HCH_2$).

MS: (FAB$^+$/G–T) m/z 809 (2M+H)$^+$, 405 (M+H)$^+$.

| Analysis: $C_{18}H_{32}N_2O_4S_2$ (404) | | | | | |
|---|---|---|---|---|---|
| Calc. %: | C | 53.47 | H | 7.92 | N | 6.93 |
| Found %: |  | 53.33 |  | 8.09 |  | 6.95 |

2.37. N-(N-isobutyryl-S-pivaloyl-L-cysteinyl)-S-pivaloylcysteamine (I-217)

The S-acylation of I-214 (0.26 mmol) with pivaloyl chloride is carried out according to the general method described in example 2. The reaction mixture is subsequently treated according to the protocol described for the synthesis of I-177. After the various treatments, a gum is collected, which gum, after triturations in hexane, provides a colorless powder which is homogeneous by TLC with a yield of 55%. $R_f$ ($CH_2Cl_2$/ether, 6/4): 0.63. M.p.=106–108° C. $[\alpha]_D^{20}$=−10.2° (c 1.18, $CHCl_3$).

$^1$H NMR ($CDCl_3$) δ ppm: 1.151, 1.157 (2d, J=2×6.9 Hz, 2×3H, C($CH_3$)$_2$), 1.240, 1.244 (2s, 2×9H, 2×C($CH_3$)$_3$), 2.38 (app. hept, J=6.9 Hz, 1H, CH($CH_3$)$_2$), 2.86–3.07 (m, 2H, N$CH_2$$CH_2$S), 3.24 (dd, J=5.0 and 14.2 Hz, 1H, β Ha cys), 3.30 (dd, J=6.5 and 14.2 Hz, 1H, β Hb cys), 3.33–3.48 (m, 2H, N$CH_2$$CH_2$S), 4.42–4.54 (m, 1H, α H cys), 6.39 (d, J=7.0 Hz, 1H, NH cys), 6.74–6.86 (m, 1H, N$HCH_2$).

MS: (FAB$^+$/G–T) m/z 837 (2M+H)$^+$, 419 (M+H)$^+$.

| Analysis: $C_{19}H_{34}N_2O_4S_2$ (418) | | | | | |
|---|---|---|---|---|---|
| Calc. %: | C | 54.81 | H | 8.17 | N | 6.73 |
| Found %: |  | 54.50 |  | 8.27 |  | 6.74 |

2.38. N-(N-isobutyryl-S-benzoyl-L-cysteinyl)-S-pivaloylcysteamine (I-218)

The S-acylation of I-214 (0.26 mmol) with benzoyl chloride is carried out according to the general method described in example 2. The reaction mixture is subsequently treated according to the protocol described for the synthesis of I-177. After the various treatments, a gum is collected, which gum is purified by flash chromatography on a silica gel column (eluent: $CH_2Cl_2$/ether 25%). I-218 is isolated in the form of a gum which, after trituration in hexane, provides a colorless powder (Yd=73%). $R_f$($CH_2Cl_2$/ether, 5/5): 0.57. M.p.=123–124° C. $[\alpha]_D^{20}$=+8.7° (c 0.92, $CHCl_3$).

$^1$H NMR ($CDCl_3$) δ ppm: 1.12, 1.14 (2d, J=2×6.9 Hz, 2×3H, C($CH_3$)$_2$), 1.22 (s, 9H, C($CH_3$)$_3$), 2.40 (app. hept, J=6.9 Hz, 1H, CH($CH_3$)$_2$), 2.89–3.09 (m, 2H, N$CH_2$$CH_2$S), 3.37–3.61 (m, 4H, N$CH_2$$CH_2$S, $CH_2$ cys), 4.57–4.70 (m, 1H, α H cys), 6.55 (d, J=7.3 Hz, 1H, NH cys), 6.84–6.94 (m, 1H, N$HCH_2$), 7.41–7.52, 7.55–7.66, 7.92–8.01 (3m, 5H, aromatic H).

MS: (FAB$^+$/G–T) m/z 877 (2M+H)$^+$, 439 (M+H)$^+$.

| Analysis: $C_{21}H_{30}N_2O_4S_2$ (438) | | | | | |
|---|---|---|---|---|---|
| Calc. %: | C | 57.53 | H | 6.85 | N | 6.39 |
| Found %: |  | 57.53 |  | 6.89 |  | 6.37 |

2.39. N-(N-isobutyryl-S-trityl-L-cysteinyl)-S-benzoylcysteamine (17)

The coupling reaction of 13 (3.93 mmol) with S-benzoylcysteamine hydrochloride is carried out according to method B described in the first synthetic route (example 1). After the various treatments, the expected compound is isolated by flash chromatography on a silica gel column (eluent: AcOEt/petroleum ether 70%). 17 is collected in the form of a foam which, after trituration in hexane, provides a colorless foam (Yd=77%). $R_f$ ($CH_2Cl_2$/ether, 6/4): 0.76. $[\alpha]_D^{20}$=+7.8° (c 1.03, $CHCl_3$).

$^1$H NMR ($CDCl_3$) δ ppm: 1.09 (d, J=6.9 Hz, 6H, C($CH_3$)$_2$), 2.18–2.31 (m, 1H, CH($CH_3$)$_2$), 2.51 (dd, J=5.6 and 12.9 Hz, 1H, β Ha cys), 2.74 (dd, J=6.7 and 12.9 Hz, 1H, β Hb cys), 3.07–3.25 (m, 2H, N$CH_2$$CH_2$S), 3.40–3.51 (m, 2H, N$CH_2$$CH_2$S), 4.07–4.19 (m, 1H, α H cys), 5.74 (d, J=7.6 Hz, 1H, NH cys), 6.35–6.45 (m, 1H, N$HCH_2$), 7.17–7.33, 7.38–7.47, 7.53–7.62, 7.89–7.96 (4m, 20H, aromatic H).

MS: (FAB$^+$/G–T) m/z 597 (M+H)$^+$.

| Analysis: $C_{35}H_{36}N_2O_3S_2$ (596) | | | | | |
|---|---|---|---|---|---|
| Calc. %: | C | 70.47 | H | 6.04 | N | 4.70 |
| Found %: |  | 70.14 |  | 6.10 |  | 4.79 |

2.40. N-(N-isobutyryl-L-cysteinyl)-S-benzoylcysteamine (I-219)

This compound is obtained by the S-detritylation of 17 (2.68 mmol). The protocol used is the same as that described in example 1 for the synthesis of I-152. After the various treatments, a gum is collected, which gum is purified by flash chromatography on a silica gel column (eluent: $CH_2Cl_2$/ether 25%). I-219 is isolated in the form of a gum which, after trituration in hexane, provides a colorless powder (Yd=58%). $R_f$ ($CH_2Cl_2$/ether, 6/4): 0.35. M.p.= 127–130° C. $[\alpha]_D^{20}$=−20.8° (c 1.06, $CHCl_3$).

$^1$H NMR ($CDCl_3$) δ ppm: 1.17, 1.18 (2d, J=2×6.9 Hz, 2×3H, C($CH_3$)$_2$), 1.59 (dd, J=7.5 and 10.3 Hz, 1H, SH), 2.44 (app. hept, J=6.9 Hz, 1H, CH($CH_3$)$_2$), 2.70 (ddd, J=6.5, 10.3 and 13.8 Hz, 1H, β Ha cys), 3.07 (ddd, J=4.2, 7.5 and 13.8 Hz, 1H, β Hb cys), 3.17–3.34 (m, 2H, N$CH_2$$CH_2$S), 3.53–3.64 (m, 2H, N$CH_2$$CH_2$S), 4.62 (ddd, J=4.2, 6.5 and 8.0 Hz, 1H, α H cys), 6.47 (d, J=8.0 Hz, 1H, NH cys), 6.80–6.91 (m, 1H, N$HCH_2$), 7.42–7.53, 7.56–7.65, 7.92–8.01 (3m, 5H, aromatic H).

MS: (FAB$^+$/G–T) m/z 709 (2M+H)$^+$, 355 (M+H)$^+$.

| Analysis: $C_{16}H_{22}N_2O_3S_2$ (354) | | | | | | |
|---|---|---|---|---|---|---|
| Calc. %: | C | 54.23 | H | 6.21 | N | 7.91 |
| Found %: |  | 54.20 |  | 6.18 |  | 7.94 |

2.41. N-(N-isobutyryl-S-acetyl-L-cysteinyl)-S-benzoylcysteamine (I-220)

The S-acylation of I-219 (0.25 mmol) with acetic anhydride is carried out according to the general method described in example 2. The reaction mixture is subsequently treated according to the protocol described for the synthesis of I-177. After the various treatments, a gum is collected, which gum is purified by flash chromatography on a silica gel column (eluent: $CH_2Cl_2$/ether 15%). I-220 is isolated in the form of a gum which, after trituration in hexane, provides a colorless powder (Yd=70%). $R_f$ ($CH_2Cl_2$/ether, 7.5/2.5): 0.43. M.p.=174–176° C. $[\alpha]_D^{20}$=−17.6° (c 0.91, $CHCl_3$).

$^1$H NMR ($CDCl_3$) δ ppm: 1.13, 1.14 (2d, J=2×6.9 Hz, 2×3H, C(CH$_3$)$_2$), 2.29–2.45 (m, 1H, CH(CH$_3$)$_2$), 2.32 (s, 3H, SCOCH$_3$ partially concealing the m at 2.29–2.45), 3.18–3.38 (m, 4H, NCH$_2$CH$_2$S, CH$_2$ cys), 3.45–3.62 (m, 2H, NCH$_2$CH$_2$S), 4.50–4.62 (m, 1H, α H cys), 6.39 (d, J=7.1 Hz, 1H, NH cys), 6.88–6.98 (m, 1H, NHCH$_2$), 7.42–7.52, 7.55–7.64, 7.92–8.01 (3m, 5H, aromatic H).

MS: (FAB$^+$/G–T) m/z 793 (2M+H)$^+$, 397 (M+H)$^+$.

| Analysis: $C_{18}H_{24}N_2O_4S_2$ (396) | | | | | | |
|---|---|---|---|---|---|---|
| Calc. %: | C | 54.54 | H | 6.06 | N | 7.07 |
| Found %: |  | 54.46 |  | 6.02 |  | 7.08 |

2.42. N-(N,S-bisisobutyryl-L-cysteinyl)-S-benzoylcysteamine (I-221)

The S-acylation of I-219 (0.25 mmol) with isobutyryl chloride is carried out according to the general method described in example 2. The reaction mixture is subsequently treated according to the protocol described for the synthesis of I-177. After the various treatments, a gum is collected, which gum, after triturations in hexane, provides a colorless powder which is homogeneous by TLC with a yield of 86%. $R_f$ ($CH_2Cl_2$/ether, 7.5/2.5): 0.42. M.p.=141–143° C. $[\alpha]_D^{20}$=−9° (c 1.11, $CHCl_3$).

$^1$H NMR ($CDCl_3$) δ ppm: 1.13, 1.14 (2d, J=2×6.9 Hz, 2×3H, C(CH$_3$)$_2$ of N-i-but), 1.18 (d, J=6.9 Hz, 6H, C(CH$_3$)$_2$ of S-i-but), 2.37 (app. hept, J=6.9 Hz, 1H, CH(CH$_3$)$_2$ of N-i-but), 2.75 (app. hept, J=6.9 Hz, 1H, CH(CH$_3$)$_2$ of S-i-but), 3.16–3.38 (m, 4H, CH$_2$ cys, NCH$_2$CH$_2$S), 3.42–3.64 (m, 2H, NCH$_2$CH$_2$S), 4.47–4.58 (m, 1H, α H cys), 6.42 (d, J=7.0 Hz, 1H, NH cys), 6.87–7.01 (m, 1H, NHCH$_2$), 7.41–7.50, 7.55–7.63, 7.93–8.01 (3m, 5H, aromatic H).

MS: (FAB$^+$/G–T) m/z 849 (2M+H)$^+$, 425 (M+H)$^+$.

| Analysis: $C_{20}H_{28}N_2O_4S_2$ (424) | | | | | | |
|---|---|---|---|---|---|---|
| Calc. %: | C | 56.60 | H | 6.60 | N | 6.60 |
| Found %: |  | 56.67 |  | 6.62 |  | 6.63 |

2.43. N-(N-isobutyryl-S-pivaloyl-L-cysteinyl)-S-benzoylcysteamine (I-222)

The S-acylation of I-219 (0.25 mmol) with pivaloyl chloride is carried out according to the general method described in example 2. The reaction mixture is subsequently treated according to the protocol described for the synthesis of I-177. After the various treatments, a gum is collected, which gum is purified by flash chromatography on a silica gel column (eluent: $CH_2Cl_2$/ether 20%). I-222 is isolated in the form of a gum (Yd=50%) which, after trituration in hexane, provides a colorless powder. $R_f$ ($CH_2Cl_2$/ether, 5/5): 0.55. M.p.=112–114° C. $[\alpha]_D^{20}$=+4.60 (c 1.08, $CHCl_3$).

$^1$H NMR ($CDCl_3$) δ ppm: 1.12, 1.13 (2d, J=2×6.9 Hz, 2×3H, C(CH$_3$)$_2$), 1.22 (s, 9H, C(CH$_3$)$_3$), 2.36 (app. hept, J=6.9 Hz, 1H, CH(CH$_3$)$_2$), 3.18–3.36 (m, 4H, CH$_2$ cys, NCH$_2$CH$_2$S), 3.45–3.62 (m, 2H, NCH$_2$CH$_2$S), 4.48–4.60 (m, 1H, α H cys), 6.48 (d, J=7.2 Hz, 1H, NH cys), 6.96–7.08 (m, 1H, NHCH$_2$), 7.40–7.51, 7.54–7.63, 7.92–8.01 (3m, 5H, aromatic H).

MS: (FAB$^+$/G–T) m/z 877 (2M+H)$^+$, 439 (M+H)$^+$.

| Analysis: $C_{21}H_{30}N_2O_4S_2$ (438) | | | | | | |
|---|---|---|---|---|---|---|
| Calc. %: | C | 57.53 | H | 6.85 | N | 6.39 |
| Found %: |  | 57.31 |  | 6.86 |  | 6.34 |

2.44. N-(N-isobutyryl-S-benzoyl-L-cysteinyl)-S-benzoylcysteamine (I-223)

The S-acylation of I-219 (0.26 mmol) with benzoyl chloride is carried out according to the general method described in example 2. The reaction mixture is subsequently treated according to the protocol described for the synthesis of I-177. After the various treatments, a gum is collected, which gum is purified by flash chromatography on a silica gel column (eluent: $CH_2Cl_2$/ether 20%). I-223 is isolated in the form of a gum (Yd=84%) which, after trituration in hexane, provides a colorless powder. $R_f$($CH_2Cl_2$/ether, 7:3): 0.41. M.p.=154–156° C. $[\alpha]_D^{20}$=+7.6° (c 0.92; $CHCl_3$).

$^1$H NMR ($CDCl_3$) δ ppm: 1.10, 1.11 (2d, J=2×6.9 Hz, 2×3H, C(CH$_3$)$_2$), 2.38 (app. hept, J=6.9 Hz, 1H, CH(CH$_3$)$_2$), 3.19–3.28 (m, 2H, NCH$_2$CH$_2$S), 3.43–3.64 (m, 4H, CH$_2$ cys, NCH$_2$CH$_2$S), 4.58–4.71 (m, 1H, α H cys), 6.55 (d, J=7.2 Hz, 1H, NH cys), 6.92–7.01 (m, 1H, NHCH$_2$), 7.39–7.50, 7.53–7.64, 7.91–7.99 (3m, 10H, aromatic H).

MS: (FAB$^+$/G–T) m/z 917 (2M+H)$^+$, 459 (M+H)$^+$.

| Analysis: $C_{23}H_{26}N_2O_4S_2$ (458) | | | | | | |
|---|---|---|---|---|---|---|
| Calc. %: | C | 60.26 | H | 5.68 | N | 6.11 |
| Found %: |  | 60.22 |  | 5.67 |  | 6.00 |

2.45. N-(N-acetyl-S-trityl-L-cysteinyl)thiazolidine (18)

The coupling reaction of 7 (2 mmol) with thiazolidine is carried out according to method A described in the first synthetic route (example 1). After returning to ambient temperature, stirring is continued for 12 h. The reaction medium is then diluted with 50 ml of AcOEt, then washed (water, 70 ml; ice-cold saturated sodium bicarbonate, 50 ml; water, 2×50 ml), dried over sodium sulfate and evaporated to dryness under vacuum. The colorless foam obtained is subsequently purified by flash chromatography on a silica gel column (eluent: AcOEt/petroleum ether 30%). 18 is isolated in the form of a colorless gum with a yield of 80%. $R_f$ (AcOEt/petroleum ether, 8/2): 0.40. Crystallizes from MeOH in colorless needles. M.p.=197–198° C. $[\alpha]_D^{20}$=+0.86° (c 1.16, $CHCl_3$).

$^1$H NMR ($CDCl_3$) δ ppm (isomeric mixture, 5.2/4.8: 1.95 (s, 3H, NCOCH$_3$), 2.48–2.66 (m, 2H, CH$_2$ cys), 2.88–3.02

(m, 2H, H5, H5' Thz), 3.24–3.34, 3.64–3.75, 3.77–3.86 (3m, 2H, H4, H4' Thz), 3.96, 4.41 and 4.45, 4.54 (2×2d, J=2×8.8 and 2×10.3 Hz, 2H, H2, H2' Thz), 4.60–4.69 (m, 1H, α H cys), 6.05–6.15 (m, 1H, NH cys), 7.18–7.34, 7.36–7.44 (2m, 15H, aromatic H).

MS: (FAB$^+$/G–T) m/z 953 (2M+H)$^+$, 477 (M+H)$^+$.

| Analysis: $C_{27}H_{28}N_2O_2S_2$ (476) | | | |
|---|---|---|---|
| Calc. %: | C 68.07 | H 5.88 | N 5.88 |
| Found %: | 67.97 | 5.84 | 5.89 |

2.46. N-(N-acetyl-L-cysteinyl)thiazolidine (I-212)

This compound is obtained by the S-detritylation of 1.8 (0.77 mmol). The protocol used is the same as that described in example 1 for the synthesis of I-152. After stirring overnight at ambient temperature, a solution is obtained. This solution is evaporated to dryness under vacuum and the pasty residue obtained is coevaporated with toluene (3×5 ml) and then washed with 4×15 ml of ether to provide the corresponding silver sulfide in the form of a yellow powder. This sulfide is subsequently treated in the same way as that described in example 1. After the various treatments, a translucent gum is collected, which gum is purified by flash chromatography on a silica gel column (eluent: AcOEt). I-212 is isolated in the form of a colorless gum with a yield of 64%. R$_f$ (AcOEt/MeOH, 9.7/0.3): 0.40. Crystallizes from an AcOEt/hexane mixture in the form of colorless needles. M.p.=90–91° C. [α]$_D^{20}$=–31° (c 1, CHCl$_3$).

$^1$H NMR (CDCl$_3$) δ ppm (isomeric mixture, 5.8/4.2): 1.55 (app. t, J=8.9 Hz, 1H, SH), 2.02 (s, 3H, NCOCH$_3$), 2.75–2.84, 2.85–2.95 (2m, 2H, CH$_2$ cys), 2.99–3.18 (m, 2H, H5, H5' Thz), 3.79–4.03 (m, 2H, H4, H4' Thz), 4.57, 4.63 and 4.71 (2d, J=2×10.4 and 1 app. s, 2H, H2, H2' Thz), 4.94–5.04 (m, 1H, α H cys), 6.41–6.52 (m, 1H, NH cys).

MS: (FAB$^+$/G–T) m/z 235 (M+H)$^+$.

| Analysis: $C_8H_{14}N_2O_2S_2$ (234) | | | |
|---|---|---|---|
| Calc. %: | C 41.03 | H 5.98 | N 11.97 |
| Found %: | 41.12 | 6.01 | 11.96 |

2.47. N-(N,S-bisacetyl-L-cysteinyl)thiazolidine (I-213)

The S-acylation of I-212 (0.26 mmol) with acetic anhydride is carried out according to the general method described in example 2. The reaction mixture is subsequently treated according to the protocol described for the synthesis of I-177. After the various treatments, a gum is collected, which gum is purified by flash chromatography on a silica gel column (eluent: AcOEt/petroleum ether 10%). I-213 is isolated in the form of a gum (Yd=80%) which crystallizes from an AcOEt/petroleum ether mixture in colorless needles. R$_f$ (AcOEt): 0.3, M.p. 107–108° C. [α]$_D^{20}$=+6.6° (c 1.36, CHCl$_3$).

$^1$H NMR (CDCl$_3$) δ ppm (isomeric mixture, 5.9/4.1): 2.01 (s, 3H, NCOCH$_3$), 2.36 (s, 3H, SCOCH$_3$), 2.97–3.20, 3.26–3.29, 3.30–3.33 (3m, 4H, CH$_2$ cys, H5, HS' Thz), 3.73–3.81, 3.82–3.89, 3.96–4.06 (3m, 2H, H4, H4' Thz), 4.49, 4.61, 4.71, 4.81 (2×2d, J=2×10.3 and 2×8.9 Hz, 2H, H2, H2', Thz), 4.93–5.04 (m, 1H, α H cys), 6.39–6.50 (m, 1H, NH cys).

MS: (FAB$^+$/G–T) m/z 553 (2M+H)$^+$, 277 (M+H)$^+$.

| Analysis: $C_{10}H_{16}N_2O_2S_2$ (276) | | | |
|---|---|---|---|
| Calc. %: | C 43.48 | H 5.80 | N 10.14 |

EXAMPLE 3

Demonstration of Antiviral Activity of Compounds Obtained in Examples 1 and 2

3.1. Preamble

The manipulations of infectious material have been performed in a L3 type high security laboratory.

In order to approximate as closely as possible to physiopathological conditions, all the studies were carried out using MDM, PBMC or PBL primary cultures obtained from healthy blood donors.

In all the experiments, the effects of the novel molecules were compared with those of the reference molecules: NAC or MEA.

3.2. Isolation, Culturing and Activation of the Cells 3.2.1. Culture Media

The medium A is composed of RPMI 1640 cell culture medium (Life Technologies) supplemented with 10% of fetal calf serum (FCS, Boehringer Mannheim) heat decomplemented at 56° C. for 30 min, of 2 mM of L-glutamine (Boehringer Mannheim) and of a 100 μg/ml solution of 3 antibiotics (penicillin, streptomycin and neomycin; PSN, Life Technologies). The medium B is composed of medium A supplemented with 20 IU/ml of recombinant human IL-2 (Boehringer Mannheim).

3.2.2 Isolation of the Peripheral Blood Mononuclear Cells

The PBMCs are separated from the other components which appear in the blood by centrifugation on a Ficoll gradient (MSL 2000, Eurobio): 30 ml of blood from a healthy donor, diluted to a third, are deposited on a 20 ml cushion of Ficoll. After centrifuging for 20 min at 850 g, the band of PBMC is removed and then washed twice in RPMI 1640, after centrifuging for 10 min at 750 g and 5 min at 400 g.

3.2.3. Isolation of the Monocytes and Lymphocytes

The monocytes and the lymphocytes are isolated from the PBMCs by countercurrent elutriation according to the protocol described by C. Figdor et al. (*Cell. Biophys.*, 1983, 5, 105–118). The two cell populations thus separated are immunophenotyped and then analyzed using a flow cytometer (FACScan, Becton Dickinson). The purity of the monocytes and PLBs thus obtained is greater than or equal to 95%.

3.2.4. Culturing and Activation of the Cells

A million monocytes in 1 ml of culture medium A are distributed in each well of a 48 well plate (Becton-Dickinson). The monocytes are left to differentiate into macrophages for 7 days. The macrophages thus differentiated are maintained in culture in medium A.

For some experiments, the PBMCs and the PBLs are activated for 48 h with 1 μg/ml of a mitogen, PHA-P (Difco Laboratories). The PBMCs and the PBLs are cultured in medium A (quiescent) or B (activated). The cells are cultured at 37° C. in an atmosphere saturated with moisture under 5% of CO$_2$. The culture supernatants are removed and the culture media are replaced every three or four days. At each renewal of the culture media, the cell viability is evaluated by coloring with trypan blue or by microscopic observation.

3.3. Evaluation of the Antiviral Activity of I-152 and of its Derivatives

3.3.1. Preparation of the Compounds

During the first series for evaluation of the antiviral activity and during the study of the mechanism of action of I-152, I-152 and the reference products were dissolved in medium A. The molecules were resuspended at stock concentrations (NAC: 20 mM, MEA and I-152: 10 mM) and were stored at −80° C. The dilutions were subsequently prepared extemporaneously in medium A.

During the second series for evaluation of the antiviral activity, I-152 and its derivatives (insoluble in medium A) were dissolved in DMSO and then diluted in medium A. The concentration of DMSO during this study is 1.5%. The solutions and the dilutions were prepared extemporaneously in order to avoid or reduce oxidation of I-152 by DMSO to its disulfide.

3.3.2. Virus and Infection of the Cells

The MDMs were infected with the reference isolate with macrophage tropism, HIV-1/Ba-L. The PBMCs and the PBLs were infected with the reference isolate with lymphocyte tropism HIV-1 LAI. The viral stock were formed by amplifying these strains in vitro using umbilical blood mononucleated cells (UBM(s)) preactivated with 1 µg/ml of PHA-P and cultured in medium A supplemented by 20 IU/ml of IL-2. In order to remove the soluble factors, such as cytokines, the culture supernatants were ultracentrifuged at 360 000 g for 5 min, and the pellets were resuspended in RPMI 1640. The viral stocks thus formed were subsequently titred using PBMCs activated with PHA-P. The TCID50s (50% Tissue Culture Infectious Dose) were calculated using the Kärber formula.

A million MDMs were infected with 10 000 TCID50s of the HIV-1/Ba-L strain. This amount of virus corresponds to a multiplicity of infection (m.o.i.) equal to 0.01. The excess of virus is removed 24 h after by washing with cells using RPMI 1640. The PBLs and the PBMCs were infected with 10 000 TCID50s of the HIV-1 LAI strain (moi=0.01). The cells were washed at the end of the second day of infection.

3.3.3. Assaying the Viral Replication in the Culture Supernatants

3.3.3.1 Assaying the Reverse Transcriptase (RT) Activity

The viral replication is measured by assaying the RT activity in the culture supernatants according to the technique described by F. Rey et al. (*Biochem. Biophys. Res. Comm.*, 1984, 121, 126–133). The radioactivity incorporated during the extension of the complementary strand of a poly-rA synthetic matrix in the presence of an oligo-dT$_{12-18}$ primer and of a radiolabeled substrate, [$^3$H-methyl] thymidine-5'-triphosphate ([$^3$H]TPP), makes it possible to assay the enzymatic activity of RT. 400 µl of supernatant are ultracentrifuged at 360 000 g for 5 min. The RT is released by lysis of the viral pellet in 20 µl of NTE-Triton (100 mM NaCl, 10 mM Tris, 1 mM EDTA, 0.1% Triton X-100). These 20 µl are subsequently incubated with 40 µl of the following reaction mixture: 62.5 mM Tris, pH 7.8; 25 mM KCl; 6.25 mM MgCl$_2$; 1.25 mM dithiothreitol (DTT); 2.5×10$^{-3}$ ODU oligo-dT$_{12-18}$ and poly-rA, 5.55×10$^{-3}$ TBq {$^3$H]TTP. After one hour at 37° C., the enzymatic reaction is halted and the newly synthesized strands are precipitated for 20 min at 4° C. by the addition of 1 ml of sodium pyrophosphate (NaPP), of 50 µl of yeast DNA (0.1 mg/ml in 5% trichloroacetic acid (TCA)), and of 4 ml of 20% TCA. The mixture is filtered using a cellulose acetate membrane (Millipore) which retains the radiolabeled poly-dT chains. The filter is washed using 20 ml of 5% TCA and the residual water is removed by addition of 25 µl of 70% ethanol. The filter is dried in an oven for 10 minutes at 80° C. and is then introduced into vials containing 8 ml of liquid scintillant. The β radioactivity is quantified by means of a scintillation counter (Packard Bell). The results are expressed in pM of [$^3$H]-TMP incorporated/h/ml of supernatant or, more simply, in cpm/h/ml.

3.3.3.2 Assaying the P25 Protein

The assaying of the p25 protein is carried out using the ELISA kit from DuPont de Nemours. 200 µl of the culture supernatant to be tested are placed in a well of a microtitration plate. The addition of 20 µl of lysis buffer releases the viral proteins in the medium. The released antigen attaches to a mouse anti-p25 monoclonal antibody immobilized at the bottom of the wells. After incubating for 2 h at 37° C., 3 washing operations using 5 ml of washing buffer are carried out and then 100 µl of a biotinylated polyclonal antibody which reacts with the immobilized antigen are incubated for 1 h at 37° C. The series of 3 washing operations in the same buffer and with the same volume is again carried out before the addition over 15 min at 37° C. of 100 µl of Raifort-streptavidin peroxidase conjugate which will make it possible to amplify the colorimetric reaction. The complex formed is revealed, after 3 washing operations using 5 ml of the washing buffer of the kit, with 100 µl of o-phenylenediamine (OPD) dihydrochloride. After incubating for 30 min at ambient temperature, the reaction is halted by the addition of 100 µl of 4N sulfuric acid. The OD of the coloring thus obtained is read at 490 mm. This absorbence is directly proportional to the amount of attached antigen. The linear relationship relating the O.D. to the p25 concentration is established by virtue of a standard range produced from a recombinant p25 solution.

3.3.4. Analysis of the Results and Determination of the 50% Effective Doses The 50% effective doses (ED50) are calculated from the cumulative RT activities using the software "Dose-effects analysis with microcomputers" developed by J. Chou & T. C. Chou.

3.3.5. Measurement of the Cell Viability

These tests are carried out systematically in parallel with the evaluation of the antiviral activity. In view of the oxidation/reduction capacity of the molecules tested, the test with the tetrazolium salt, which measures the activity of mitochondrial dehydrogenases, cannot be used.

3.3.5.1. Measurement using an Exclusion Dye, Trypan Blue

The nonadherent cells, such as the PBMCs and the PBLs, are counted using a Malassez cell and an exclusion dye, trypan blue (TB). 25 µl of the cell suspension are added to 475 µl of TB. This count is carried out after the isolation of the PBMCs and the PBLs, before the plating, and at each replacement of the culture medium.

3.3.5.2. Measurement Using a Vital Dye, Neutral Red

Neutral red (NR) is a vital dye which makes it possible to measure the viability of adherent cells, such as MDMs. 600 µl of culture supernatant are removed and replaced with 400 µl of an NR solution (0.001% m/v in phosphate buffer, PBS, Boehringer Mannheim), filtered at 0.45 µm. The cells were incubated for 1 h at 37° C. and are subsequently washed (2×1 ml of PBS). The cells are then lysed at −20° C. with 200 µl of a 50% ethanol mixture comprising 1% of glacial acetic acid. The OD is measured twice with 100 µl of solution using a spectrophotometer.

3.4. Study of the Mechanism of Action of I-152

3.4.1. Quantification of the Proviral DNAs by PCR

I-152 is composed of MEA and NAC, which are capable of interacting with the early phases of the biological cycle of HIV. It is therefore capable of decreasing the integration of the provirus into the cell genome. In order to measure these effects, the proviral DNAs were quantified by PCR. The cells were lysed using 1 ml of the following lysis solution: 10 mM Tris HCl pH 8; 100 mM of EDTA pH 8; 0.5% of sodium dodecyl sulfate (SDS); 20 µg/ml of DNAse-free bovine pancreatic RNAse. 200 µg/ml of proteinase K are subsequently added to this suspension. The DNAs were subsequently extracted using 1 ml of an ice-cold saturated phenol solution and 1 ml of a phenol/Chisam solution.

The viral DNAs were then amplified by means of specific primers of the gag gene (SK01/SK39) and of a standard range of the 8E5 line, a chronically infected line, the cells of which carry a proviral copy. The β-globin gene was used as reporter gene in order to make sure of the quality of the DNA extraction.

3.4.2. Acellular Test of the Enzymatic Activity of RT

The I-152 molecule is composed of NAC and MEA, which are capable of inhibiting the activity of RT (A. Bergamini et al., *J. Clin. Invest.*, 1994, 93, 2251–2257). For this reason, the inhibiting capacity of I-152 with respect to the RT activity was measured using an acellular test. This test was carried out according to the protocol described above (§ 3.3.3.1.). In the reaction mixture, only the 20 µl of water are replaced by 20 µl of a concentration of I-152 or of the reference compounds. Heparin, known for inhibiting the activity of RT and of the other DNA polymerases, is used as positive control for inhibition.

3.4.3. Assaying the Total Glutathione

The method for assaying the total glutathione (GSH+GSSG) which we used is an adaptation, to the MDM culture system, of that described by O. W. Griffith et al. (*Anal Biochem.*, 1980, 106, 207–212). The assayings were carried out 24 h after the beginning of the treatment by the various compounds. A million cells are washed three times in PBS and then lysed with 150 µl of a lysis buffer (0.1M phosphate pH=7.4; 0.15M NaCl; 0.1% BSA, 0.01% Azide, 0.1% Triton X-100; 0.05% 5'-sulfosalicylic acid). The standard range in doubling dilutions ranges from 50 µm to 1.5 nM of GSSG or of GSH. The test is carried out in triplicate. 85 µl of 0.6 mM NADPH, 25 µl of 6 mM DTNB and 130 µl of pure water are added to the samples. The latter are incubated at 30° C. for 10 min. At the time of reading, 20 µl of 1 U/ml GSSG reductase are added to all the wells. The absorbence is measured with the long pathway at 412 nm. The concentration of total glutathione is subsequently determined with respect to the values of the calibration curve, produced in parallel with the assaying, and by extrapolation in the region of the linear part of the curve.

EXAMPLE 4

Anti-HIV Activity of I-152 with Respect to Macrophages 4.1 Antiviral Activity of I-152 with Respect to MDMs Infected Extemporaneously 4.1.1. 50, 70 and 90% Effective Doses and Cytotoxicity of I-152

The cells of the macrophage line play a major role in oxidative "processes". The pro-GSH molecule, I-152, was therefore tested with respect to MDMs infected with the VIH-1/Ba-L strain. I-152, after intracellular metabolization, is capable of releasing NAC, MEA and cysteine (FIG. 1).

We compared the activities of I-152 with those of its two components, NAC and MEA, in our experimental system. I-152 has a strong antiviral activity superior to that of NAC or of MEA (FIG. 2, table 1). The inhibiting concentrations of NAC, of MEA and of I-152 are respectively equal to 9.4 mM, 300 µM and 50 µM. In the light of these figures, I-152 therefore appears to be 6 and 188 times more effective than MEA and NAC. However, these values do not reflect the difference between these three products. This is because, at antiviral doses, NAC and MEA are cytotoxic whereas I-152 is not cytotoxic. Thus, NAC is cytotoxic from 10 or 15 mM (FIG. 3: NAC 15 mM: 70% cytotoxicity; NAC 40 mM: 91%), and MEA decreases the viability of MDMs by 65% at the concentration of 500 µM (FIG. 3). On the other hand, I-152, even at doses 10 times greater than its 50% effective dose (ED), is not cytotoxic (FIG. 3: 500 µM).

4.1.1.2. Effect of I-152 on the Production of the Major Protein of the Viral Nucleocapsid The viral replication can be measured in the culture supernatants by assaying either the enzymatic activity of RT or the major protein of the viral nucleocapsid, p25. In infected MDM cultures, the inhibition of the production of the p25 protein is concomitant with that of the RT activity (FIG. 4). These results therefore confirm the antiviral effectiveness of I-152.

4.1.1.3. Effect of the Multiplicity of Infection on the Antiviral Activity of I-152

During our first experiments, the cells were infected using 10 000 TCID50 (m.o.i.: 0.01). In order to measure the effects of the viral load on the anti-HIV activity of I-152, the cells are infected, in a second step, using 1 000 TCID50 (m.o.i.: 0.001).

The antiviral activity of I-152 increases when the m.o.i. is decreased (FIG. 5) and the ED turns out to be decreased thereby (table II, 3 µM vs. 50 µM).

4.1.2. Antiviral Activity of I-152 with Respect to Preinfected MDMs

The treatment of the cells 7 days after infection confirms the antiviral activity of I-152 (FIG. 6). This is because, at a dose of 500 µM, viral replication is extinguished. However, under these experimental conditions, the dose of 250 µM is ineffective. This shift in the inhibiting potential, observed between the various methods of treatment, suggests 1) that I-152 inhibits viral replication by probably combining two mechanisms: an early and a late mechanism, and 2) that, at high dose ($\geq 500$ µM), inhibition of the late phase of the biological cycle is sufficient.

4.2. Antiviral Activity of I-152 in Primary Cultures of Lymphocytes and of Peripheral Blood Mononuclear Cells After having shown the antiviral activity of I-152 with respect to cells of the macrophage line, its effects were measured with respect to peripheral blood lymphocytes (PBLs) and mixed population comprising monocytes/macrophages and lymphocytes, PBMCs. Furthermore, in order to measure the effects of cell activation on the antiviral activity of I-152, the cells were or were not activated by a mitogen, phytohemagglutinin-P (PHA-P).

4.2.1. Viability of the PBMCs and PBLs Treated with I-152

The cell viability was measured in parallel with the assessment of the antiviral activity. At each replacement of the culture medium, the viable cells were counted by means of an exclusion dye, trypan blue. In the PBMC and PBL cultures, I-152 is not cytotoxic. This is because the viability of the lymphocytes is not decreased in the PBL and PBMC cultures and, furthermore, in the latter, when the cells are not exposed to PHA-P, the monocytes differentiate into macrophages with a pseudofibroblastic appearance. On the other hand, NAC and MEA are cytotoxic for both cell types from doses of 10 or 15 mM and 500 µM respectively.

4.2.2. Antiviral Activity of I-152 with Respect to Quiescent PBMCs or PBMCs Activated by PHA-P, and Infected The PBMCs, quiescent or activated by PHA-P, were infected by the reference strain with lymphocyte tropism HIV-1 LAI. All the culturings were carried out in parallel and the drugs were maintained throughout the culturing.

In both cell populations, MEA and NAC do not inhibit viral replication at known cytotoxic doses (results not presented). In the quiescent PBMCs, I-152 inhibits viral replication by 97 and 88% at doses of 250 and 125 $\mu$M respectively and, in the activated PBMCs viral replication is decreased by 42 and 25% at the same doses (FIG. 7).

4.2.3. Antiviral Activity of I-152 with Respect to Quiescent PBLs or PBLs Activated by PHA-P, and Infected with the HIV-1 LAI Strain As in the PBMCs cultures, MEA and NAC do not have or have a very slight antiviral activity in PBLs (results not presented). On the other hand, I-152 inhibits viral replication in quiescent PBLs or PBLs activated by PHA-P (FIG. 8).

4.3. Anti-HIV Activity of I-152 with Respect to Tissue Macrophages 4.3.1. Isolation of Spleen Monocytes/Macrophages The spleen is dissected and sieved and then the mononuclear cells are isolated using a density gradient, on a Ficoll cushion. The monocytes/macrophages are obtained by adherence to the plastic. The monocytes were allowed to differentiate into macrophages for 7 days, at which time they were infected.

4.3.2. Results

The monocyte/macrophage plays a deleterious role in the physiopathology of infections by the HIV as it constitutes an important site for retroviral replication within tissues. As these tissues are not very accessible to current anti-HIV therapy, this cell population is regarded as a "reservoir".

Retroviral replication within this cell population, and thus the effectiveness of a molecule such as I-152, is conditioned partly by the level of cell differentiation. It was therefore important to make sure of the antiviral effectiveness of I-152 in monocytes/macrophages with a degree of maturation which can be different from that of MDMs. We have thus evaluated the antiviral activity of I-152 and its ability to regenerate the intracellular level of GSH in spleen macrophages. In this cell populations, the HIV-1/Ba-L strain also replicates at high noise. The I-152 molecule has proved to be as effective in human spleen macrophages as in macrophages derived from blood monocytes. This is because the concentration of 38 $\mu$M decreases HIV replication by 50% in this spleen cell population (table III). Likewise, as in the macrophages derived from blood monocytes, I-152 increases the intracellular level of GSH in a dose-dependent way which can be saturated from 250 $\mu$M (FIG. 15). It should be noted that, in the spleen macrophages, as in the macrophages derived from blood monocytes, infection by HIV leads to a deficiency of GSH (MDM; FIG. 16).

4.4. Mechanism of Action of I-152

4.4.1. Effect of I-152 on the Integration of the Proviral Genome within the Cell Genome Cell culture experiments would suggest that I-152 inhibits HIV replication by probably combining two mechanisms, the one early and the other late. In order to measure the effects of this molecule on the early phases of the biological cycle of the HIV, the integration of the provirus within the cell genome was quantified by PCR. I-152 inhibits the integration of the provirus. This inhibition is much greater than that induced by NAC or MEA. On the other hand, it is not perfect, unlike that induced by 10 $\mu$M AZT (FIG. 9).

4.4.2. Effect of I-152 on the Enzymatic Activity of RT in an a Cellular System

In view of the preceding results and because MEA is capable of inhibiting the activity of RT, the effects of I-152 on the activity of this enzyme were measured in an acellular system. The experiment was carried out in duplicate and heparin was used as control of the inhibition of the activity RT. In both cases, heparin at the concentration of 1 mg/ml completely inhibits the RT activity of the HIV-1 LAI isolate. This inhibition is dose-dependent. Likewise, MEA decreases by 29±1% (exp. 1, FIG. 10) and 48±4% (exp. 2 not presented) at a dose of 500 $\mu$M. On the other hand, NAC and I-152 do not exhibit an inhibiting activity with respect to the RT of the HIV in our experimental system (FIG. 10). These results confirm that I-152, by releasing MEA, can interact with an early stage of the biological cycle of the HIV.

4.4.3. Effect of I-152 on the Intracellular Concentration of Glutathione

The late effects of I-152 are probably the more direct consequence of its proglutathione activity. In order to make sure of this activity in lymphocytes and macrophages, the intracellular concentrations of total glutathione (GSH+GSSG) were determined in PBMC cultures (FIG. 11). Of the two reference molecules, NAC is better at increasing the intracellular level of glutathione in quiescent PBMCs. This is because MEA does not significantly alter the intracellular level of glutathione, at the very least at the doses tested. In our experiments, the doses of NAC used are higher than those of MEA, which may explain the difference observed in the intracellular level of glutathione.

I-152 increases the intracellular level of glutathione. This increase follows a bell-shaped curve with an optimum at 25 and 125 $\mu$M. The dose of I-152 of 125 $\mu$M increases the cellular concentration up to 2.64±0.13 $\mu$M. This intracellular concentration is equivalent to that obtained with the dose of NAC of 15 mM. On considering the concentrations of molecules supplementing the culture medium, I-152 is 120 times more active than NAC, It should be noted that the intracellular concentrations of glutathione decrease at high concentrations, at the very least for MEA (500 $\mu$M) and I-152 (250 $\mu$M). This phenomenon is probably the consequence of the processes for the regulation of glutathione.

4.5 Antiviral Activity of the S-acylated Derivatives of I-152: I-176, I-177 and I-178, with Respect to MDMs Infected Extemporaneously During a second series of experiments, the antiretroviral activities of the I-152 derivatives were tested with respect to MDMs infected by the HIV-1/Ba-L strain (FIG. 12). These molecules are lipophilic and were thus dissolved in dimethyl sulfoxide (DMSO) and then diluted. I-152, which acts as reference, was treated in the same way. Under these experimental conditions, I-152 proved to be the most effective in inhibiting viral replication. However, it should be noted that DMSO decreases its antiviral effectiveness and that the standard deviation is high as the antiviral activity was decreased with respect to two of the three wells of the culture triplicate. The compound I-176 is slightly toxic at 150 $\mu$M, which may also explain the variability within the culture triplicate and the size of the standard deviation observed. To date, none of the S-acylated derivatives has shown, in vitro, an activity superior to that of the mother molecule. Nevertheless, I-177 and I-178 have activities similar to that of I-152, and, in view of the importance of the latter, these two molecules, which are more lipophilic, are to be retained. It may have advantages in the case of clinical experimentations. This is because they can have pharmaceutical dosage forms and methods of administration different from those of I-152.

EXAMPLE 5

Effect of I-152 on the Intracellular Concentration of GSH 5.1. Materials and Methods With the exception of materials and methods presented below, the procedures are similar to those described in the preceding examples.

The intracellular GSH was assayed by means of the assay kit sold by Cayman. This method for assaying glutathione is an adaptation of that described by O. W. Griffith et al. (1980).

The compound I-152 and its derivatives are prepared extemporaneously by being dissolved in dimethyl sulfoxide (DMSO) at the concentration of 100 mM. They are subsequently stored at −20° C. after having been diluted 10 fold in phosphate buffer (PBS).

5.2. Results

The effects of the compound I-152 in increasing the intracellular concentration of GSH were demonstrated in cells not exposed to an oxidative stress. The present results show that this molecule is also capable of regenerating an abnormally low intracellular level. This is because the infection of macrophages derived from human blood monocytes (MDMs) leads to an intracellular deficiency of GSH (FIG. 13); this deficiency is accompanied by an increase in the expression of the enzymes involved in maintaining this level and by an increase in 8-isoprostane, evidence of an oxidative stress (results not presented).

EXAMPLE 6

Effect of I-152 on the Macrophage Synthesis of TNF-α

6.1. Materials and Methods

With the exception of materials and methods presented below, the procedures are similar to those described in the preceding examples.

The synthesis of tumor necrosis factor (TNF-α) was modified in the MDM culture supernatants using the calorimetric kit sold by Cayman.

The compound I-152 and its derivatives are prepared extemporaneously by being dissolved in dimethyl sulfoxide (DMSO) at the concentration of 100 mM. They are subsequently stored at −20° C. after having been diluted 10 fold in phosphate buffer (PBS).

6.2. Results

Tumor necrosis factor (TNF-α), like the oxygen-comprising or nitrogen-comprising radical components, plays a major role in the apoptotic processes associated with infection the HIV. Furthermore, the radical components can promote the synthesis of this proinflammatory cytokine. For this reason, the effects of I-152 in decreasing the synthesis of TNF-α were thus looked for in MDMs stimulated by a bacterial lipopolysaccharide and interferon (IFN-γ). The compound I-152 inhibits the synthesis of TNF-α and increases the concentration of GSH under these experimental conditions (FIG. 14).

EXAMPLE 7

Potentiation of the Antiretroviral Activity of AZT by the Compound I-152

7.1. Materials and Methods

With the exception of materials and methods presented below, the procedures are similar to those described in the preceding examples.

Viral replication was measured by assaying the reverse transcriptase activity in culture supernatants using the RetroSys kit from Innovagen, following the recommendations of the company.

The compound I-152 and its derivatives are prepared extemporaneously by being dissolved in dimethyl sulfoxide (DMSO) at the concentration of 100 mM. They are subsequently stored at −20° C. after having been diluted 10 fold in phosphate buffer (PBS).

7.2. Results

The pro-GSH compounds of the "I-152 family" are preferably administered as adjuvants therapeutic for current antiretrovirals. The inventors have thus attempted to measure in vitro the effects of I-152 with respect to the anti-HIV effectiveness of these molecules. This study was carried out using macrophages derived from human blood monocytes infected by the HIV-1/Ba-L strain and according to the methodology described by J. and T C. Chou for quantifying the synergistic effects, additive or antagonistic, between two molecules.

In our experimental model, the compound I-152 potentiates the anti-HIV activity of AZT. This is because the combination index (CI) is less than 1, which testifies to a synergy between the two compounds tested (FIG. 17).

EXAMPLE 8

Antiretroviral Activity of the Acylated Analogues of I-152 or of its Derivatives 8.1. Materials and Methods With the exception of materials and methods presented below, the procedures are similar to those described in the preceding examples.

The 50% effective doses (ED50) are calculated from the cumulative RT activities using the software "Dose-effects analysis with microcomputers" developed by J. Chou and T. C. Chou.

The compound I-152 and its derivatives are prepared extemporaneously by being dissolved in dimethyl sulfoxide (DMSO) at a concentration of 100 mM. They are subsequently stored at −20° C. after having been diluted 10 fold in phosphate buffer (PBS).

8.2. Results

The anti-HIV activity of about twenty I-152 derivatives, in addition to that of the S-acylated compounds I-176, I-177 and I-178, was evaluated in the system of MDMs infected in vitro by the HIV-1/Ba-L strain. These compounds attempted, to some extent, to be more lipophilic; they are thus capable of making possible pharmaceutical dosage forms and methods of administration different from those of I-152. Furthermore, these derivatives constitute the first link in the structure-activity study which should make it possible to identify important residues in the activity of this family of compounds. The "stock" solutions of these compounds were treated with ultrasound in order to improve the solubility of the products.

Nine compounds demonstrated a significant antiviral activity of the same order as that of I-152 (tables IV and V). The values obtained with the compound I-152 which are presented in these two tables perfectly illustrate the reproducibility of the anti-HIV effects of I-152 from one experiment to another and/or and from one cell donor to another. This is because the values presented in table III result from a first experiment carried out using cells from one donor and those presented in table IV from a second experiment carried out using cells from another donor.

In conclusion, the compound I-152 or one of its analogues or of its derivatives constitutes an excellent adjuvant therapeutic for current antiretrovirals, such as AZT, and optionally for other classes of antiretroviral molecules currently used in human clinical treatment (i.e. nonnucleoside reverse transcriptase inhibitors and viral protease inhibitors) while being capable of reorganizing both damage to the immune system and that to the oxidative metabolism. Furthermore, these results have demonstrated the biological activities of other molecules which are derivatives and/or analogues of I-152, the subject matter of the present invention; which henceforth constitutes a family of molecules which are biologically active and which can potentially be used as therapy.

The ability to increase the intracellular level of GSH and also to regenerate this tripeptide under conditions of stress where reference molecules, such as NAC and MEA, are ineffective is also highly advantageous. These powerful antioxidant and, probably antiapoptotic (if it is considered that the radical components and TNF-α play a major role in these deleterious processes) activities are in favor of a promotion of the compound I-152 in other noninfectious situations.

References

Abrams, 1991, Am. J. Med., 91, 106–112.
Barnett et al., 1969, J. Amer. Chem. Soc., 91, 2358–2369.
Bergamini et al., 1994, J. Clin. Invest., 93, 2251–2257.
Bosegaard et al., 1993, J. Pharmacol. Exp. Ther., 265, 1239–1244.
Brückner et al., 1989, J. Chromatogr., 476, 73–82.
Figdor et al., 1983, Cell, Biophys., 5, 105–118.
Griffith et al., 1980, Anal. Biochem., 106, 207–212.
Heller et al., 1997, Advances in Pharmacology, 38, 629–638.
Herzenberg et al., 1997, Proc. Natl. Acad. Sci., 94, 1967–1972.
Horowitz, 1991, Am. J. Med., 91, 113–117.
Rabinovitch et al., 1992, Diabetologie, 35, 409–413.
Rey et al., 1984, Biochem. Biophys, Res. Comm., 121, 126–133.
Volante, 1981, Tetrahedron Lett., 22, 3119–3122.
Wieland and Bokelman, 1952, Ann. Chem., 576, 20–34.
Zee-cheng et al., 1970, J. Med. Chem., 13, 414–418.

What is claimed is:

1. A process for the preparation of a compound of general formula:

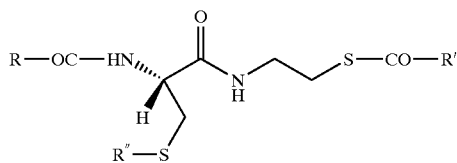

(I)

in which:
R and R' independently represent a linear or branched $C_1$–$C_7$ alkyl radical or an aryl group which is unsubstituted or substituted by one or more radicals chosen from halogens, linear or branched $C_1$–$C_3$ alkyl radicals and —OH radicals;
R" is hydrogen or a CO—$R^1$ group in which $R^1$ is a linear or branched $C_1$–$C_7$ alkyl radical or an aryl group which is unsubstituted or substituted by one or more radicals chosen from halogens, linear or branched $C_1$–$C_3$ alkyl radicals and —OH radicals; and
the dimers formed by a disulfide bridge from one and/or other of the two sulfur atoms of the compounds of general formula I composed of the R" radicals or of the R'CO— radicals of the two molecules, and the corresponding thiazolidine forms;

said process comprising the following stages:
a) protection of the N-acyl-L-cysteine to provide the N-acyl-S-trityl-L-cysteine compound; then
b) coupling of the protected N-acyl-S-trityl-L-cysteine with the S-acetylcysteamine hydrochloride to provide the N-(N-acyl-S-trityl-L-cysteinyl)-S-acylcysteamine compound.

2. A process for the preparation of a compound of general formula:

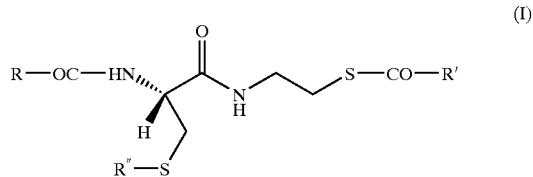

(I)

in which;
R and R' independently represent a linear or branched $C_1$–$C_7$ alkyl radical or an aryl group which is unsubstituted or substituted by one or more radicals chosen from halogens, linear or branched $C_1$–$C_3$ alkyl radicals and —OH radicals;
R" is hydrogen or a CO—$R^1$ group in which $R^1$ is a linear or branched $C_1$–$C_7$ alkyl radical or an aryl group which is unsubstituted or substituted by one or more radicals chosen from halogens, linear or branched $C_1$–$C_3$ alkyl radicals and —OH radicals; and
the dimers formed by a disulfide bridge from one and/or other of the two sulfur atoms of the compounds of general formula I composed of the R" radicals or of the R'CO— radicals of the two molecules, and the corresponding thiazolidine forms;
wherein said compound is in the thiazolidine form and wherein said process comprises the following stages:
a) protection of the N-acyl-L-cysteine to provide the N-acyl-S-trityl-L-cysteine compound; then
b) coupling of the protected N-acyl-S-trityl-L-cysteine with thiazolidine.

3. The process as claimed in claim 1 or 2, wherein R is a methyl group (—CH₃).

4. The process as claimed in claim 3, wherein R' is a methyl group (—CH₃).

5. The process as claimed in claim 4, wherein R" is hydrogen (Compound N-(N-acetyl-L-cysteinyl)-S-acetylcysteamine).

6. The process as claimed in claim 4, wherein R" is an acetyl group (—COCH₂) (Compound N-(N,S-bisacetyl-L-cysteinyl)-S-acetylcysteamine).

7. The process as claimed in claim 4, wherein R" is an isobutyryl group (—COCH(CH₃)₂) (Compound N-(N-acetyl-S-isobutyryl-L-cysteinyl)-S-acetylcysteamine).

8. The process as claimed in claim 4, wherein R" is a pivaloyl group (—COC(CH₃)₃) (Compound N-(N-acetyl-S-pivaloyl-L-cysteinyl)-S-acetylcysteamine).

9. The process as claimed in claim 3, wherein R' is selected from the isopropyl group (—CH(CH₃)₂), the tert-butyl group (—C(CH₃)₃) and the phenyl group (—C₆H₅).

10. The process as claimed in claim 9, wherein R" is selected from hydrogen (—H), the acetyl group (—COCH₃), the isobutyryl group (—COCH(CH₃)₂), the pivaloyl group (—COC(CH₃)₃) or the benzoyl group (—CO—C₆H₅).

11. The process as claimed in claim 1 or 2, wherein R is an isopropyl group (—CH(CH$_3$)$_2$).

12. The process as claimed in claim 11, wherein R' is selected from the methyl group (—CH$_2$), the isopropyl group (—CH(CH$_3$)$_2$), the tert-butyl group (—C(CH$_3$)$_3$) and the phenyl group (—C$_6$H$_5$).

13. The process as claimed as claim 12, wherein R" is selected from hydrogen (—H), the acetyl group (—COCH$_3$), the isobutyryl group (—COCH(CH$_3$)$_2$), the pivaloyl group (—COC(CH$_3$)$_3$) or the benzoyl group (—CO—C$_6$H$_5$).

14. The process as claimed in claim 9, wherein R" is the trityl group.

15. The process as claimed in claim 12, wherein R" is the trityl group.

16. The process as claimed in claim 1 or 2, further comprising the following stages:
   c) deprotection of said compound obtained in said stage b); then
   d) release of the free thiol of formula I.

17. The process as claimed in claim 1 or 16, wherein said N-acyl-S-trityl-L-cysteine compound of stage a) is the compound N-acetyl-S-trityl-L-cysteine and wherein said S-acylcysteamine hydrochloride of stage b) is S-acetylcysteamine hydrochloride.

18. The process as claimed in claim 16, further comprising an S-acylation stage e).

* * * * *